United States Patent [19]
Müller et al.

[11] Patent Number: 6,075,049
[45] Date of Patent: Jun. 13, 2000

[54] PHENYLCARBAMATES, PROCESSES AND INTERMEDIATE PRODUCTS FOR THEIR PREPARATION AND THEIR USE AS PESTICIDES AND FUNGICIDES

[75] Inventors: Bernd Müller, Frankenthal; Hubert Sauter; Herbert Bayer, both of Mannheim; Wassilios Grammenos, Ludwigshafen; Thomas Grote, Schifferstadt; Reinhard Kirstgen, Neustadt; Klaus Oberdorf, Heidelberg; Franz Röhl, Schifferstadt; Norbert Götz, Worms; Michael Rack, Heidelberg; Ruth Müller, Friedelsheim; Gisela Lorenz, Hambach; Eberhard Ammermann, Heppenheim; Siegfried Strathmann, Limburgerhof; Volker Harries, Frankenthal, all of Germany

[73] Assignee: BASF Aktiengesellschaft, Ludwigshafen, Germany

[21] Appl. No.: 09/051,979
[22] PCT Filed: Oct. 22, 1996
[86] PCT No.: PCT/EP96/04575
  § 371 Date: Apr. 23, 1998
  § 102(e) Date: Apr. 23, 1998
[87] PCT Pub. No.: WO97/16415
  PCT Pub. Date: May 9, 1997

[30] Foreign Application Priority Data

Nov. 2, 1995 [DE] Germany .......................... 195 40 735

[51] Int. Cl.[7] .......................... A01N 37/34; C07C 255/49; C07C 271/28
[52] U.S. Cl. .......................... 514/506; 558/413; 558/414; 558/418; 558/419; 558/422; 560/22; 560/29; 560/43; 564/163; 564/52; 514/522; 514/524; 514/619; 514/598
[58] Field of Search .......................... 558/414, 413, 558/418, 419, 422; 560/43, 22, 29; 514/506, 522, 524, 598, 619; 564/163, 52

[56] References Cited

U.S. PATENT DOCUMENTS 5,543,433  8/1996  Doetzer et al. .

FOREIGN PATENT DOCUMENTS 2127110  1/1993  Canada .
619 301  10/1994  European Pat. Off. .
627 411  12/1994  European Pat. Off. .
93/15046  8/1993  WIPO .

*Primary Examiner*—Joseph McKane
*Assistant Examiner*—Ebenezer Sackey
*Attorney, Agent, or Firm*—Keil & Weinkauf

[57] ABSTRACT

Phenylcarbamates of the formula I

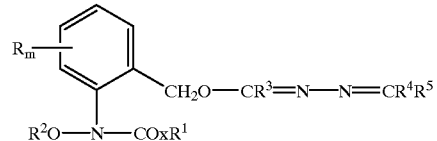

where the substituents and the index have the following meanings:

R is cyano, nitro, trifluoromethyl, halogen, alkyl or alkoxy;

m is 0, 1 or 2;

$R^1$ is alkyl, alkenyl, alkynyl, cycloalkyl or cycloalkenyl, and, in the event that X is $NR^a$, additionally hydrogen;

X is a direct bond, O or $NR^a$;

$R^a$ is hydrogen, alkyl, alkenyl, alkynyl, cycloalkyl or cycloalkenyl;

$R^2$ is hydrogen, substituted or unsubstituted alkyl, alkenyl, alkynyl, cycloalkyl, cycloalkenyl, cycloalkynyl, alkylcarbonyl or alkoxycarbonyl;

$R^3$ and $R^4$ independently of one another are hydrogen, cyano, nitro, hydroxyl, amino, halogen, hetaryloxy, hetarylthio, hetarylamino or N-hetaryl-N-alkylamino, and $R^5$ is one of the groups mentioned under $R^3$ or a group $CR^d$=$NOR^e$;

processes and intermediates for their preparation, and their use.

7 Claims, No Drawings

PHENYLCARBAMATES, PROCESSES AND INTERMEDIATE PRODUCTS FOR THEIR PREPARATION AND THEIR USE AS PESTICIDES AND FUNGICIDES

This appln is a 371 of PCT/EP96/04575 filed on Oct. 22, 1996.

The present invention relates to phenylcarbamates of the formula $$R_m \!-\!\! \underset{R^2O-N-COXR^1}{\bigcirc}\!\!-\!CH_2O-CR^3\!=\!N-N\!=\!CR^4R^5 \qquad I$$

where the substituents and the index have the following meanings:

R is cyano, nitro, trifluoromethyl, halogen, $C_1$–$C_4$-alkyl or $C_1$–$C_4$-alkoxy;

m is 0, 1 or 2, it being possible for the radicals R to be different if n is 2;

$R^1$ is alkyl, alkenyl, alkynyl, cycloalkyl or cycloalkenyl, and, in the event that X is $NR^a$, additionally hydrogen;

X is a direct linkage, O or $NR^a$;

$R^a$ is hydrogen, alkyl, alkenyl, alkynyl, cycloalkyl or cycloalkenyl;

$R^2$ is hydrogen, unsubstituted or substituted alkyl, alkenyl, alkynyl, cycloalkyl, cycloalkenyl, cycloalkynyl, alkylcarbonyl or alkoxycarbonyl;

$R^3$ and $R^4$ independently of one another are hydrogen, cyano, nitro, hydroxyl, amino, halogen,
$C_1$–$C_6$-alkyl, $C_1$–C6-alkoxy, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_2$–$C_6$-alkenylthio, $C_2$–$C_6$-alkenylamino, N—$C_2$–$C_6$-alkenyl-N—$C_1$–$C_6$-alkylamino, $C_2$–$C_6$-alkynyl, $C_2$–$C_6$-alkynyloxy, $C_2$–$C_6$-alkynylthio, $C_2$–$C_6$-alkynylamino, N—$C_2$–$C_6$-alkynyl-N—$C_1$–$C_6$-alkylamino, it being possible for the hydrocarbon radicals of these groups to be partially or fully halogenated and/or to have attached to them one to three of the following radicals:

cyano, nitro, hydroxyl, mercapto, amino, carboxyl, aminocarbonyl, aminothiocarbonyl,
$C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, aryl-$C_1$–$C_4$-alkoxy, arylthio, aryl-$C_1$–$C_4$-alkylthio, hetaryl, hetaryloxy, hetaryl-$C_1$–$C_4$-alkoxy, hetarylthio and hetaryl- $C_1$–$C_4$-alkylthio, it being possible for the cyclic radicals, in turn, to be partially or fully halogenated and/or to have attached to them one to three of the following groups: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio and $C(=NOR^b)$—$A_n$—$R^c$;

$C_3$–$C_6$-cycloalkyl, $C_3$–$C_6$-cycloalkyloxy, $C_3$–$C_6$-cycloalkylthio, $C_3$–$C_6$-cycloalkylamino, N—$C_3$–$C_6$-cycloalkyl-N—$C_1$–$C_6$-alkylamino, $C_5$–$C_8$-cycloalkenyl, $C_5$–$C_8$-cycloalkenyloxy, $C_5$–$C_8$-cycloalkenylthio, $C_5$–$C_8$-cycloalkenylamino, N—$C_5$–$C_8$-cycloalkenyl-N—$C_1$–$C_6$-alkylamino, heterocyclyl, heterocyclyloxy, heterocyclylthio, heterocyclylamino, N-heterocyclyl-N—$C_1$–$C_6$-alkylamino, aryl, aryloxy, arylthio, arylamino, N-aryl-N—$C_1$–$C_6$-alkylamino, hetaryl, hetaryloxy, hetarylthio, hetarylamino, N-hetaryl-N—$C_1$–$C_6$-alkylamino, it being possible for the cyclic radicals to be partially or fully halogenated and/or to have attached to them one to three of the following groups:

cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-alkoxy-$C_1$–$C_6$-alkyl, $C_1$–$C_6$-haloalkoxy, $C_1$–$C_6$-alkoxycarbonyl, $C_1$–$C_6$-alkylcarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, aryl-$C_1$–$C_6$-alkoxy, aryl, aryloxy, hetaryl, hetaryloxy, it being possible for the cyclic radicals of the six last-mentioned groups to be partially or fully halogenated and/or to have attached to them a $C_1$–$C_6$-alkyl group; $C(=NOR^b)$—$A_n$—$R^c$ or $NR^f$—CO—D—$R^g$;

A is oxygen, sulfur or nitrogen, the nitrogen having attached to it hydrogen or $C_1$–$C_6$-alkyl;

D is a direct linkage, oxygen or $NR^h$;

n is 0 or 1;

$R^b$ and $R^c$ independently of one another are hydrogen or $C_1$–$C_6$-alkyl;

$R^f$ is hydrogen, hydroxyl, $C_1$–$C_6$-alkyl, $C_2$–$C_6$-alkenyl, $C_2$–$C_6$-alkynyl, $C_1$–$C_6$-alkoxy, $C_2$–$C_6$-alkenyloxy, $C_2$–$C_6$-alkynyloxy, $C_1$–$C_6$-alkoxy-$C_1$–$C_6$-alkyl, $C_1$–$C_6$-alkoxy-$C_1$–$C_6$-alkoxy and $C_1$–$C_6$-alkoxycarbonyl;

$R^g$, $R^h$ independently of one another are hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl and hetaryl-$C_1$–$C_6$-alkyl;

$R^5$ is one of the groups mentioned under $R^3$ or a group $CR^d=NOR^e$;

$R^d$ is one of the groups mentioned under $R^3$;

$R^e$ is hydrogen, $C_1$–$C_{10}$-alkyl, $C_3$–$C_6$-cycloalkyl, $C_2$–$C_{10}$-alkenyl, $C_2$–$C_{10}$-alkynyl, $C_1$–$C_{10}$-alkylcarbonyl, $C_2$–$C_{10}$-alkenylcarbonyl, $C_2$–$C_{10}$-alkynylcarbonyl or $C_1$–$C_{10}$-alkylsulfonyl, it being possible for these radicals to be partially or fully halogenated and/or to have attached to them one to three of the following groups:

cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$- alkylaminothiocarbonyl, $C_2$–$C_6$-alkenyl, $C_2$–$C_6$-alkenyloxy, $C_3$–$C_6$-cycloalkyl, $C_3$–$C_6$-cycloalkyloxy, heterocyclyl, heterocyclyloxy, benzyl, benzyloxy, aryl, aryloxy, arylthio, hetaryl, hetaryloxy and hetarylthio, it being possible for the last twelve groups mentioned, in turn, to be partially or fully halogenated and/or to have attached to them one to three of the following groups:

cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio or $C(=NOR^b)$—$A_n$—$R^c$;

aryl, arylcarbonyl, arylsulfonyl, hetaryl, hetarylcarbonyl or hetarylsulfonyl, it being possible for these radicals to be partially or fully halogenated and/or to have attached to them one to three of the following groups:

cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy or $C(=NOR^b)$—$A_n$—$R^c$, and to their salts.

Furthermore, the invention relates to processes and intermediates for the preparation of these compounds and to compositions comprising them for controlling animal pests and harmful fungi.

Anilides for controlling harmful fungi are disclosed in the literature (WO-A 93/15046). Moreover, DE-A 44 41 674 (= WO 96/16030) describes anilides which act against animal pests and harmful fungi.

It is an object of the present invention to provide compounds with an improved activity.

We have found that this object is achieved by the phenylcarbamates I defined at the outset. We have furthermore found processes and intermediates for their preparation and compositions comprising them for controlling animal pests and harmful fungi, and their use for this purpose.

The compounds I are accessible via a variety of routes by methods known per se from the literature.

In principle, it is irrelevant when synthesizing the compounds I whether the group —N(OR$^2$)—COXR$^1$ or the group —CH$_2$OCR$^3$=NN=CR$^4$R$^5$ is constructed first.

The way in which the —CH$_2$OCR$^3$=NN=CR$^4$R$^5$ side chain is synthesized depends essentially on the type of the substituent R$^3$. For reasons of clarity, the group —N(OR$^2$)—COXR$^1$, or a suitable precursor of this group, is abbreviated to # in the equations which follow.

If # is —N(OR$^2$)—COXR$^1$, β denotes compounds of the formula II and α denotes compounds of the formula I.

If # is —NHOH, β denotes L$^1$-substituted ortho-hydroxyaminotoluene which is substituted by R$_m$, and α denotes compounds of the formula V. If # is —NO$_2$, β denotes L$^1$-substituted ortho-nitrotoluene which is substituted by R$_m$ and α denotes compounds IV.

1.1 In the event that R$^3$ is not halogen, a procedure is generally followed when constructing the —CH$_2$OCR$^3$=NN=CR$^4$R$^5$ side chain in which a benzyl derivative of the formula β is reacted with a carbohydrazide of the formula III.

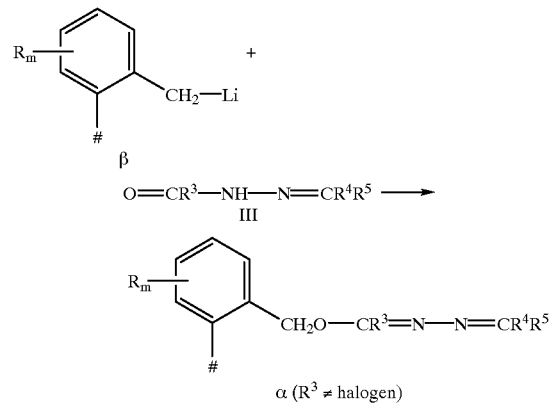

$L^1$ in formula β, is a nucleophilically exchangeable leaving group, eg. halogen or sulfonate groups, preferably chlorine, bromine, iodine, mesylate, tosylate or triflate.

This reaction is usually carried out at from −10° C. to 80° C., preferably 0° C. to 50° C., in an inert organic solvent in the presence of a base [cf. Houben-Weyl, Vol. E 14b, p. 370 et seq. and Houben-Weyl, Vol. 10/1, p. 1189 et seq.].

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and also dimethyl sulfoxide, dimethylformamide and water, especially preferably dimethylformamide, acetonitrile, toluene, tert-butyl methyl ether and water. Mixtures of these can also be used.

Suitable bases are, generally, inorganic compounds such as alkali metal hydroxides and alkaline earth metal hydroxides such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal hydrides and alkaline earth metal hydrides such as lithium hydride, sodium hydride, potassium hydride and calcium hydride, alkali metal amides such as lithium amide, sodium amide and potassium amide, alkali metal carbonates and alkaline earth metal carbonates such as lithium carbonate and calcium carbonate, and also alkali metal hydrogen carbonates such as sodium hydrogen carbonate, organometal compounds, in particular alkali metal alkyls such as methyllithium, butyllithium and phenyllithium, alkylmagnesium halides such as methylmagnesium chloride, and alkali metal alkoxides and alkaline earth metal alkoxides such as sodium methoxide, sodium ethoxide, potassium ethoxide, potassium tert-butoxide and dimethoxymagnesium, furthermore organic bases, eg. tertiary amines such as trimethylamine, triethylamine, triisopropylamine and N-methylpiperidine, pyridine, substituted pyridines such as collidine, lutidine and 4-dimethylaminopyridine, and also bicyclic amines. Sodium hydride, potassium hydroxide, potassium carbonate and triethylamine are especially preferred.

In general, the bases are employed in catalytic amounts, but they can also be used in equimolar amounts, in an excess or, if desired, as the solvent.

The starting materials are generally reacted with each other in equimolar amounts. It may be advantageous for the yield to employ III in an excess based on β.

Those starting substances of the formula II required for the preparation of compounds I which have not already been described in the literature cited at the outset can be prepared by the methods described therein.

Equally, those starting substances of the formula III which are not already known from the literature [cf. *Tetrahedron* 1987, 4185; Houben-Weyl, *Register der Stoffklassen* [*Register of Substance Classes*] Part A, Vol. 16/2, p. 439 et seq.] can be prepared by the known methods.

1.2 Compounds α where $R^3$ is a halogen atom are obtained by processes known per se from the corresponding precursors where the radical in question is a hydroxyl group [cf. Houben-Weyl, Vol. E 5, p. 631 et seq.; *J. Org. Chem.* 36, (1971) 233; *J. Org. Chem.* 57, (1992) 3245].

1.3 Compounds α where $R^3$ is bonded to the molecule skeleton via an O, S or N atom are obtained by processes known per se from the corresponding precursors where the radical in question is a halogen atom [cf. Houben-Weyl, Vol. E 5, p. 826 et seq.; *J. Org. Chem.* 36, (1971) 233; *J. Org. Chem.* 46, (1981) 3623].

1.4 Compounds α where $R^3$ is bonded to the molecule via an oxygen atom are also obtained by processes known per se by means of etherifying the corresponding precursors where the radical in question is a hydroxyl group [cf. Houben-Weyl, Vol. E 5, p. 826 et seq.; *Aust. J. Chem.* 27, (1974) 1341].

The construction of the group —N(OR²)—COXR¹ is known, for example, from the literature cited at the outset. For reasons of clarity, the $CH_2OCR^3=NN=CR^4R^5$ side chain, or a suitable precursor of this group, is abbreviated to * in the equations which follow.

If * is $CH_2OR^3=N-N=CR^4R^5$, δ denotes compounds of the formula IV, ε denotes compounds of the formula V and η denotes compounds of the formula I.

If * is $CH_2L^1$, δ denotes $L^1$-substituted ortho-nitrotoluene which is substitituted by $R_m$, ε denotes $L^1$-substituted ortho-hydroxyaminotoluene which is substituted by $R_m$ and η denotes $L^1$-substituted N-acyl(hydroxyamino)toluene which is substituted by $R_m$.

If * is $CH_3$, δ denotes an ortho-nitrotoluene which is substituted by $R_m$, ε denotes an ortho-hydroxyaminotoluene which is substituted by $R_m$ and η denotes an N-acyl (hydroxyamino)toluene which is substituted by $R_m$.

2.1 Compounds η where $R^2$ is hydrogen (IA) are generally obtained by reducing a nitrobenzene of the formula δ to give the corresponding hydroxylamine ε and then reacting ε to give η (where $R^2$=H) by means of reaction with an acylating agent of formula VI.

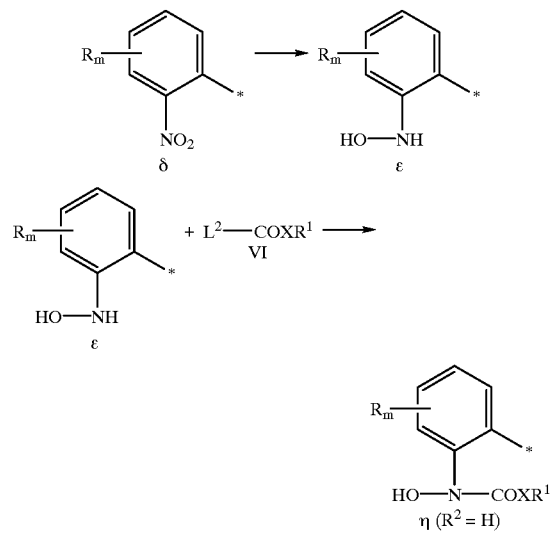

$L^2$ in formula VI is, for example, halogen or aryloxy, in particular chlorine and phenoxy.

a) The reduction of δ to the hydroxylamine ε is usually carried out at from −30° C. to 80° C., preferably 0° C. to 60° C., in an inert organic solvent in the presence of a catalyst [cf. DE Application No. 19 50 27 00.0].

b) The reaction of the hydroxylamine ε with VI is usually carried out at from −20° C. to 60° C., preferably 0° C. to 30° C., in an inert organic solvent in the presence of a base [cf. WO-A 93/15046].

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and also dimethyl sulfoxide, dimethylformamide and water, especially preferably cyclohexane, toluene, methylene chloride, tert-butyl methyl ether and water. Mixtures of these can also be used.

Suitable bases are, generally, inorganic compounds such as alkali metal hydroxides and alkaline earth metal hydroxides such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal hydrides and alkaline earth metal hydrides such as lithium hydride, sodium hydride, potassium hydride and calcium hydride, alkali metal amides such as lithium amide, sodium amide and potassium amide, alkali metal carbonates and alkaline earth metal carbonates such as lithium carbonate and calcium carbonate, and also alkali metal hydrogen carbonates such as sodium hydrogen carbonate, organometal compounds, in particular alkali metal alkyls such as methyllithium, butyllithium and phenyllithium, alkylmagnesium halides such as methylmagnesium chloride, and alkali metal alkoxides and alkaline earth metal alkoxides such as sodium methoxide, sodium ethoxide, potassium ethoxide, potassium tert-butoxide and dimethoxymagnesium, furthermore organic bases, eg. tertiary amines such as trimethylamine, triethylamine, triisopropylamine and N-methylpiperidine, pyridine, substituted pyridines such as collidine, lutidine and 4-dimethylaminopyridine, and also bicyclic amines. Potassium carbonate, sodium hydroxide and triethylamine are especially preferred.

In general, the bases are employed in catalytic amounts, but they can also be used in equimolar amounts, in an excess or, if desired, as the solvent.

The compounds η where $R^2$ is not hydrogen (IB) are obtained by reacting a compound of the formula η where $R^2$=H with a compound of the formula VII in a manner known per se.

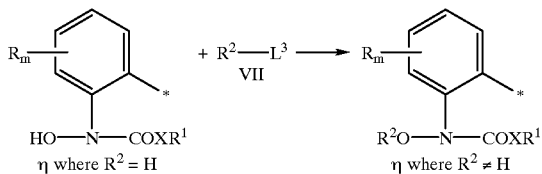

$L^3$ in formula VII is, for example, halogen, mesylate, tosylate, carboxylate and sulfate, in particular chlorine, bromine, mesylate and $R^2$—$OSO_3$—.

This reaction is usually carried out at from $-20°$ C. to $80°$ C., preferably $0°$ C. to $60°$ C., in an inert organic solvent in the presence of a base [cf. WO-A 93/15046].

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and also dimethyl sulfoxide and dimethylformamide, especially preferably acetone, toluene, tert-butyl methyl ether, cyclohexane and water. Mixtures of these can also be used.

Suitable bases are, generally, inorganic compounds such as alkali metal hydroxides and alkaline earth metal hydroxides such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal hydrides and alkaline earth metal hydrides such as lithium hydride, sodium hydride, potassium hydride and calcium hydride, alkali metal amides such as lithium amide, sodium amide and potassium amide, alkali metal carbonates and alkaline earth metal carbonates such as lithium carbonate and calcium carbonate, and also alkali metal hydrogen carbonates such as sodium hydrogen carbonate, organometal compounds, in particular alkali metal alkyls such as methyllithium, butyllithium and phenyllithium, alkylmagnesium halides such as methylmagnesium chloride, and alkali metal alkoxides and alkaline earth metal alkoxides such as sodium methoxide, sodium ethoxide, potassium ethoxide, potassium tert-butoxide and dimethoxymagnesium, furthermore organic bases, eg. tertiary amines such as trimethylamine, triethylamine, triisopropylamine and N-methylpiperidine, pyridine, substituted pyridines such as collidine, lutidine and 4-dimethylaminopyridine, and also bicyclic amines. Potassium carbonate, sodium hydroxide and triethylamine are especially preferred.

In general, the bases are employed in catalytic amounts, but they can also be used in equimolar amounts, in an excess or, if desired, as the solvent.

The reaction mixtures are worked up in the customary manner, eg. by mixing with water, phase separation and, if desired, chromatographic purification of the crude products. Some of the intermediates and end products are obtained in the form of colorless or pale brown, viscous oils which are freed or purified from volatile components under reduced pressure at moderately elevated temperature. If the intermediates and end products are obtained as solids, they may also be purified by recrystallization or digestion.

When the compounds I are prepared, they may be obtained, because of their C=N double bonds, in the form of E/Z isomer mixtures, which can be separated into the individual compounds in the customary manner, eg. by crystallization or chromatography.

If isomer mixtures result from the synthesis, however, a separation is generally not absolutely necessary since, in some cases, the individual isomers may be converted into each other during preparation for use or upon use (eg. when exposed to light, acids or bases). Such conversions may also take place after use, for example in the case of plant treatment in the treated plant or in the harmful fungus or animal pest to be controlled.

With a view to the —$CR^3$=N—N=$CR^4R^5$ double bonds, the cis isomers of the compounds I (configuration based on the radical $R^3$ relative to the —N=$CR^4R^5$ group, or based on the radical $R^4$ relative to the —N=$CR^3$ group) are generally preferred regarding their activity.

The compounds I may contain acidic or basic centers and, accordingly, form acid addition products or base addition products or salts.

Acids for acid addition products are, inter alia, mineral acids (eg. hydrohalic acids such as hydrochloric and hydrobromic acid, phosphoric acid, sulfuric acid, nitric acid), organic acids (eg. formic acid, acetic acid, oxalic acid, malonic acid, lactic acid, malic acid, succinic acid, tartaric acid, citric acid, salicylic acid, p-toluenesulfonic acid, dodecylbenzenesulfonic acid) or other proton-acidic compounds (eg. saccharin).

Bases for base addition products are, inter alia, oxides, hydroxides, carbonates or hydrogen carbonates of alkali metals or alkaline earth metals (eg. potassium hydroxide, potassium carbonate, sodium hydroxide or sodium carbonate) or ammonium compounds (eg. ammonium hydroxide).

In the definitions of the compounds I given at the outset, collective terms were used which generally represent the following groups:

Halogen: fluorine, chlorine, bromine and iodine;

Alkyl: straight-chain or branched alkyl groups having 1 to 10 carbon atoms, eg. $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Alkylamino: an amino group which has attached to it a straight-chain or branched alkyl group having 1 to 6 carbon atoms as mentioned above;

Dialkylamino: an amino group which has attached to it two straight-chain or branched alkyl groups which are independent of one another and which have in each case attached to them 1 to 6 carbon atoms as mentioned above;

Alkylcarbonyl: straight-chain or branched alkyl groups having 1 to 10 carbon atoms which are bonded to the skeleton via a carbonyl group (—CO—);

Alkylsulfonyl: straight-chain or branched alkyl groups having 1 to 10 carbon atoms which are bonded to the skeleton via a sulfonyl group (—SO$_2$—);

Alkylsulfoxyl: straight-chain or branched alkyl groups having 1 to 6 carbon atoms which are bonded to the skeleton via a sulfoxyl group (—S(=O)—);

Alkylaminocarbonyl: alkylamino groups having 1 to 6 carbon atoms as mentioned above which are bonded to the skeleton via a carbonyl group (—CO—);

Dialkylaminocarbonyl: dialkylamino groups having in each case 1 to 6 carbon atoms per alkyl radical as mentioned above which are bonded to the skeleton via a carbonyl group (—CO—);

Alkylaminothiocarbonyl: alkylamino groups having 1 to 6 carbon atoms as mentioned above which are bonded to the skeleton via a thiocarbonyl group (—CS—);

Dialkylaminothiocarbonyl: dialkylamino groups having in each case 1 to 6 carbon atoms per alkyl radical as mentioned above which are bonded to the skeleton via a thiocarbonyl group (—CS—);

Haloalkyl: straight-chain or branched alkyl groups having 1 to 6 carbon atoms, it being possible for some or all of the hydrogen atoms in these groups to be replaced by halogen atoms as mentioned above, eg. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkyl groups having 1 to 6 carbon atoms as mentioned above which are bonded to the skeleton via an oxygen atom (—O—), eg. $C_1$–$C_6$-alkoxy such as methyloxy, ethyloxy, propyloxy, 1-methylethyloxy, butyloxy, 1-methylpropyloxy, 2-methylpropyloxy, 1,1-dimethylethyloxy, pentyloxy, 1-methylbutyloxy, 2-methylbutyloxy, 3-methylbutyloxy, 2,2-dimethylpropyloxy, 1-ethylpropyloxy, hexyloxy, 1,1-dimethylpropyloxy, 1,2-dimethylpropyloxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy and 1-ethyl-2-methylpropyloxy;

Alkoxycarbonyl: straight-chain or branched alkyl groups having 1 to 6 carbon atoms which are bonded to the skeleton via an oxycarbonyl group (—OC(=O)—);

Haloalkoxy: straight-chain or branched alkyl groups having 1 to 6 carbon atoms, it being possible for some or all of the hydrogen atoms in these groups to be replaced by halogen atoms as mentioned above, and these groups being bonded to the skeleton via an oxygen atom;

Alkylthio: straight-chain or branched alkyl groups having 1 to 6 carbon atoms as mentioned above which are bonded to the skeleton via a sulfur atom (—S—), eg. $C_1$–$C_6$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

Cycloalkyl: monocyclic alkyl groups having 3 to 6 carbon ring members, eg. cyclopropyl, cyclobutyl, cyclopentyl and cyclohexyl;

Alkenyl: straight-chain or branched alkenyl groups having 2 to 10 carbon atoms and one double bond in any position, eg. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Alkenyloxy: straight-chain or branched alkenyl groups having 2 to 6 carbon atoms and one double bond in any position which are bonded to the skeleton via an oxygen atom (—O—);

Alkenylthio and alkenylamino: straight-chain or branched alkenyl groups having 2 to 6 carbon atoms and one double bond in any position which are bonded to the skeleton via a sulfur atom (alkenylthio) or a nitrogen atom (alkenylamino);

Alkenylcarbonyl: straight-chain or branched alkenyl groups having 2 to 10 carbon atoms and one double bond in any position which are bonded to the skeleton via a carbonyl group (—CO—);

Alkynyl: straight-chain or branched alkynyl groups having 3 to 10 carbon atoms and one triple bond in any position, eg. $C_3$–$C_6$-alkynyl such as 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

Alkynyloxy, alkynylthio and alkynylamino: straight-chain or branched alkynyl groups having 2 to 6 carbon atoms and one triple bond in any position which are bonded to the skeleton via an oxygen atom (alkynyloxy), via a sulfur atom (alkynylthio) or via a nitrogen atom (alkynylamino);

Alkynylcarbonyl: straight-chain or branched alkynyl groups having 3 to 10 carbon atoms and one triple bond in any position which are bonded to the skeleton via a carbonyl group (—CO—);

Cycloalkenyl, cycloalkenyloxy, cycloalkenylthio and cycloalkenylamino: monocyclic alkenyl groups having 3 to 6 carbon ring members which are bonded to the skeleton directly or via an oxygen atom (cycloalkenyloxy), via a sulfur atom (cycloalkenylthio) or via a nitrogen atom (cycloalkenylamino), eg. cyclobutenyl, cyclopentenyl or cyclohexenyl;

Cycloalkoxy, cycloalkylthio and cycloalkylamino: monocyclic alkyl groups having 3 to 6 carbon ring members which are bonded to the skeleton via an oxygen atom (cycloalkyloxy), via a sulfur atom (cycloalkylthio) or via a nitrogen atom (cycloalkylamino), eg. cyclopropyl, cyclobutyl, cyclopentyl or cyclohexyl;

Heterocyclyl, heterocyclyloxy, heterocyclylthio and heterocyclylamino: three- to six-membered, saturated or partially unsaturated mono- or polycyclic heterocycles which contain one to three hetero atoms selected from a group consisting of oxygen, nitrogen and sulfur and which are bonded to the skeleton directly or via an oxygen atom (heterocyclyloxy), via a sulfur atom (heterocyclylthio) or via a nitrogen atom (heterocyclylamino), eg. 2-tetrahydrofuranyl, oxiranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 5-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,2,4-triazolidin-5-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,3-dihydrofur-4-yl, 2,3-dihydrofur-5-yl, 2,5-dihydrofur-2-yl, 2,5-dihydrofur-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,3-dihydroisothiazol-3-yl, 2,3-dihydroisothiazol-4-yl, 2,3-dihydroisothiazol-5-yl, 4,5-dihydroisothiazol-3-yl, 4,5-dihydroisothiazol-4-yl, 4,5-dihydroisothiazol-5-yl, 2,3-dihydroisothiazol-3-yl, 2,3-dihydroisothiazol-4-yl, 2,3-dihydroisothiazol-5-yl, 2,3-dihydropyrazol-3-yl, 2,3-dihydropyrazol-4-yl, 2,3-dihydropyrazol-5-yl, 4,5-dihydropyrazol-3-yl, 4,5-dihydropyrazol-4-yl, 4,5-dihydropyrazol-5-yl, 2,5-dihydropyrazol-3-yl, 2,5-dihydropyrazol-4-yl, 2,5-dihydropyrazol-5-yl, 2,3-dihydrooxazol-2-yl, 2,3-dihydrooxazol-4-yl, 2,3-dihydrooxazol-5-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 1,3-dioxolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl;

Aryl, aryloxy, arylthio, arylcarbonyl and arylsulfonyl: aromatic mono- or polycyclic hydrocarbon radicals which are bonded to the skeleton directly or via an oxygen atom (—O—; aryloxy), via a sulfur atom (—S—; arylthio), via a carbonyl group (—CO—; arylcarbonyl) or via a sulfonyl group (—SO$_2$—; arylsulfonyl), eg. phenyl, naphthyl and phenanthrenyl, or phenyloxy, naphthyloxy and phenanthrenyloxy and the corresponding carbonyl and sulfonyl radicals;

Arylamino: aromatic mono- or polycyclic hydrocarbon radicals which are bonded to the skeleton via a nitrogen atom;

Hetaryl, hetaryloxy, hetarylthio, hetarylcarbonyl and hetarylsulfonyl: aromatic mono- or polycyclic radicals which, besides carbon ring members, can additionally contain one to four nitrogen atoms, or one to three nitrogen atoms and one oxygen or one sulfur atom, or one oxygen or one sulfur atom, and which are bonded to the skeleton directly or via an oxygen atom (—O—; hetaryloxy), via a sulfur atom (—S—; hetarylthio), via a carbonyl group (—CO—; hetarylcarbonyl) or via a sulfonyl group (—SO$_2$—; hetarylsulfonyl), eg.

5-membered hetaryl containing one to three nitrogen atoms: 5-membered hetaryl ring groups which, besides carbon atoms, can contain one to three nitrogen atoms as ring members, eg. 2-pyrrolyl, 3-pyrrolyl, 3-pyrazolyl, 4-pyrazolyl, 5-pyrazolyl, 2-imidazolyl, 4-imidazolyl, 5-imidazolyl, 1,2,4-triazol-3-yl, 1,2,4-triazol-5-yl, 1,2,3-triazol-4-yl, 1,2,3-triazol-5-yl, 1,3,4-triazol-2-yl and 1,3,4-triazol-5-yl;

5-membered hetaryl containing one to four nitrogen atoms or one to three nitrogen atoms and one sulfur or oxygen atom or one oxygen or one sulfur atom: 5-membered hetaryl ring groups which, besides carbon atoms, can contain one to four nitrogen atoms or one to three nitrogen atoms and one sulfur or oxygen atom, or one oxygen or sulfur atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,2,4-triazol-5-yl, 1,3,4-oxadiazol-2-yl, 1,3,4-oxadiazol-5-yl, 1,3,4-thiadiazol-2-yl, 1,3,4-thiadiazol-5-yl, 1,3,4-triazol-2-yl and 1,3,4-triazol-5-yl;

benzo-fused 5-membered hetaryl containing one to three nitrogen atoms or one nitrogen atom and/or one oxygen or sulfur atom: 5-membered hetaryl ring groups which, besides carbon atoms, can contain one to four nitrogen atoms, or one to three nitrogen atoms and one sulfur or oxygen atom or one oxygen or one sulfur atom as ring members, and in which two adjacent carbon ring members or one nitrogen and one adjacent carbon ring member can be bridged by a buta-1,3-diene-1,4-diyl group;

5-membered hetaryl, bonded via nitrogen and containing one to four nitrogen atoms, or benzo-fused 5-membered hetaryl, bonded via nitrogen and containing one to three nitrogen atoms: 5-membered hetaryl ring groups which, besides carbon atoms, can contain one to four nitrogen atoms, or one to three nitrogen atoms, respectively, as ring members and in which two adjacent carbon ring members or one nitrogen and one adjacent carbon ring member can be bridged by a buta-1,3-diene-1,4-diyl group, these rings being bonded to the skeleton via one of the nitrogen ring members;

6-membered hetaryl containing one to three, or one to four, nitrogen atoms: 6-membered hetaryl ring groups which, besides carbon atoms, can contain one to three, or one to four, nitrogen atoms, respectively, as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 6-membered hetaryl containing one to four nitrogen atoms: 6-membered hetaryl ring groups in which two adjacent carbon ring members can be bridged by a buta-1,3-diene-1,4-diyl group, eg. quinoline, isoquinoline, quinazoline and quinoxaline, and the corresponding oxy, thio, carbonyl or sulfonyl groups.

Hetarylamino: aromatic mono- or polycyclic radicals which, besides carbon ring members, can additionally contain one to four nitrogen atoms or one to three nitrogen atoms and one oxygen or one sulfur atom and which are bonded to the skeleton via a nitrogen atom.

The term "partially or fully halogenated" is used to indicate that some or all of the hydrogen atoms in thus characterized groups can be replaced by identical or different halogen atoms as mentioned above.

The term "substituted or unsubstituted" when referring to the radicals mentioned in the definition of $R^2$ is used to indicate that the groups in question can be partially or fully halogenated and/or can have attached to them one to three of the following groups:

cyano, nitro, hydroxyl, mercapto, amino, carboxyl, aminocarbonyl, aminothiocarbonyl, $C_1$–$C_6$-alkylcarbonyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, C (=NOR$^b$) A$_n$—R$^c$ or benzyloxy and benzylthio which are substituted by customary groups;

$C_3$–$C_6$-cycloalkyl, $C_3$–$C_6$-cycloalkoxy, heterocyclyl, heterocyclyloxy, benzyloxy, aryl, aryloxy, arylthio, hetaryl, hetaryloxy and hetarylthio, it being possible for the cyclic groups, in turn, to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, C(=NOR$^b$)—A$_n$—R$^c$, or benzyl, benzyloxy, aryl, aryloxy, arylthio, hetaryl, hetaryloxy and hetarylthio which are substituted by customary groups.

The term "substituted by customary groups" is used to indicate that the radicals in question can be partially or fully halogenated and/or have attached to them one to three of the following substituents: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylcarbonyl, $C_1$–$C_4$-alkoxycarbonyl, phenyl, phenoxy, benzyl and benzyloxy, and/or can have attached to them a group C(=NOR$^b$)—A$_n$—R$^c$.

Compounds of the formula I which must be emphasized with a view to their biological activity are those where the substituents and the index have the following meanings:

R is cyano, nitro, trifluoromethyl, halogen, $C_1$–$C_4$-alkyl or $C_1$–$C_4$-alkoxy;

m is 0, 1 or 2, it being possible for the radicals R to be different if n is 2;

$R^1$ is alkyl, alkenyl, alkynyl, cycloalkyl or cycloalkenyl, and, in the event that X is NR$^a$, additionally hydrogen;

X is a direct bond, O or NR$^a$;

R$^a$ is hydrogen, alkyl, alkenyl, alkynyl, cycloalkyl or cycloalkenyl;

$R^2$ is hydrogen, unsubstituted or substituted alkyl, alkenyl, alkynyl, cycloalkyl, cycloalkenyl, cycloalkynyl, alkylcarbonyl or alkoxycarbonyl;

$R^3$ and $R^4$ independently of one another are hydrogen, cyano, nitro, hydroxyl, amino, halogen, $C_1$–$C_6$-alkyl, $C_1$–$C_6$-alkoxy, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_2$–$C_6$-alkenylthio, $C_2$–$C_6$-alkenylamino, N—$C_2$–$C_6$-alkenyl-N—$C_1$–$C_6$-alkylamino, $C_2$–$C_6$-alkynyl, $C_2$–$C_6$-alkynyloxy, $C_2$–$C_6$-alkynylthio, $C_2$–$C_6$-alkynylamino, N—$C_2$–$C_6$-alkynyl-N—$C_1$–$C_6$-alkylamino, it being possible for the hydrocarbon radicals of these groups to be partially or fully halogenated and/or to have attached to them one to three of the following radicals:

cyano, nitro, hydroxyl, mercapto, amino, carboxyl, aminocarbonyl, aminothiocarbonyl, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, aryl-$C_1$–$C_4$-alkoxy, arylthio, aryl-$C_1$–$C_4$-alkylthio, hetaryl, hetaryloxy, hetaryl-$C_1$–$C_4$-alkoxy, hetarylthio and hetaryl-$C_1$–$C_4$-alkylthio, it being possible for the cyclic radicals, in turn, to be partially or fully halogenated and/or to have attached to them one to three of the following groups: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio and $C(=NOR^b)$—$A_n$—$R^c$; $C_3$–$C_6$-cycloalkyl, $C_3$–$C_6$-cycloalkyloxy, $C_3$–$C_6$-cycloalkylthio, $C_3$–$C_6$-cycloalkylamino, N—$C_3$–$C_6$-cycloalkyl-N—$C_1$–$C_6$-alkylamino, $C_5$–$C_8$-cycloalkenyl, $C_5$–$C_8$-cycloalkenyloxy, $C_5$–$C_8$-cycloalkenylthio, $C_5$–$C_8$-cycloalkenylamino, N—$C_5$–$C_8$-cycloalkenyl-N—$C_1$–$C_6$-alkylamino, heterocyclyl, heterocyclyloxy, heterocyclylthio, heterocyclylamino, N-heterocyclyl-N—$C_1$–$C_6$-alkylamino, aryl, aryloxy, arylthio, arylamino, N-aryl-N—$C_1$–$C_6$-alkylamino, hetaryl, hetaryloxy, hetarylthio, hetarylamino, N-hetaryl-N—$C_1$–$C_6$-alkylamino, it being possible for the cyclic radicals to be partially or fully halogenated and/or to have attached to them one to three of the following groups:

cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy, $C(=NOR^b)$—$A_n$—$R^c$ or $NR^f$—CO—D—$R^g$;

A is oxygen, sulfur or nitrogen, the nitrogen having attached to it hydrogen or $C_1$–$C_6$-alkyl;

D is a direct bond, oxygen or $NR^h$;

n is 0 or 1;

$R^b$ and $R^c$ independently of one another are hydrogen or $C_1$–$C_6$-alkyl;

$R^f$ is hydrogen, hydroxyl, $C_1$–$C_6$-alkyl, $C_2$–$C_6$-alkenyl, $C_2$–$C_6$-alkynyl, $C_1$–$C_6$-alkoxy, $C_2$–$C_6$-alkenyloxy, $C_2$–$C_6$-alkynyloxy, $C_1$–$C_6$-alkoxy-$C_1$–$C_6$-alkyl, $C_1$–$C_6$-alkoxy-$C_1$–$C_6$-alkoxy and $C_1$–$C_6$-alkoxycarbonyl;

$R^g$, $R^h$ independently of one another are hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl and hetaryl-$C_1$–$C_6$-alkyl;

$R^5$ is one of the groups mentioned under $R^3$, or a group $CR^d=NOR^e$;

$R^d$ is one of the groups mentioned under $R^3$;

$R^e$ is hydrogen, $C_1$–$C_{10}$-alkyl, $C_3$–$C_6$-cycloalkyl, $C_2$–$C_{10}$-alkenyl, $C_2$–$C_{10}$-alkynyl, $C_1$–$C_{10}$-alkylcarbonyl, $C_2$–$C_{10}$-alkenylcarbonyl, $C_2$–$C_{10}$-alkynylcarbonyl or $C_1$–$C_{10}$-alkylsulfonyl, it being possible for these radicals to be partially or fully halogenated and/or to have attached to them one to three of the following groups:

cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, $C_3$–$C_6$-cycloalkyl, $C_3$–$C_6$-cycloalkyloxy, heterocyclyl, heterocyclyloxy, benzyl, benzyloxy, aryl, aryloxy, arylthio, hetaryl, hetaryloxy and hetarylthio, it being possible for the last twelve groups mentioned, in turn, to be partially or fully halogenated and/or to have attached to them one to three of the following groups:

cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio or $C(=NOR^b)$—$A_n$—$R^c$;

aryl, arylcarbonyl, arylsulfonyl, hetaryl, hetarylcarbonyl or hetarylsulfonyl, it being possible for these radicals to be partially or fully halogenated and/or to have attached to them one to three of the following groups:

cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy or $C(=NOR^b)$—$A_n$—$R^c$, and the salts thereof.

Preferred compounds of the formula I with regard to their biological action are those where m is 0 or 1, in particular 0.

In the event that m is not 0, preferred compounds I are those where R is fluorine, chlorine, methyl and trifluoromethyl.

Particularly preferred compounds I are those where X is oxygen.

Furthermore, especially preferred compounds I are those where X is NH.

Equally, especially preferred compounds I are those where X is a direct linkage.

Particularly preferred compounds I are those where $R^1$ is methyl.

Furthermore, especially preferred compounds I are those where $R^1$ is ethyl.

Equally, especially preferred compounds I are those where $R^1$ is cyclopropyl.

Besides, especially preferred compounds I are those where $R^1$ is hydrogen (X is $NR^a$).

Particularly preferred compounds I are those where $R^2$ is hydrogen.

Furthermore, especially preferred compounds I are those where $R^2$ is methyl.

Equally, especially preferred compounds I are those where $R^2$ is ethyl.

Besides, especially preferred compounds I are those where $R^2$ is methoxymethyl, allyl or propargyl.

Particularly preferred compounds I are those where $R^3$ is $C_1$–$C_4$-alkyl, especially methyl.

Furthermore, especially preferred compounds I are those where $R^3$ is aryl, especially substituted or unsubstituted phenyl.

Equally, especially preferred compounds I are those where $R^3$ is hetaryl, especially substituted or unsubstituted isoxazolyl, pyrazolyl and pyridinyl.

Besides, especially preferred compounds I are those where $R^3$ is substituted or unsubstituted cycloalkyl, especially cycloalkyl.

Particularly preferred compounds I are those where $R^4$ is $C_1-C_4$-alkyl, especially methyl.

Furthermore, especially preferred compounds I are those where $R^4$ is aryl, especially substituted or unsubstituted phenyl.

Equally, especially preferred compounds I are those where $R^4$ is substituted or unsubstituted cycloalkyl, especially cycloalkyl.

Besides, especially preferred compounds I are those where $R^4$ is hetaryl, especially substituted or unsubstituted isoxazolyl, pyrazolyl and pyridinyl.

Particularly preferred compounds I are those where $R^5$ is $C_1-C_4$-alkyl.

Furthermore, especially preferred compounds I are those where $R^5$ is aryl, especially substituted or unsubstituted phenyl.

Equally, especially preferred compounds I are those where $R^5$ is hetaryl, especially substituted or unsubstituted isoxazolyl, pyrazolyl and pyridinyl.

Besides, especially preferred compounds I are those where $R^5$ is a group $CR^d$=$NOR^e$.

In the event that $R^5$ is a group $CR^d$=$NOR^e$, preferred compounds I are those where $R^d$ is $C_1-C_4$-alkyl, especially methyl.

Particularly preferred compounds I are those where $R^d$ is aryl, especially substituted or unsubstituted phenyl.

Furthermore, especially preferred compounds I are those where $R^d$ is hetaryl, especially substituted or unsubstituted isoxazolyl, pyrazolyl and pyridinyl.

Equally, especially preferred compounds I are those where $R^d$ is substituted or unsubstituted cycloalkyl, especially cycloalkyl.

Besides, especially preferred compounds I are those where $R^e$ is $C_1-C_4$-alkyl, especially methyl.

Furthermore, especially preferred compounds I are those where $R^e$ is substitute d or unsubstituted alkenyl, especially allyl.

Equally, especially preferred compounds I are those where $R^e$ is substituted or unsubstituted alkynyl, especially propargyl.

Besides, especially preferred compounds I are those where $R^e$ is methoxyethyl.

Particularly preferred compounds I with regard to their use are those compiled in the tables which follow. Furthermore, the groups mentioned in the tables for a substituent are, on their own and independently of the combination in which they are mentioned, an especially preferred embodiment of the substituent in question.

Table 1

Compounds of the general formula IA (m=0) where $XR^1$ is methyl, $R^3$ is methyl and the combination of the substituents $R^4$ and $R^5$ corresponds in each case to one line of Table A

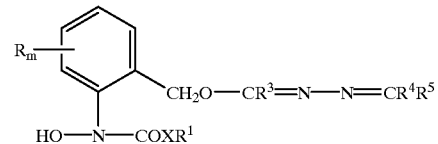

Table 2

Compounds of the general formula IA (m=0) where $XR^1$ is ethyl, $R^3$ is methyl and the combination of the substituents $R^4$ and $R^5$ corresponds in each case to one line of Table A.

Table 3

Compounds of the general formula IA (m=0) where XR1 is methoxy, $R^3$ is methyl and the combination of the substituents $R^4$ and $R^5$ corresponds in each case to one line of Table A.

Table 4

Compounds of the general formula IA (m=0) where $XR^1$ is ethoxy, $R^3$ is methyl and the combination of the substituents $R^4$ and $R^5$ corresponds in each case to one line of Table A.

Table 5

Compounds of the general formula IA (m=0) where $XR^1$ is methylamino, $R^3$ is methyl and the combination of the substituents $R^4$ and $R^5$ corresponds in each case to one line of Table A.

Table 6

Compounds of the general formula IB (m=0) where $XR^1$ is methyl, $R^2$ is methyl, $R^3$ is methyl and the combination of the substituents $R^4$ and $R^5$ corresponds in each case to one line of Table A.

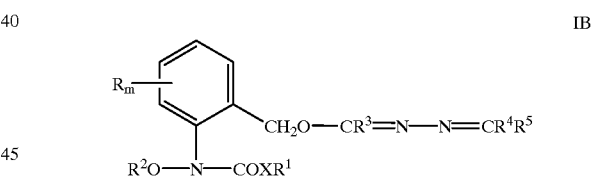

Table 7

Compounds of the general formula IB (m=0) where $XR^1$ is ethyl, $R^2$ is methyl, $R^3$ is methyl and the combination of the substituents $R^4$ and $R^5$ corresponds in each case to one line of Table A.

Table 8

Compounds of the general formula IB (m=0) where $XR^1$ is methoxy, $R^2$ is methyl, $R^3$ is methyl and the combination of the substituents $R^4$ and $R^5$ corresponds in each case to one line of Table A.

Table 9

Compounds of the general formula IB (m=0) where $XR^1$ is ethoxy, $R^2$ is methyl, $R^3$ is methyl and the combination of the substituents $R^4$ and $R^5$ corresponds in each case to one line of Table A.

Table 10

Compounds of the general formula IB (m=0) where $XR^1$ is methylamino, $R^2$ is methyl, $R^3$ is methyl and the combination of the substituents $R^4$ and $R^5$ corresponds in each case to one line of Table A.

Table 11

Compounds of the general formula IB (m=0) where $XR^1$ is methyl, $R^2$ is ethyl, $R^3$ is methyl and the combination of the substituents $R^4$ and $R^5$ corresponds in each case to one line of Table A.

Table 12

Compounds of the general formula IB (m=0) where $XR^1$ is ethyl, $R^2$ is ethyl, $R^3$ is methyl and the combination of the substituents $R^4$ and $R^5$ corresponds in each case to one line of Table A.

Table 13

Compounds of the general formula IB (m=0) where $XR^1$ is methoxy, $R^2$ is ethyl, $R^3$ is methyl and the combination of the substituents $R^4$ and $R^5$ corresponds in each case to one line of Table A.

Table 14

Compounds of the general formula IB (m=0) where $XR^1$ is ethoxy, $R^2$ is ethyl, $R^3$ is methyl and the combination of the substituents $R^4$ and $R^5$ corresponds in each case to one line of Table A.

Table 15

Compounds of the general formula IB (m=0) where $XR^1$ is methylamino, $R^2$ is ethyl, $R^3$ is methyl and the combination of the substituents $R^4$ and $R^5$ corresponds in each case to one line of Table A.

Table 16

Compounds of the general formula IA where $R_m$ is 3-chlorine, $XR^1$ is methyl, $R^3$ is methyl and the combination of the substituents $R^4$ and $R^5$ corresponds in each case to one line of Table A.

Table 17

Compounds of the general formula IA where $R_m$ is 3-chlorine, $XR^1$ is ethyl, $R^3$ is methyl and the combination of the substituents $R^4$ and $R^5$ corresponds in each case to one line of Table A.

Table 18

Compounds of the general formula IA where $R_m$ is 3-chlorine, $XR^1$ is methoxy, $R^3$ is methyl and the combination of the substituents $R^4$ and $R^5$ corresponds in each case to one line of Table A.

Table 19

Compounds of the general formula IA where $R_m$ is 3-chlorine, $XR^1$ is ethoxy, $R^3$ is methyl and the combination of the substituents $R^4$ and $R^5$ corresponds in each case to one line of Table A.

Table 20

Compounds of the general formula IA where $R_m$ is 3-chlorine, $XR^1$ is methylamino, $R^3$ is methyl and the combination of the substituents $R^4$ and $R^5$ corresponds in each case to one line of Table A.

Table 21

Compounds of the general formula IB where $R_m$ is 3-chlorine, $XR^1$ is methyl, $R^2$ is methyl, $R^3$ is methyl and the combination of the substituents $R^4$ and $R^5$ corresponds in each case to one line of Table A.

Table 22

Compounds of the general formula IB where $R_m$ is 3-chlorine, $XR^1$ is ethyl, $R^2$ is methyl, $R^3$ is methyl and the combination of the substituents $R^4$ and $R^5$ corresponds in each case to one line of Table A.

Table 23

Compounds of the general formula IB where $R_m$ is 3-chlorine, $XR^1$ is metoxy, $R^2$ is methyl, $R^3$ is methyl and the combination of the substituents $R^4$ and $R^5$ corresponds in each case to one line of Table A.

Table 24

Compounds of the general formula IB where $R_m$ is 3-chlorine; $XR^1$ is ethoxy, $R^2$ is methyl, $R^3$ is methyl and the combination of the substituents $R^4$ and $R^5$ corresponds in each case to one line of Table A.

Table 25

Compounds of the general formula IB where $R_m$ is 3-chlorine, $XR^1$ is methylamino, $R^2$ is methyl, $R^3$ is methyl and the combination of the substituents $R^4$ and $R^5$ corresponds in each case to one line of Table A.

Table 26

Compounds of the general formula IB where $R_m$ is 3-chlorine, $XR^1$ is methyl, $R^2$ is ethyl, $R^3$ is methyl and the combination of the substituents $R^4$ and $R^5$ corresponds in each case to one line of Table A.

Table 27

Compounds of the general formula IB where $R_m$ is 3-chlorine, $XR^1$ is ethyl, $R^2$ is ethyl, $R^3$ is methyl and the combination of the substituents $R^4$ and $R^5$ corresponds in each case to one line of Table A.

Table 28

Compounds of the general formula IB where $R_m$ is 3-chlorine, $XR^1$ is methoxy, $R^2$ is ethyl, $R^3$ is methyl and the combination of the substituents $R^4$ and $R^5$ corresponds in each case to one line of Table A.

Table 29

Compounds of the general formula IB where $R_m$ is 3-chlorine $XR^1$ is ethoxy, $R^2$ is ethyl, $R^3$ is methyl and the combination of the substituents $R^4$ and $R^5$ corresponds in each case to one line of Table A.

Table 30

Compounds of the general formula IB where $R_m$ is 3-chlorine $XR^1$ is methylamino, $R^2$ is ethyl, $R^3$ is methyl and the combination of the substituents $R^4$ and $R^5$ corresponds in each case to one line of Table A.

Table 31

Compounds of the general formula IA where $R_m$ is 6-methyl, $XR^1$ is methyl, $R^3$ is methyl and the combination of the substituents $R^4$ and $R^5$ corresponds in each case to one line of Table A.

Table 32

Compounds of the general formula IA where $R_m$ is 6-methyl, $XR^1$ is ethyl, $R^3$ is methyl and the combination of the substituents $R^4$ and $R^5$ corresponds in each case to one line of Table A.

Table 33

Compounds of the general formula IA where $R_m$ is 6-methyl, $XR^1$ is methoxy, $R^3$ is methyl and the combination of the substituents $R^4$ and $R^5$ corresponds in each case to one line of Table A.

Table 34

Compounds of the general formula IA where $R_m$ is 6-methyl, $XR^1$ is ethoxy, $R^3$ is methyl and the combination of the substituents $R^4$ and $R^5$ corresponds in each case to one line of Table A.

Table 35

Compounds of the general formula IA where $R_m$ is 6-methyl, $XR^1$ is methylamino, $R^3$ is methyl and the combination of the substituents $R^4$ and $R^5$ corresponds in each case to one line of Table A.

Table 36

Compounds of the general formula IB where $R_m$ is 6-methyl, $XR^1$ is methyl, $R^2$ is methyl, $R^3$ is methyl and the combination of the substituents $R^4$ and $R^5$ corresponds in each case to one line of Table A.

Table 37

Compounds of the general formula IB where $R_m$ is 6-methyl, $XR^1$ is ethyl, $R^2$ is methyl, $R^3$ is methyl and the combination of the substituents $R^4$ and $R^5$ corresponds in each case to one line of Table A.

Table 38

Compounds of the general formula IB where $R_m$ is 6-methyl, $XR^1$ is methoxy, $R^2$ is methyl, $R^3$ is methyl and the combination of the substituents $R^4$ and $R^5$ corresponds in each case to one line of Table A.

Table 39

Compounds of the general formula IB where $R_m$ is 6-methyl, $XR^1$ is ethoxy, $R^2$ is methyl, $R^3$ is methyl and the combination of the substituents $R^4$ and $R^5$ corresponds in each case to one line of Table A.

Table 40

Compounds of the general formula IB where $R_m$ is 6-methyl, $XR^1$ is methylamino, $R^2$ is methyl, $R^3$ is methyl and the combination of the substituents $R^4$ and $R^5$ corresponds in each case to one line of Table A.

Table 41

Compounds of the general formula IB where $R_m$ is 6-methyl, $XR^1$ is methyl, $R^2$ is ethyl, $R^3$ is methyl and the combination of the substituents $R^4$ and $R^5$ corresponds in each case to one line of Table A.

Table 42

Compounds of the general formula IB where $R_m$ is 6-methyl, $XR^1$ is ethyl, $R^2$ is ethyl, $R^3$ is methyl and the combination of the substituents $R^4$ and $R^5$ corresponds in each case to one line of Table A.

Table 43

Compounds of the general formula IB where $R_m$ is 6-methyl, $XR^1$ is methoxy, $R^2$ is ethyl, $R^3$ is methyl and the combination of the substituents $R^4$ and $R^5$ corresponds in each case to one line of Table A.

Table 44

Compounds of the general formula IB where $R_m$ is 6-methyl, $XR^1$ is ethoxy, $R^2$ is ethyl, $R^3$ is methyl and the combination of the substituents $R^4$ and $R^5$ corresponds in each case to one line of Table A.

Table 45

Compounds of the general formula IB where $R_m$ is 6-methyl, $XR^1$ is methylamino, $R^2$ is ethyl, $R^3$ is methyl and the combination of the substituents $R^4$ and $R^5$ corresponds in each case to one line of Table A.

Table 46

Compounds of the general formula IA (m=0) where $XR^1$ is methyl, $R^3$ is methoxy and the combination of the substituents $R^4$ and $R^5$ corresponds in each case to one line of Table A.

Table 47

Compounds of the general formula IA (m=0) where $XR^1$ is ethyl, $R^3$ is methoxy and the combination of the substituents $R^4$ and $R^5$ corresponds in each case to one line of Table A.

Table 48

Compounds of the general formula IA (m=0) where $XR^1$ is methoxy, $R^3$ is methoxy and the combination of the substituents $R^4$ and $R^5$ corresponds in each case to one line of Table A.

Table 49

Compounds of the general formula IA (m=0) where $XR^1$ is ethoxy, $R^3$ is methoxy and the combination of the substituents $R^4$ and $R^5$ corresponds in each case to one line of Table A.

Table 50

Compounds of the general formula IA (m=0) where $XR^1$ is methylamino, $R^3$ is methoxy and the combination of the substituents $R^4$ and $R^5$ corresponds in each case to one line of Table A.

Table 51

Compounds of the general formula IB (m=0) where $XR^1$ is methyl, $R^2$ is methyl, $R^3$ is methoxy and the combination of the substituents $R^4$ and $R^5$ corresponds in each case to one line of Table A.

Table 52

Compounds of the general formula IB (m=0) where $XR^1$ is ethyl, $R^2$ is methyl, $R^3$ is methoxy and the combination of the substituents $R^4$ and $R^5$ corresponds in each case to one line of Table A.

Table 53

Compounds of the general formula IB (m=0) where $XR^1$ is methoxy, $R^2$ is methyl, $R^3$ is methoxy and the combination of the substituents $R^4$ and $R^5$ corresponds in each case to one line of Table A.

Table 54

Compounds of the general formula IB (m=0) where $XR^1$ is ethoxy, $R^2$ is methyl, $R^3$ is methoxy and the combination of the substituents $R^4$ and $R^5$ corresponds in each case to one line of Table A.

Table 55

Compounds of the general formula IB (m=0) where $XR^1$ is methylamino, $R^2$ is methyl, $R^3$ is methoxy and the combination of the substituents $R^4$ and $R^5$ corresponds in each case to one line of Table A.

Table 56

Compounds of the general formula IB (m=0) where $XR^1$ is methyl, $R^2$ is ethyl, $R^3$ is methoxy and the combination of the substituents $R^4$ and $R^5$ corresponds in each case to one line of Table A.

Table 57

Compounds of the general formula IB (m=0) where $XR^1$ is ethyl, $R^2$ is ethyl, $R^3$ is methoxy and the combination of the substituents $R^4$ and $R^5$ corresponds in each case to one line of Table A.

Table 58

Compounds of the general formula IB (m=0) where $XR^1$ is methoxy, $R^2$ is ethyl, $R^3$ is methoxy and the combination of the substituents $R^4$ and $R^5$ corresponds in each case to one line of Table A.

Table 59

Compounds of the general formula IB (m=0) where $XR^1$ is ethoxy, $R^2$ is ethyl, $R^3$ is methoxy and the combination of the substituents $R^4$ and $R^5$ corresponds in each case to one line of Table A.

Table 60

Compounds of the general formula IB (m=0) where $XR^1$ is methylamino, $R^2$ is ethyl, $R^3$ is methoxy and the combination of the substituents $R^4$ and $R^5$ corresponds in each case to one line of Table A.

Table 61

Compounds of the general formula IA where $R_m$ is 3-chlorine, $XR^1$ is methyl, $R^3$ is methoxy and the combination of the substituents $R^4$ and $R^5$ corresponds in each case to one line of Table A.

Table 62

Compounds of the general formula IA where $R_m$ is 3-chlorine, $XR^1$ is ethyl, $R^3$ is methoxy and the combination of the substituents $R^4$ and $R^5$ corresponds in each case to one line of Table A.

Table 63

Compounds of the general formula IA where $R_m$ is 3-chlorine, $XR^1$ is methoxy, $R^3$ is methoxy and the combination of the substituents $R^4$ and $R^5$ corresponds in each case to one line of Table A.

Table 64

Compounds of the general formula IA where $R_m$ is 3-chlorine, $XR^1$ is ethoxy, $R^3$ is methoxy and the combination of the substituents $R^4$ and $R^5$ corresponds in each case to one line of Table A.

Table 65
Compounds of the general formula IA where $R_m$ is 3-chlorine, $XR^1$ is methylamino, $R^3$ is methoxy and the combination of the substituents $R^4$ and $R^5$ corresponds in each case to one line of Table A.

Table 66
Compounds of the general formula IB where $R_m$ is 3-chlorine, $XR^1$ is methyl, $R^2$ is methyl, $R^3$ is methoxy and the combination of the substituents $R^4$ and $R^5$ corresponds in each case to one line of Table A.

Table 67
Compounds of the general formula IB where $R_m$ is 3-chlorine, $XR^1$ is ethyl, $R^2$ is methyl, $R^3$ is methoxy and the combination of the substituents $R^4$ and $R^5$ corresponds in each case to one line of Table A.

Table 68
Compounds of the general formula IB where $R_m$ is 3-chlorine, $XR^1$ is methoxy, $R^2$ is methyl, $R^3$ is methoxy and the combination of the substituents $R^4$ and $R^5$ corresponds in each case to one line of Table A.

Table 69
Compounds of the general formula IB where $R_m$ is 3-chlorine, $XR^1$ is ethoxy, $R^2$ is methyl, $R^3$ is methoxy and the combination of the substituents $R^4$ and $R^5$ corresponds in each case to one line of Table A.

Table 70
Compounds of the general formula IB where $R_m$ is 3-chlorine, $XR^1$ is methylamino, $R^2$ is methyl, $R^3$ is methoxy and the combination of the substituents $R^4$ and $R^5$ corresponds in each case to one line of Table A.

Table 71
Compounds of the general formula IB where $R_m$ is 3-chlorine, $XR^1$ is methyl, $R^2$ is ethyl, $R^3$ is methoxy and the combination of the substituents $R^4$ and $R^5$ corresponds in each case to one line of Table A.

Table 72
Compounds of the general formula IB where $R_m$ is 3-chlorine, $XR^1$ is ethyl, $R^2$ is ethyl, $R^3$ is methoxy and the combination of the substituents $R^4$ and $R^5$ corresponds in each case to one line of Table A.

Table 73
Compounds of the general formula IB where $R_m$ is 3-chlorine, $XR^1$ is methoxy, $R^2$ is ethyl, $R^3$ is methoxy and the combination of the substituents $R^4$ and $R^5$ corresponds in each case to one line of Table A.

Table 74
Compounds of the general formula IB where $R_m$ is 3-chlorine, $XR^1$ is ethoxy, $R^2$ is ethyl, $R^3$ is methoxy and the combination of the substituents $R^4$ and $R^5$ corresponds in each case to one line of Table A.

Table 75
Compounds of the general formula IB where $R_m$ is 3-chlorine, $XR^1$ is methylamino, $R^2$ is ethyl, $R^3$ is methoxy and the combination of the substituents $R^4$ and $R^5$ corresponds in each case to one line of Table A.

Table 76
Compounds of the general formula IA where $R_m$ is 6-methyl, $XR^1$ is methyl, $R^3$ is methoxy and the combination of the substituents $R^4$ and $R^5$ corresponds in each case to one line of Table A.

Table 77
Compounds of the general formula IA where $R_m$ is 6-methyl, $XR^1$ is ethyl, $R^3$ is methoxy and the combination of the substituents $R^4$ and $R^5$ corresponds in each case to one line of Table A.

Table 78
Compounds of the general formula IA where $R_m$ is 6-methyl, $XR^1$ is methoxy, $R^3$ is methoxy and the combination of the substituents $R^4$ and $R^5$ corresponds in each case to one line of Table A.

Table 79
Compounds of the general formula IA where $R_m$ is 6-methyl, $XR^1$ is ethoxy, $R^3$ is methoxy and the combination of the substituents $R^4$ and $R^5$ corresponds in each case to one line of Table A.

Table 80
Compounds of the general formula IA where $R_m$ is 6-methyl, $XR^1$ is methylamino, $R^3$ is methoxy and the combination of the substituents $R^4$ and $R^5$ corresponds in each case to one line of Table A.

Table 81
Compounds of the general formula IB where $R_m$ is 6-methyl, $XR^1$ is methyl, $R^2$ is methyl, $R^3$ is methoxy and the combination of the substituents $R^4$ and $R^5$ corresponds in each case to one line of Table A.

Table 82
Compounds of the general formula IB where $R_m$ is 6-methyl, $XR^1$ is ethyl, $R^2$ is methyl, $R^3$ is methoxy and the combination of the substituents $R^4$ and $R^5$ corresponds in each case to one line of Table A.

Table 83
Compounds of the general formula IB where $R_m$ is 6-methyl, $XR^1$ is methoxy, $R^2$ is methyl, $R^3$ is methoxy and the combination of the substituents $R^4$ and $R^5$ corresponds in each case to one line of Table A.

Table 84
Compounds of the general formula IB where $R_m$ is 6-methyl, $XR^1$ is ethoxy, $R^2$ is methyl, $R^3$ is methoxy and the combination of the substituents $R^4$ and $R^5$ corresponds in each case to one line of Table A.

Table 85
Compounds of the general formula IB where $R_m$ is 6-methyl, $XR^1$ is methylamino, $R^2$ is methyl, $R^3$ is methoxy and the combination of the substituents $R^4$ and $R^5$ corresponds in each case to one line of Table A.

Table 86
Compounds of the general formula IB where $R_m$ is 6-methyl, $XR^1$ is methyl, $R^2$ is ethyl, $R^3$ is methoxy and the combination of the substituents $R^4$ and $R^5$ corresponds in each case to one line of Table A.

Table 87
Compounds of the general formula IB where $R_m$ is 6-methyl, $XR^1$ is ethyl, $R^2$ is ethyl, $R^3$ is methoxy and the combination of the substituents $R^4$ and $R^5$ corresponds in each case to one line of Table A.

Table 88
Compounds of the general formula IB where $R_m$ is 6-methyl, $XR^1$ is methoxy, $R^2$ is ethyl, $R^3$ is methoxy and the combination of the substituents $R^4$ and $R^5$ corresponds in each case to one line of Table A.

Table 89
Compounds of the general formula IB where $R_m$ is 6-methyl, $XR^1$ is ethoxy, $R^2$ is ethyl, $R^3$ is methoxy and the combination of the substituents $R^4$ and $R^5$ corresponds in each case to one line of Table A.

Table 90
Compounds of the general formula IB where $R_m$ is 6-methyl, $XR^1$ is ethylamino, $R^2$ is ethyl, R3 is methoxy and the combination of the substituents $R^4$ and $R^5$ corresponds in each case to one line of Table A.

Table 91
Compounds of the general formula IA (m=0) where $XR^1$ is methyl, $R^3$ is hydroxyl and the combination of the substituents $R^4$ and $R^5$ corresponds in each case to one line of Table A.

Table 92
Compounds of the general formula IA (m=0) where $XR^1$ is ethyl, $R^3$ is hydroxyl and the combination of the substituents $R^4$ and $R^5$ corresponds in each case to one line of Table A.

Table 93
Compounds of the general formula IA (m=0) where $XR^1$ is methoxy, $R^3$ is hydroxyl and the combination of the substituents $R^4$ and $R^5$ corresponds in each case to one line of Table A.

Table 94
Compounds of the general formula IA (m=0) where $XR^1$ is ethoxy, $R^3$ is hydroxyl and the combination of the substituents $R^4$ and $R^5$ corresponds in each case to one line of Table A.

Table 95
Compounds of the general formula IA (m=0) where $XR^1$ is methylamino, $R^3$ is hydroxyl and the combination of the substituents $R^4$ and $R^5$ corresponds in each case to one line of Table A.

Table 96
Compounds of the general formula IB (m=0) where $XR^1$ is methyl, $R^2$ is methyl, $R^3$ is hydroxyl and the combination of the substituents $R^4$ and $R^5$ corresponds in each case to one line of Table A.

Table 97
Compounds of the general formula IB (m=0) where $XR^1$ is ethyl, $R^2$ is methyl, $R^3$ is hydroxyl and the combination of the substituents $R^4$ and $R^5$ corresponds in each case to one line of Table A.

Table 98
Compounds of the general formula IB (m=0) where $XR^1$ is methoxy, $R^2$ is methyl, $R^3$ is hydroxyl and the combination of the substituents $R^4$ and $R^5$ corresponds in each case to one line of Table A.

Table 99
Compounds of the general formula IB (m=0) where $XR^1$ is ethoxy, $R^2$ is methyl, $R^3$ is hydroxyl and the combination of the substituents $R^4$ and $R^5$ corresponds in each case to one line of Table A.

Table 100
Compounds of the general formula IB (m=0) where $XR^1$ is methylamino, $R^2$ is methyl, $R^3$ is hydroxyl and the combination of the substituents $R^4$ and $R^5$ corresponds in each case to one line of Table A.

Table 101
Compounds of the general formula IB (m=0) where $XR^1$ is methyl, $R^2$ is ethyl, $R^3$ is hydroxyl and the combination of the substituents $R^4$ and $R^5$ corresponds in each case to one line of Table A.

Table 102
Compounds of the general formula IB (m=0) where $XR^1$ is ethyl, $R^2$ is ethyl, $R^3$ is hydroxyl and the combination of the substituents $R^4$ and $R^5$ corresponds in each case to one line of Table A.

Table 103
Compounds of the general formula IB (m=0) where $XR^1$ is methoxy, $R^2$ is ethyl, $R^3$ is hydroxyl and the combination of the substituents $R^4$ and $R^5$ corresponds in each case to one line of Table A.

Table 104
Compounds of the general formula IB (m=0) where $XR^1$ is ethoxy, $R^2$ is ethyl, $R^3$ is hydroxyl and the combination of the substituents $R^4$ and $R^5$ corresponds in each case to one line of Table A.

Table 105
Compounds of the general formula IB (m=0) where $XR^1$ is methylamino, $R^2$ is ethyl, $R^3$ is hydroxyl and the combination of the substituents $R^4$ and $R^5$ corresponds in each case to one line of Table A.

Table 106
Compounds of the general formula IA where $R_m$ is 3-chlorine, $XR^1$ is methyl, $R^3$ is hydroxyl and the combination of the substituents $R^4$ and $R^5$ corresponds in each case to one line of Table A.

Table 107
Compounds of the general formula IA where $R_m$ is 3-chlorine, $XR^1$ is ethyl, $R^3$ is hydroxyl and the combination of the substituents $R^4$ and $R^5$ corresponds in each case to one line of Table A.

Table 108
Compounds of the general formula IA where $R_m$ is 3-chlorine, $XR^1$ is methoxy, $R^3$ is hydroxyl and the combination of the substituents $R^4$ and $R^5$ corresponds in each case to one line of Table A.

Table 109
Compounds of the general formula IA where $R_m$ is 3-chlorine, $XR^1$ is ethoxy, $R^3$ is hydroxyl and the combination of the substituents $R^4$ and $R^5$ corresponds in each case to one line of Table A.

Table 110
Compounds of the general formula IA where $R_m$ is 3-chlorine, $XR^1$ is methylamino, $R^3$ is hydroxyl and the combination of the substituents $R^4$ and $R^5$ corresponds in each case to one line of Table A.

Table 111
Compounds of the general formula IB where $R_m$ is 3-chlorine, $XR^1$ is methyl, $R^2$ is methyl, $R^3$ is hydroxyl and the combination of the substituents $R^4$ and $R^5$ corresponds in each case to one line of Table A.

Table 112
Compounds of the general formula IB where $R_m$ is 3-chlorine, $XR^1$ is ethyl, $R^2$ is methyl, $R^3$ is hydroxyl and the combination of the substituents $R^4$ and $R^5$ corresponds in each case to one line of Table A.

Table 113
Compounds of the general formula IB where $R_m$ is 3-chlorine, $XR^1$ is methoxy, $R^2$ is methyl, $R^3$ is hydroxyl and the combination of the substituents $R^4$ and $R^5$ corresponds in each case to one line of Table A.

Table 114
Compounds of the general formula IB where $R_m$ is 3-chlorine, $XR^1$ is ethoxy, $R^2$ is methyl, $R^3$ is hydroxyl and the combination of the substituents $R^4$ and $R^5$ corresponds in each case to one line of Table A.

Table 115
Compounds of the general formula IB where $R_m$ is 3-chlorine, $XR^1$ is methylamino, $R^2$ is methyl, $R^3$ is hydroxyl and the combination of the substituents $R^4$ and $R^5$ corresponds in each case to one line of Table A.

Table 116
Compounds of the general formula IB where $R_m$ is 3-chlorine, $XR^1$ is methyl, $R^2$ is ethyl, $R^3$ is hydroxyl and the combination of the substituents $R^4$ and $R^5$ corresponds in each case to one line of Table A.

Table 117
Compounds of the general formula IB where $R_m$ is 3-chlorine, $XR^1$ is ethyl, $R^2$ is ethyl, $R^3$ is hydroxyl and the combination of the substituents $R^4$ and $R^5$ corresponds in each case to one line of Table A.

Table 118
Compounds of the general formula IB where $R_m$ is 3-chlorine, $XR^1$ is methoxy, $R^2$ is ethyl, $R^3$ is hydroxyl and the combination of the substituents $R^4$ and $R^5$ corresponds in each case to one line of Table A.

Table 119
Compounds of the general formula IB where $R_m$ is 3-chlorine, $XR^1$ is ethoxy, $R^2$ is ethyl, $R^3$ is hydroxyl and the combination of the substituents $R^4$ and $R^5$ corresponds in each case to one line of Table A.

Table 120
Compounds of the general formula IB where $R_m$ is 3-chlorine, $XR^1$ is methylamino, $R^2$ is ethyl, $R^3$ is hydroxyl and the combination of the substituents $R^4$ and $R^5$ corresponds in each case to one line of Table A.

Table 121
Compounds of the general formula IA where $R_m$ is 6-methyl, $XR^1$ is methyl, $R^3$ is hydroxyl and the combination of the substituents $R^4$ and $R^5$ corresponds in each case to one line of Table A.

Table 122
Compounds of the general formula IA where $R_m$ is 6-methyl, $XR^1$ is ethyl, $R^3$ is hydroxyl and the combination of the substituents $R^4$ and $R^5$ corresponds in each case to one line of Table A.

Table 123
Compounds of the general formula IA where $R_m$ is 6-methyl, $XR^1$ is methoxy, $R^3$ is hydroxyl and the combination of the substituents $R^4$ and $R^5$ corresponds in each case to one line of Table A.

Table 124
Compounds of the general formula IA where $R_m$ is 6-methyl, $XR^1$ is ethoxy, $R^3$ is hydroxyl and the combination of the substituents $R^4$ and $R^5$ corresponds in each case to one line of Table A.

Table 125
Compounds of the general formula IA where $R_m$ is 6-methyl, $XR^1$ is methylamino, $R^3$ is hydroxyl and the combination of the substituents $R^4$ and $R^5$ corresponds in each case to one line of Table A.

Table 126
Compounds of the general formula IB where $R_m$ is 6-methyl, $XR^1$ is methyl, $R^2$ is methyl, $R^3$ is hydroxyl and the combination of the substituents $R^4$ and $R^5$ corresponds in each case to one line of Table A.

Table 127
Compounds of the general formula IB where $R_m$ is 6-methyl, $XR^1$ is ethyl, $R^2$ is methyl, $R^3$ is hydroxyl and the combination of the substituents $R^4$ and $R^5$ corresponds in each case to one line of Table A.

Table 128
Compounds of the general formula IB where $R_m$ is 6-methyl, $XR^1$ is methoxy, $R^2$ is methyl, $R^3$ is hydroxyl and the combination of the substituents $R^4$ and $R^5$ corresponds in each case to one line of Table A.

Table 129
Compounds of the general formula IB where $R_m$ is 6-methyl, $XR^1$ is ethoxy, $R^2$ is methyl, $R^3$ is hydroxyl and the combination of the substituents $R^4$ and $R^5$ corresponds in each case to one line of Table A.

Table 130
Compounds of the general formula IB where $R_m$ is 6-methyl, $XR^1$ is methylamino, $R^2$ is methyl, $R^3$ is hydroxyl and the combination of the substituents $R^4$ and $R^5$ corresponds in each case to one line of Table A.

Table 131
Compounds of the general formula IB where $R_m$ is 6-methyl, $XR^1$ is methyl, $R^2$ is ethyl, $R^3$ is hydroxyl and the combination of the substituents $R^4$ and $R^5$ corresponds in each case to one line of Table A.

Table 132
Compounds of the general formula IB where $R_m$ is 6-methyl, $XR^1$ is ethyl, $R^2$ is ethyl, $R^3$ is hydroxyl and the combination of the substituents $R^4$ and $R^5$ corresponds in each case to one line of Table A.

Table 133
Compounds of the general formula IB where $R_m$ is 6-methyl, $XR^1$ is methoxy, $R^2$ is ethyl, $R^3$ is hydroxyl and the combination of the substituents $R^4$ and $R^5$ corresponds in each case to one line of Table A.

Table 134
Compounds of the general formula IB where $R_m$ is 6-methyl, $XR^1$ is ethoxy, $R^2$ is ethyl, $R^3$ is hydroxyl and the combination of the substituents $R^4$ and $R^5$ corresponds in each case to one line of Table A.

Table 135
Compounds of the general formula IB where $R_m$ is 6-methyl, $XR^1$ is methylamino, $R^2$ is ethyl, $R^3$ is hydroxyl and the combination of the substituents $R^4$ and $R^5$ corresponds in each case to one line of Table A.

Table 136
Compounds of the general formula IA (m=0) where $XR^1$ is methyl, $R^3$ is hydrogen and the combination of the substituents $R^4$ and $R^5$ corresponds in each case to one line of Table A.

Table 137
Compounds of the general formula IA (m=0) where $XR^1$ is ethyl, $R^3$ is hydrogen and the combination of the substituents $R^4$ and $R^5$ corresponds in each case to one line of Table A.

Table 138
Compounds of the general formula IA (m=0) where $XR^1$ is methoxy, $R^3$ is hydrogen and the combination of the substituents $R^4$ and $R^5$ corresponds in each case to one line of Table A.

Table 139
Compounds of the general formula IA (m=0) where $XR^1$ is ethoxy, $R^3$ is hydrogen and the combination of the substituents $R^4$ and $R^5$ corresponds in each case to one line of Table A.

Table 140
Compounds of the general formula IA (m=0) where $XR^1$ is methylamino, $R^3$ is hydrogen and the combination of the substituents $R^4$ and $R^5$ corresponds in each case to one line of Table A.

Table 141
Compounds of the general formula IB (m=0) where $XR^1$ is methyl, $R^2$ is methyl, $R^3$ is hydrogen and the combination of the substituents $R^4$ and $R^5$ corresponds in each case to one line of Table A.

Table 142
Compounds of the general formula IB (m=0) where $XR^1$ is ethyl, $R^2$ is methyl, $R^3$ is hydrogen and the combination of the substituents $R^4$ and R5 corresponds in each case to one line of Table A.

Table 143
Compounds of the general formula IB (m=0) where $XR^1$ is methoxy, $R^2$ is methyl, $R^3$ is hydrogen and the combination of the substituents $R^4$ and $R^5$ corresponds in each case to one line of Table A.

Table 144
Compounds of the general formula IB (m=0) where $XR^1$ is ethoxy, $R^2$ is methyl, $R^3$ is hydrogen and the combination of the substituents $R^4$ and $R^5$ corresponds in each case to one line of Table A.

Table 145
Compounds of the general formula IB (m=0) where $XR^1$ is methylamino, $R^2$ is methyl, $R^3$ is hydrogen and the combination of the substituents $R^4$ and $R^5$ corresponds in each case to one line of Table A.

Table 146

Compounds of the general formula IB (m=0) where $XR^1$ is methyl, $R^2$ is ethyl, $R^3$ is hydrogen and the combination of the substituents $R^4$ and $R^5$ corresponds in each case to one line of Table A.

Table 147

Compounds of the general formula IB (m=0) where $XR^1$ is ethyl, $R^2$ is ethyl, $R^3$ is hydrogen and the combination of the substituents $R^4$ and $R^5$ corresponds in each case to one line of Table A.

Table 148

Compounds of the general formula IB (m=0) where $XR^1$ is methoxy, $R^2$ is ethyl, $R^3$ is hydrogen and the combination of the substituents $R^4$ and $R^5$ corresponds in each case to one line of Table A.

Table 149

Compounds of the general formula IB (m=0) where $XR^1$ is ethoxy, $R^2$ is ethyl, $R^3$ is hydrogen and the combination of the substituents $R^4$ and $R^5$ corresponds in each case to one line of Table A.

Table 150

Compounds of the general formula IB (m=0) where $XR^1$ is methylamino, $R^2$ is ethyl, $R^3$ is hydrogen and the combination of the substituents $R^4$ and $R^5$ corresponds in each case to one line of Table A.

Table 151

Compounds of the general formula IA where $R_m$ is 3-chlorine, $XR^1$ is methyl, $R^3$ is hydrogen and the combination of the substituents $R^4$ and $R^5$ corresponds in each case to one line of Table A.

Table 152

Compounds of the general formula IA where $R_m$ is 3-chlorine, $XR^1$ is ethyl, $R^3$ is hydrogen and the combination of the substituents $R^4$ and $R^5$ corresponds in each case to one line of Table A.

Table 153

Compounds of the general formula IA where $R_m$ is 3-chlorine, $XR^1$ is methoxy, $R^3$ is hydrogen and the combination of the substituents $R^4$ and $R^5$ corresponds in each case to one line of Table A.

Table 154

Compounds of the general formula IA where $R_m$ is 3-chlorine, $XR^1$ is ethoxy, $R^3$ is hydrogen and the combination of the substituents $R^4$ and $R^5$ corresponds in each case to one line of Table A.

Table 155

Compounds of the general formula IA where $R_m$ is 3-chlorine, $XR^1$ is methylamino, $R^3$ is hydrogen and the combination of the substituents $R^4$ and $R^5$ corresponds in each case to one line of Table A.

Table 156

Compounds of the general formula IB where $R_m$ is 3-chlorine, $XR^1$ is methyl, $R^2$ is methyl, $R^3$ is hydrogen and the combination of the substituents $R^4$ and $R^5$ corresponds in each case to one line of Table A.

Table 157

Compounds of the general formula IB where $R_m$ is 3-chlorine, $XR^1$ is ethyl, $R^2$ is methyl, $R^3$ is hydrogen and the combination of the substituents $R^4$ and $R^5$ corresponds in each case to one line of Table A.

Table 158

Compounds of the general formula IB where $R_m$ is 3-chlorine, $XR^1$ is methoxy, $R^2$ is methyl, $R^3$ is hydrogen and the combination of the substituents $R^4$ and $R^5$ corresponds in each case to one line of Table A.

Table 159

Compounds of the general formula IB where $R_m$ is 3-chlorine, $XR^1$ is ethoxy, $R^2$ is methyl, $R^3$ is hydrogen and the combination of the substituents $R^4$ and $R^5$ corresponds in each case to one line of Table A.

Table 160

Compounds of the general formula IB where $R_m$ is 3-chlorine, $XR^1$ is methylamino, $R^2$ is methyl, $R^3$ is hydrogen and the combination of the substituents $R^4$ and $R^5$ corresponds in each case to one line of Table A.

Table 161

Compounds of the general formula IB where $R_m$ is 3-chlorine, $XR^1$ is methyl, $R^2$ is ethyl, $R^3$ is hydrogen and the combination of the substituents $R^4$ and $R^5$ corresponds in each case to one line of Table A.

Table 162

Compounds of the general formula IB where $R_m$ is 3-chlorine, $XR^1$ is ethyl, $R^2$ is ethyl, $R^3$ is hydrogen and the combination of the substituents $R^4$ and $R^5$ corresponds in each case to one line of Table A.

Table 163

Compounds of the general formula IB where $R_m$ is 3-chlorine, $XR^1$ is methoxy, $R^2$ is ethyl, $R^3$ is hydrogen and the combination of the substituents $R^4$ and $R^5$ corresponds in each case to one line of Table A.

Table 164

Compounds of the general formula IB where $R_m$ is 3-chlorine, $XR^1$ is ethoxy, $R^2$ is ethyl, $R^3$ is hydrogen and the combination of the substituents $R^4$ and $R^5$ corresponds in each case to one line of Table A.

Table 165

Compounds of the general formula IB where $R_m$ is 3-chlorine, $XR^1$ is methylamino, $R^2$ is ethyl, $R^3$ is hydrogen and the combination of the substituents $R^4$ and $R^5$ corresponds in each case to one line of Table A.

Table 166

Compounds of the general formula IA where $R_m$ is 6-methyl, $XR^1$ is ethyl, $R^3$ is hydrogen and the combination of the substituents $R^4$ and $R^5$ corresponds in each case to one line of Table A.

Table 167

Compounds of the general formula IA where $R_m$ is 6-methyl, $XR^1$ is ethyl, $R^3$ is hydrogen and the combination of the substituents $R^4$ and $R^5$ corresponds in each case to one line of Table A.

Table 168

Compounds of the general formula IA where $R_m$ is 6-methyl, $XR^1$ is methoxy, $R^3$ is hydrogen and the combination of the substituents $R^4$ and $R^5$ corresponds in each case to one line of Table A.

Table 169

Compounds of the general formula IA where $R_m$ is 6-methyl, $XR^1$ is ethoxy, $R^3$ is hydrogen and the combination of the substituents $R^4$ and $R^5$ corresponds in each case to one line of Table A.

Table 170

Compounds of the general formula IA where $R_m$ is 6-methyl, $XR^1$ is methylamino, $R^3$ is hydrogen and the combination of the substituents $R^4$ and $R^5$ corresponds in each case to one line of Table A.

Table 171

Compounds of the general formula IB where $R_m$ is 6-methyl, $XR^1$ is methyl, $R^2$ is methyl, $R^3$ is hydrogen and the combination of the substituents $R^4$ and $R^5$ corresponds in each case to one line of Table A.

Table 172

Compounds of the general formula IB where $R_m$ is 6-methyl, $XR^1$ is ethyl, $R^2$ is methyl, $R^3$ is hydrogen and the combination of the substituents $R^4$ and $R^5$ corresponds in each case to one line of Table A.

Table 173
Compounds of the general formula IB where $R_m$ is 6-methyl, $XR^1$ is methoxy, $R^2$ is methyl, $R^3$ is hydrogen and the combination of the substituents $R^4$ and $R^5$ corresponds in each case to one line of Table A.

Table 174
Compounds of the general formula IB where $R_m$ is 6-methyl, $XR^1$ is ethoxy, $R^2$ is methyl, $R^3$ is hydrogen and the combination of the substituents $R^4$ and $R^5$ corresponds in each case to one line of Table A.

Table 175
Compounds of the general formula IB where $R_m$ is 6-methyl, $XR^1$ is methylamino, $R^2$ is methyl, $R^3$ is hydrogen and the combination of the substituents $R^4$ and $R^5$ corresponds in each case to one line of Table A.

Table 176
Compounds of the general formula IB where $R_m$ is 6-methyl, $XR^1$ is ethyl, $R^2$ is ethyl, $R^3$ is hydrogen and the combination of the substituents $R^4$ and $R^5$ corresponds in each case to one line of Table A.

Table 177
Compounds of the general formula IB where $R_m$ is 6-methyl, $XR^1$ is ethyl, $R^2$ is ethyl, $R^3$ is hydrogen and the combination of the substituents $R^4$ and $R^5$ corresponds in each case to one line of Table A.

Table 178
Compounds of the general formula IB where $R_m$ is 6-methyl, $XR^1$ is methoxy, $R^2$ is ethyl, $R^3$ is hydrogen and the combination of the substituents $R^4$ and $R^5$ corresponds in each case to one line of Table A.

Table 179
Compounds of the general formula IB where $R_m$ is 6-methyl, $XR^1$ is ethoxy, $R^2$ is ethyl, $R^3$ is hydrogen and the combination of the substituents $R^4$ and $R^5$ corresponds in each case to one line of Table A.

Table 180
Compounds of the general formula IB where $R_m$ is 6-methyl, $XR^1$ is methylamino, $R^2$ is ethyl, $R^3$ is hydrogen and the combination of the substituents $R^4$ and $R^5$ corresponds in each case to one line of Table A.

Table 181
Compounds of the general formula IA (m=0) where $XR^1$ is methyl, $R^3$ is chlorine and the combination of the substituents $R^4$ and $R^5$ corresponds in each case to one line of Table A.

Table 182
Compounds of the general formula IA (m=0) where $XR^1$ is ethyl, $R^3$ is chlorine and the combination of the substituents $R^4$ and $R^5$ corresponds in each case to one line of Table A.

Table 183
Compounds of the general formula IA (m=0) where $XR^1$ is methoxy, $R^3$ is chlorine and the combination of the substituents $R^4$ and $R^5$ corresponds in each case to one line of Table A.

Table 184
Compounds of the general formula IA (m=0) where $XR^1$ is ethoxy, $R^3$ is chlorine and the combination of the substituents $R^4$ and $R^5$ corresponds in each case to one line of Table A.

Table 185
Compounds of the general formula IA (m=0) where $XR^1$ is methylamino, $R^3$ is chlorine and the combination of the substituents $R^4$ and $R^5$ corresponds in each case to one line of Table A.

Table 186
Compounds of the general formula IB (m=0) where $XR^1$ is methyl, $R^2$ is methyl, $R^3$ is chlorine and the combination of the substituents $R^4$ and $R^5$ corresponds in each case to one line of Table A.

Table 187
Compounds of the general formula IB (m=0) where $XR^1$ is ethyl, $R^2$ is methyl, $R^3$ is chlorine and the combination of the substituents $R^4$ and $R^5$ corresponds in each case to one line of Table A.

Table 188
Compounds of the general formula IB (m=0) where $XR^1$ is methoxy, $R^2$ is methyl, $R^3$ is chlorine and the combination of the substituents $R^4$ and $R^5$ corresponds in each case to one line of Table A.

Table 189
Compounds of the general formula IB (m=0) where $XR^1$ is ethoxy, $R^2$ is methyl, $R^3$ is chlorine and the combination of the substituents $R^4$ and $R^5$ corresponds in each case to one line of Table A.

Table 190
Compounds of the general formula IB (m=0) where XR1 is methylamino, $R^2$ is methyl, $R^3$ is chlorine and the combination of the substituents $R^4$ and $R^5$ corresponds in each case to one line of Table A.

Table 191
Compounds of the general formula IB (m=0) where $XR^1$ is methyl, $R^2$ is ethyl, $R^3$ is chlorine and the combination of the substituents $R^4$ and $R^5$ corresponds in each case to one line of Table A.

Table 192
Compounds of the general formula IB (m=0) where $XR^1$ is ethyl, $R^2$ is ethyl, $R^3$ is chlorine and the combination of the substituents $R^4$ and $R^5$ corresponds in each case to one line of Table A.

Table 193
Compounds of the general formula IB (m=0) where $XR^1$ is methoxy, $R^2$ is ethyl, $R^3$ is chlorine and the combination of the substituents $R^4$ and $R^5$ corresponds in each case to one line of Table A.

Table 194
Compounds of the general formula IB (m=0) where $XR^1$ is ethoxy, $R^2$ is ethyl, $R^3$ is chlorine and the combination of the substituents $R^4$ and $R^5$ corresponds in each case to one line of Table A.

Table 195
Compounds of the general formula IB (m=0) where $XR^1$ is methylamino, $R^2$ is ethyl, $R^3$ is chlorine and the combination of the substituents $R^4$ and $R^5$ corresponds in each case to one line of Table A.

Table 196
Compounds of the general formula IA where $R_m$ is 3-chlorine, $XR^1$ is methyl, $R^3$ is chlorine and the combination of the substituents $R^4$ and $R^5$ corresponds in each case to one line of Table A.

Table 197
Compounds of the general formula IA where $R_m$ is 3-chlorine, XR1 is ethyl, $R^3$ is chlorine and the combination of the substituents $R^4$ and $R^5$ corresponds in each case to one line of Table A.

Table 198
Compounds of the general formula IA where $R_m$ is 3-chlorine, $XR^1$ is methoxy, $R^3$ is chlorine and the combination of the substituents $R^4$ and $R^5$ corresponds in each case to one line of Table A.

Table 199
Compounds of the general formula IA where $R_m$ is 3-chlorine, $XR^1$ is ethoxy, $R^3$ is chlorine and the combination of the substituents $R^4$ and $R^5$ corresponds in each case to one line of Table A.

Table 200
Compounds of the general formula IA where $R_m$ is 3-chlorine, $XR^1$ is methylamino, $R^3$ is chlorine and the combination of the substituents $R^4$ and $R^5$ corresponds in each case to one line of Table A.

Table 201
Compounds of the general formula IB where $R_m$ is 3-chlorine, $XR^1$ is methyl, $R^2$ is methyl, $R^3$ is chlorine and the combination of the substituents $R^4$ and $R^5$ corresponds in each case to one line of Table A.

Table 202
Compounds of the general formula IB where $R_m$ is 3-chlorine, $XR^1$ is ethyl, $R^2$ is methyl, $R^3$ is chlorine and the combination of the substituents $R^4$ and $R^5$ corresponds in each case to one line of Table A.

Table 203
Compounds of the general formula IB where $R_m$ is 3-chlorine, $XR^1$ is methoxy, $R^2$ is methyl, $R^3$ is chlorine and the combination of the substituents $R^4$ and $R^5$ corresponds in each case to one line of Table A.

Table 204
Compounds of the general formula IB where $R_m$ is 3-chlorine, $XR^1$ is ethoxy, $R^2$ is methyl, $R^3$ is chlorine and the combination of the substituents $R^4$ and $R^5$ corresponds in each case to one line of Table A.

Table 205
Compounds of the general formula IB where $R_m$ is 3-chlorine, $XR^1$ is methylamino, $R^2$ is methyl, $R^3$ is chlorine and the combination of the substituents $R^4$ and $R^5$ corresponds in each case to one line of Table A.

Table 206
Compounds of the general formula IB where $R_m$ is 3-chlorine, $XR^1$ is methyl, $R^2$ is ethyl, $R^3$ is chlorine and the combination of the substituents $R^4$ and $R^5$ corresponds in each case to one line of Table A.

Table 207
Compounds of the general formula IB where $R_m$ is 3-chlorine, $XR^1$ is ethyl, $R^2$ is ethyl, $R^3$ is chlorine and the combination of the substituents $R^4$ and $R^5$ corresponds in each case to one line of Table A.

Table 208
Compounds of the general formula IB where $R_m$ is 3-chlorine, $XR^1$ is methoxy, $R^2$ is ethyl, $R^3$ is chlorine and the combination of the substituents $R^4$ and $R^5$ corresponds in each case to one line of Table A.

Table 209
Compounds of the general formula IB where $R_m$ is 3-chlorine, $XR^1$ is ethoxy, $R^2$ is ethyl, $R^3$ is chlorine and the combination of the substituents $R^4$ and $R^5$ corresponds in each case to one line of Table A.

Table 210
Compounds of the general formula IB where $R_m$ is 3-chlorine, $XR^1$ is ethylamino, $R^2$ is ethyl, $R^3$ is chlorine and the combination of the substituents $R^4$ and $R^5$ corresponds in each case to one line of Table A.

Table 211
Compounds of the general formula IA where $R_m$ is 6-methyl, $XR^1$ is methyl, $R^3$ is chlorine and the combination of the substituents $R^4$ and $R^5$ corresponds in each case to one line of Table A.

Table 212
Compounds of the general formula IA where $R_m$ is 6-methyl, $XR^1$ is ethyl, $R^3$ is chlorine and the combination of the substituents $R^4$ and $R^5$ corresponds in each case to one line of Table A.

Table 213
Compounds of the general formula IA where $R_m$ is 6-methyl, $XR^1$ is methoxy, $R^3$ is chlorine and the combination of the substituents $R^4$ and $R^5$ corresponds in each case to one line of Table A.

Table 214
Compounds of the general formula IA where $R_m$ is 6-methyl, $XR^1$ is ethoxy, $R^3$ is chlorine and the combination of the substituents $R^4$ and $R^5$ corresponds in each case to one line of Table A.

Table 215
Compounds of the general formula IA where $R_m$ is 6-methyl, $XR^1$ is methylamino, $R^3$ is chlorine and the combination of the substituents $R^4$ and $R^5$ corresponds in each case to one line of Table A.

Table 216
Compounds of the general formula IB where $R_m$ is 6-methyl, $XR^1$ is methyl, $R^2$ is methyl, $R^3$ is chlorine and the combination of the substituents $R^4$ and $R^5$ corresponds in each case to one line of Table A.

Table 217
Compounds of the general formula IB where $R_m$ is 6-methyl, $XR^1$ is ethyl, $R^2$ is methyl, $R^3$ is chlorine and the combination of the substituents $R^4$ and $R^5$ corresponds in each case to one line of Table A.

Table 218
Compounds of the general formula IB where $R_m$ is 6-methyl, $XR^1$ is methoxy, $R^2$ is methyl, $R^3$ is chlorine and the combination of the substituents $R^4$ and $R^5$ corresponds in each case to one line of Table A.

Table 219
Compounds of the general formula IB where $R_m$ is 6-methyl, $XR^1$ is ethoxy, $R^2$ is methyl, $R^3$ is chlorine and the combination of the substituents $R^4$ and $R^5$ corresponds in each case to one line of Table A.

Table 220
Compounds of the general formula IB where $R_m$ is 6-methyl, $XR^1$ is methylamino, $R^2$ is methyl, $R^3$ is chlorine and the combination of the substituents $R^4$ and $R^5$ corresponds in each case to one line of Table A.

Table 221
Compounds of the general formula IB where $R_m$ is 6-methyl, $XR^1$ is methyl, $R^2$ is ethyl, $R^3$ is chlorine and the combination of the substituents $R^4$ and $R^5$ corresponds in each case to one line of Table A.

Table 222
Compounds of the general formula IB where $R_m$ is 6-methyl, $XR^1$ is ethyl, $R^2$ is ethyl, $R^3$ is chlorine and the combination of the substituents $R^4$ and $R^5$ corresponds in each case to one line of Table A.

Table 223
Compounds of the general formula IB where $R_m$ is 6-methyl, $XR^1$ is methoxy, $R^2$ is ethyl, $R^3$ is chlorine and the combination of the substituents $R^4$ and $R^5$ corresponds in each case to one line of Table A.

Table 224
Compounds of the general formula IB where $R_m$ is 6-methyl, $XR^1$ is ethoxy, $R^2$ is ethyl, $R^3$ is chlorine and the combination of the substituents $R^4$ and $R^5$ corresponds in each case to one line of Table A.

Table 225
Compounds of the general formula IB where $R_m$ is 6-methyl, $XR^1$ is methylamino, $R^2$ is ethyl, $R^3$ is chlorine and the combination of the substituents $R^4$ and $R^5$ corresponds in each case to one line of Table A.

Table 226
Compounds of the general formula IA (m=0) where $XR^1$ is methyl, $R^3$ is methylthio and the combination of the substituents $R^4$ and $R^5$ corresponds in each case to one line of Table A.

Table 227
Compounds of the general formula IA (m=0) where $XR^1$ is ethyl, $R^3$ is methylthio and the combination of the substituents $R^4$ and $R^5$ corresponds in each case to one line of Table A.

Table 228
Compounds of the general formula IA (m=0) where $XR^1$ is methoxy, $R^3$ is methylthio and the combination of the substituents $R^4$ and $R^5$ corresponds in each case to one line of Table A.

Table 229
Compounds of the general formula IA (m=0) where $XR^1$ is ethoxy, $R^3$ is methylthio and the combination of the substituents $R^4$ and $R^5$ corresponds in each case to one line of Table A.

Table 230
Compounds of the general formula IA (m=0) where $XR^1$ is methylamino, $R^3$ is methylthio and the combination of the substituents $R^4$ and $R^5$ corresponds in each case to one line of Table A.

Table 231
Compounds of the general formula IB (m=0) where $XR^1$ is methyl, $R^2$ is methyl, $R^3$ is methylthio and the combination of the substituents $R^4$ and $R^5$ corresponds in each case to one line of Table A.

Table 232
Compounds of the general formula IB (m=0) where $XR^1$ is ethyl, $R^2$ is methyl, $R^3$ is methylthio and the combination of the substituents $R^4$ and $R^5$ corresponds in each case to one line of Table A.

Table 233
Compounds of the general formula IB (m=0) where $XR^1$ is methoxy, $R^2$ is methyl, $R^3$ is methylthio and the combination of the substituents $R^4$ and $R^5$ corresponds in each case to one line of Table A.

Table 234
Compounds of the general formula IB (m=0) where $XR^1$ is ethoxy, $R^2$ is methyl, $R^3$ is methylthio and the combination of the substituents $R^4$ and $R^5$ corresponds in each case to one line of Table A.

Table 235
Compounds of the general formula IB (m=0) where $XR^1$ is methylamino, $R^2$ is methyl, $R^3$ is methylthio and the combination of the substituents $R^4$ and $R^5$ corresponds in each case to one line of Table A.

Table 236
Compounds of the general formula IB (m=0) where $XR^1$ is methyl, $R^2$ is ethyl, $R^3$ is methylthio and the combination of the substituents $R^4$ and $R^5$ corresponds in each case to one line of Table A.

Table 237
Compounds of the general formula IB (m=0) where $XR^1$ is ethyl, $R^2$ is ethyl, $R^3$ is methylthio and the combination of the substituents $R^4$ and $R^5$ corresponds in each case to one line of Table A.

Table 238
Compounds of the general formula IB (m=0) where $XR^1$ is methoxy, $R^2$ is ethyl, $R^3$ is methylthio and the combination of the substituents $R^4$ and $R^5$ corresponds in each case to one line of Table A.

Table 239
Compounds of the general formula IB (m=0) where $XR^1$ is ethoxy, $R^2$ is ethyl, $R^3$ is methylthio and the combination of the substituents $R^4$ and $R^5$ corresponds in each case to one line of Table A.

Table 240
Compounds of the general formula IB (m=0) where $XR^1$ is methylamino, $R^2$ is ethyl, $R^3$ is methylthio and the combination of the substituents $R^4$ and $R^5$ corresponds in each case to one line of Table A.

Table 241
Compounds of the general formula IA where $R_m$ is 3-chlorine, $XR^1$ is methyl, $R^3$ is methylthio and the combination of the substituents $R^4$ and $R^5$ corresponds in each case to one line of Table A.

Table 242
Compounds of the general formula IA where $R_m$ is 3-chlorine, $XR^1$ is ethyl, $R^3$ is methylthio and the combination of the substituents $R^4$ and $R^5$ corresponds in each case to one line of Table A.

Table 243
Compounds of the general formula IA where $R_m$ is 3-chlorine, $XR^1$ is methoxy, $R^3$ is methylthio and the combination of the substituents $R^4$ and $R^5$ corresponds in each case to one line of Table A.

Table 244
Compounds of the general formula IA where $R_m$ is 3-chlorine, $XR^1$ is ethoxy, $R^3$ is methylthio and the combination of the substituents $R^4$ and $R^5$ corresponds in each case to one line of Table A.

Table 245
Compounds of the general formula IA where $R_m$ is 3-chlorine, $XR^1$ is methylamino, $R^3$ is methylthio and the combination of the substituents $R^4$ and $R^5$ corresponds in each case to one line of Table A.

Table 246
Compounds of the general formula IB where $R_m$ is 3-chlorine, $XR^1$ is methyl, $R^2$ is methyl, $R^3$ is methylthio and the combination of the substituents $R^4$ and $R^5$ corresponds in each case to one line of Table A.

Table 247
Compounds of the general formula IB where $R_m$ is 3-chlorine, $XR^1$ is ethyl, $R^2$ is methyl, $R^3$ is methylthio and the combination of the substituents $R^4$ and $R^5$ corresponds in each case to one line of Table A.

Table 248
Compounds of the general formula IB where $R_m$ is 3-chlorine, $XR^1$ is methoxy, $R^2$ is methyl, $R^3$ is methylthio and the combination of the substituents $R^4$ and $R^5$ corresponds in each case to one line of Table A.

Table 249
Compounds of the general formula IB where $R_m$ is 3-chlorine, $XR^1$ is ethoxy, $R^2$ is methyl, $R^3$ is methylthio and the combination of the substituents $R^4$ and $R^5$ corresponds in each case to one line of Table A.

Table 250
Compounds of the general formula IB where $R_m$ is 3-chlorine, $XR^1$ is methylamino, $R^2$ is methyl, $R^3$ is methylthio and the combination of the substituents $R^4$ and $R^5$ corresponds in each case to one line of Table A.

Table 251
Compounds of the general formula IB where $R_m$ is 3-chlorine, $XR^1$ is methyl, $R^2$ is ethyl, $R^3$ is methylthio and the combination of the substituents $R^4$ and $R^5$ corresponds in each case to one line of Table A.

Table 252
Compounds of the general formula IB where $R_m$ is 3-chlorine, $XR^1$ is ethyl, $R^2$ is ethyl, $R^3$ is methylthio and the combination of the substituents $R^4$ and $R^5$ corresponds in each case to one line of Table A.

Table 253
Compounds of the general formula IB where $R_m$ is 3-chlorine, $XR^1$ is methoxy, $R^2$ is ethyl, $R^3$ is methylthio and the combination of the substituents $R^4$ and $R^5$ corresponds in each case to one line of Table A.

Table 254
Compounds of the general formula IB where $R_m$ is 3-chlorine, $XR^1$ is ethoxy, $R^2$ is ethyl, $R^3$ is methylthio and the combination of the substituents $R^4$ and $R^5$ corresponds in each case to one line of Table A.

Table 255
Compounds of the general formula IB where $R_m$ is 3-chlorine, $XR^1$ is methylamino, $R^2$ is ethyl, $R^3$ is methylthio and the combination of the substituents $R^4$ and $R^5$ corresponds in each case to one line of Table A.

Table 256
Compounds of the general formula IA where $R_m$ is 6-methyl, $XR^1$ is methyl, $R^3$ is methylthio and the combination of the substituents $R^4$ and $R^5$ corresponds in each case to one line of Table A.

Table 257
Compounds of the general formula IA where $R_m$ is 6-methyl, $XR^1$ is ethyl, $R^3$ is methylthio and the combination of the substituents $R^4$ and $R^5$ corresponds in each case to one line of Table A.

Table 258
Compounds of the general formula IA where $R_m$ is 6-methyl, $XR^1$ is methoxy, $R^3$ is methylthio and the combination of the substituents $R^4$ and $R^5$ corresponds in each case to one line of Table A.

Table 259
Compounds of the general formula IA where $R_m$ is 6-methyl, $XR^1$ is ethoxy, $R^3$ is methylthio and the combination of the substituents $R^4$ and $R^5$ corresponds in each case to one line of Table A.

Table 260
Compounds of the general formula IA where $R_m$ is 6-methyl, $XR^1$ is ethylamino, $R^3$ is methylthio and the combination of the substituents $R^4$ and $R^5$ corresponds in each case to one line of Table A.

Table 261
Compounds of the general formula IB where $R_m$ is 6-methyl, $XR^1$ is ethyl, $R^2$ is methyl, $R^3$ is methylthio and the combination of the substituents $R^4$ and $R^5$ corresponds in each case to one line of Table A.

Table 262
Compounds of the general formula IB where $R_m$ is 6-methyl, $XR^1$ is ethyl, $R^2$ is methyl, $R^3$ is methylthio and the combination of the substituents $R^4$ and $R^5$ corresponds in each case to one line of Table A.

Table 263
Compounds of the general formula IB where $R_m$ is 6-methyl, $XR^1$ is methoxy, $R^2$ is methyl, $R^3$ is methylthio and the combination of the substituents $R^4$ and $R^5$ corresponds in each case to one line of Table A.

Table 264
Compounds of the general formula IB where $R_m$ is 6-methyl, $XR^1$ is ethoxy, $R^2$ is methyl, $R^3$ is methylthio and the combination of the substituents $R^4$ and $R^5$ corresponds in each case to one line of Table A.

Table 265
Compounds of the general formula IB where $R_m$ is 6-methyl, $XR^1$ is methylamino, $R^2$ is methyl, $R^3$ is methylthio and the combination of the substituents $R^4$ and $R^5$ corresponds in each case to one line of Table A.

Table 266
Compounds of the general formula IB where $R_m$ is 6-methyl, $XR^1$ is methyl, $R^2$ is ethyl, $R^3$ is methylthio and the combination of the substituents $R^4$ and $R^5$ corresponds in each case to one line of Table A.

Table 267
Compounds of the general formula IB where $R_m$ is 6-methyl, $XR^1$ is ethyl, $R^2$ is ethyl, $R^3$ is methylthio and the combination of the substituents $R^4$ and $R^5$ corresponds in each case to one line of Table A.

Table 268
Compounds of the general formula IB where $R_m$ is 6-methyl, $XR^1$ is methoxy, $R^2$ is ethyl, $R^3$ is methylthio and the combination of the substituents $R^4$ and $R^5$ corresponds in each case to one line of Table A.

Table 269
Compounds of the general formula IB where $R_m$ is 6-methyl, $XR^1$ is ethoxy, $R^2$ is ethyl, $R^3$ is methylthio and the combination of the substituents $R^4$ and $R^5$ corresponds in each case to one line of Table A.

Table 270
Compounds of the general formula IB where $R_m$ is 6-methyl, $XR^1$ is methylamino, $R^2$ is ethyl, $R^3$ is methylthio and the combination of the substituents $R^4$ and $R^5$ corresponds in each case to one line of Table A.

Table 271
Compounds of the general formula IA (m=0) where $XR^1$ is methyl, $R^3$ is cyclopropyl and the combination of the substituents $R^4$ and $R^5$ corresponds in each case to one line of Table A.

Table 272
Compounds of the general formula IA (m=0) where $XR^1$ is ethyl, $R^3$ is cyclopropyl and the combination of the substituents $R^4$ and $R^5$ corresponds in each case to one line of Table A.

Table 273
Compounds of the general formula IA (m=0) where $XR^1$ is methoxy, $R^3$ is cyclopropyl and the combination of the substituents $R^4$ and $R^5$ corresponds in each case to one line of Table A.

Table 274
Compounds of the general formula IA (m=0) where $XR^1$ is ethoxy, $R^3$ is cyclopropyl and the combination of the substituents $R^4$ and $R^5$ corresponds in each case to one line of Table A.

Table 275
Compounds of the general formula IA (m=0) where $XR^1$ is methylamino, $R^3$ is cyclopropyl and the combination of the substituents $R^4$ and $R^5$ corresponds in each case to one line of Table A.

Table 276
Compounds of the general formula IB (m=0) where $XR^1$ is methyl, $R^2$ is methyl, $R^3$ is cyclopropyl and the combination of the substituents $R^4$ and $R^5$ corresponds in each case to one line of Table A.

Table 277
Compounds of the general formula IB (m=0) where $XR^1$ is ethyl, $R^2$ is methyl, $R^3$ is cyclopropyl and the combination of the substituents $R^4$ and $R^5$ corresponds in each case to one line of Table A.

Table 278
Compounds of the general formula IB (m=0) where $XR^1$ is methoxy, $R^2$ is methyl, $R^3$ is cyclopropyl and the combination of the substituents $R^4$ and $R^5$ corresponds in each case to one line of Table A.

Table 279
Compounds of the general formula IB (m=0) where $XR^1$ is ethoxy, $R^2$ is methyl, $R^3$ is cyclopropyl and the combination of the substituents $R^4$ and $R^5$ corresponds in each case to one line of Table A.

Table 280
Compounds of the general formula IB (m=0) where $XR^1$ is methylamino, $R^2$ is methyl, $R^3$ is cyclopropyl and the combination of the substituents $R^4$ and $R^5$ corresponds in each case to one line of Table A.

Table 281
Compounds of the general formula IB (m=0) where $XR^1$ is methyl, $R^2$ is ethyl, $R^3$ is cyclopropyl and the combination of the substituents $R^4$ and $R^5$ corresponds in each case to one line of Table A.

Table 282
Compounds of the general formula IB (m=0) where $XR^1$ is ethyl, $R^2$ is ethyl, $R^3$ is cyclopropyl and the combination of the substituents $R^4$ and $R^5$ corresponds in each case to one line of Table A.

Table 283
Compounds of the general formula IB (m=0) where $XR^1$ is methoxy, $R^2$ is ethyl, $R^3$ is cyclopropyl and the combination of the substituents $R^4$ and $R^5$ corresponds in each case to one line of Table A.

Table 284
Compounds of the general formula IB (m=0) where $XR^1$ is ethoxy, $R^2$ is ethyl, $R^3$ is cyclopropyl and the combination of the substituents $R^4$ and $R^5$ corresponds in each case to one line of Table A.

Table 285
Compounds of the general formula IB (m=0) where $XR^1$ is methylamino, $R^2$ is ethyl, $R^3$ is cyclopropyl and the combination of the substituents $R^4$ and $R^5$ corresponds in each case to one line of Table A.

Table 286
Compounds of the general formula IA where $R_m$ is 3-chlorine, $XR^1$ is methyl, $R^3$ is cyclopropyl and the combination of the substituents $R^4$ and $R^5$ corresponds in each case to one line of Table A.

Table 287
Compounds of the general formula IA where $R_m$ is 3-chlorine, $XR^1$ is ethyl, $R^3$ is cyclopropyl and the combination of the substituents $R^4$ and $R^5$ corresponds in each case to one line of Table A.

Table 288
Compounds of the general formula IA where $R_m$ is 3-chlorine, $XR^1$ is methoxy, $R^3$ is cyclopropyl and the combination of the substituents $R^4$ and $R^5$ corresponds in each case to one line of Table A.

Table 289
Compounds of the general formula IA where $R_m$ is 3-chlorine, $XR^1$ is ethoxy, $R^3$ is cyclopropyl and the combination of the substituents $R^4$ and $R^5$ corresponds in each case to one line of Table A.

Table 290
Compounds of the general formula IA where $R_m$ is 3-chlorine, $XR^1$ is methylamino, $R^3$ is cyclopropyl and the combination of the substituents $R^4$ and $R^5$ corresponds in each case to one line of Table A.

Table 291
Compounds of the general formula IB where $R_m$ is 3-chlorine, $XR^1$ is methyl, $R^2$ is methyl, $R^3$ is cyclopropyl and the combination of the substituents $R^4$ and $R^5$ corresponds in each case to one line of Table A.

Table 292
Compounds of the general formula IB where $R_m$ is 3-chlorine, $XR^1$ is ethyl, $R^2$ is methyl, $R^3$ is cyclopropyl and the combination of the substituents $R^4$ and $R^5$ corresponds in each case to one line of Table A.

Table 293
Compounds of the general formula IB where $R_m$ is 3-chlorine, $XR^1$ is methoxy, $R^2$ is methyl, $R^3$ is cyclopropyl and the combination of the substituents $R^4$ and $R^5$ corresponds in each case to one line of Table A.

Table 294
Compounds of the general formula IB where $R_m$ is 3-chlorine, $XR^1$ is ethoxy, $R^2$ is methyl, $R^3$ is cyclopropyl and the combination of the substituents $R^4$ and $R^5$ corresponds in each case to one line of Table A.

Table 295
Compounds of the general formula IB where $R_m$ is 3-chlorine, $XR^1$ is methylamino, $R^2$ is methyl, $R^3$ is cyclopropyl and the combination of the substituents $R^4$ and $R^5$ corresponds in each case to one line of Table A.

Table 296
Compounds of the general formula IB where $R_m$ is 3-chlorine, $XR^1$ is methyl, $R^2$ is ethyl, $R^3$ is cyclopropyl and the combination of the substituents $R^4$ and $R^5$ corresponds in each case to one line of Table A.

Table 297
Compounds of the general formula IB where $R_m$ is 3-chlorine, $XR^1$ is ethyl, $R^2$ is ethyl, $R^3$ is cyclopropyl and the combination of the substituents $R^4$ and $R^5$ corresponds in each case to one line of Table A.

Table 298
Compounds of the general formula IB where $R_m$ is 3-chlorine, $XR^1$ is methoxy, $R^2$ is ethyl, $R^3$ is cyclopropyl and the combination of the substituents $R^4$ and $R^5$ corresponds in each case to one line of Table A.

Table 299
Compounds of the general formula IB where $R_m$ is 3-chlorine, $XR^1$ is ethoxy, $R^2$ is ethyl, $R^3$ is cyclopropyl and the combination of the substituents $R^4$ and $R^5$ corresponds in each case to one line of Table A.

Table 300
Compounds of the general formula IB where $R_m$ is 3-chlorine, $XR^1$ is methylamino, $R^2$ is ethyl, $R^3$ is cyclopropyl and the combination of the substituents $R^4$ and $R^5$ corresponds in each case to one line of Table A.

Table 301
Compounds of the general formula IA where $R_m$ is 6-methyl, $XR^1$ is methyl, $R^3$ is cyclopropyl and the combination of the substituents $R^4$ and $R^5$ corresponds in each case to one line of Table A.

Table 302
Compounds of the general formula IA where $R_m$ is 6-methyl, $XR^1$ is ethyl, $R^3$ is cyclopropyl and the combination of the substituents $R^4$ and $R^5$ corresponds in each case to one line of Table A.

Table 303
Compounds of the general formula IA where $R_m$ is 6-methyl, $XR^1$ is methoxy, $R^3$ is cyclopropyl and the combination of the substituents $R^4$ and $R^5$ corresponds in each case to one line of Table A.

Table 304
Compounds of the general formula IA where $R_m$ is 6-methyl, $XR^1$ is ethoxy, $R^3$ is cyclopropyl and the combination of the substituents $R^4$ and $R^5$ corresponds in each case to one line of Table A.

Table 305
Compounds of the general formula IA where $R_m$ is 6-methyl, $XR^1$ is methylamino, $R^3$ is cyclopropyl and the combination of the substituents $R^4$ and $R^5$ corresponds in each case to one line of Table A.

Table 306
Compounds of the general formula IB where $R_m$ is 6-methyl, $XR^1$ is methyl, $R^2$ is methyl, $R^3$ is cyclopropyl and the combination of the substituents $R^4$ and $R^5$ corresponds in each case to one line of Table A.

Table 307
Compounds of the general formula IB where $R_m$ is 6-methyl, $XR^1$ is ethyl, $R^2$ is methyl, $R^3$ is cyclopropyl and the combination of the substituents $R^4$ and $R^5$ corresponds in each case to one line of Table A.

Table 308
Compounds of the general formula IB where $R_m$ is 6-methyl, $XR^1$ is methoxy, $R^2$ is methyl, $R^3$ is cyclopropyl and the combination of the substituents $R^4$ and $R^5$ corresponds in each case to one line of Table A.

Table 309
Compounds of the general formula IB where $R_m$ is 6-methyl, $XR^1$ is ethoxy, $R^2$ is methyl, $R^3$ is cyclopropyl and the combination of the substituents $R^4$ and $R^5$ corresponds in each case to one line of Table A.

Table 310
Compounds of the general formula IB where $R_m$ is 6-methyl, $XR^1$ is methylamino, $R^2$ is methyl, $R^3$ is cyclopropyl and the combination of the substituents $R^4$ and $R^5$ corresponds in each case to one line of Table A.

Table 311
Compounds of the general formula IB where $R_m$ is 6-methyl, $XR^1$ is methyl, $R^2$ is ethyl, $R^3$ is cyclopropyl and the combination of the substituents $R^4$ and $R^5$ corresponds in each case to one line of Table A.

Table 312
Compounds of the general formula IB where $R_m$ is 6-methyl, $XR^1$ is ethyl, $R^2$ is ethyl, $R^3$ is cyclopropyl and the combination of the substituents $R^4$ and $R^5$ corresponds in each case to one line of Table A.

Table 313
Compounds of the general formula IB where $R_m$ is 6-methyl, $XR^1$ is methoxy, $R^2$ is ethyl, $R^3$ is cyclopropyl and the combination of the substituents $R^4$ and $R^5$ corresponds in each case to one line of Table A.

Table 314
Compounds of the general formula IB where $R_m$ is 6-methyl, $XR^1$ is ethoxy, $R^2$ is ethyl, $R^3$ is cyclopropyl and the combination of the substituents $R^4$ and $R^5$ corresponds in each case to one line of Table A.

Table 315
Compounds of the general formula IB where $R_m$ is 6-methyl, $XR^1$ is methylamino, $R^2$ is ethyl, $R^3$ is cyclopropyl and the combination of the substituents $R^4$ and $R^5$ corresponds in each case to one line of Table A.

Table 316
Compounds of the general formula IC (m=0) where $XR^1$ is methoxy, $R^2$ is hydrogen, $R^3$ is methyl, $R^d$ is methyl, $R^e$ is methyl and $R^4$ is $R^x$-substituted phenyl, where Rx corresponds in each case to one line of Table B.

IC $$R_m \underset{R^2O-N-COXR^1}{\overset{CH_2O-CR^3=N-N=CR^4CR^d=NOR^e}{\text{[phenyl ring]}}}$$

Table 317
Compounds of the general formula IC (m=0) where $XR^1$ is methoxy, $R^2$ is methyl, $R^3$ is methyl, $R^d$ is methyl, $R^e$ is methyl and $R^4$ is $R^x$-substituted phenyl, where Rx corresponds in each case to one line of Table B.

Table 318
Compounds of the general formula IC (m=0) where $XR^1$ is methylamino, $R^2$ is hydrogen, $R^3$ is methyl, $R^d$ is methyl, $R^e$ is methyl and $R^4$ is $R^x$-substituted phenyl, where $R^x$ corresponds in each case to one line of Table B.

Table 319
Compounds of the general formula IC (m=0) where $XR^1$ is methylamino, $R^2$ is methyl, $R^3$ is methyl, $R^d$ is methyl, $R^e$ is methyl and $R^4$ is $R^x$-substituted phenyl, where Rx corresponds in each case to one line of Table B.

Table 320
Compounds of the general formula IC (m=0) where $XR^1$ is methoxy, $R^2$ is hydrogen, $R^3$ is ethyl, $R^d$ is methyl, $R^e$ is methyl and $R^4$ is $R^x$-substituted phenyl, where Rx corresponds in each case to one line of Table B.

Table 321
Compounds of the general formula IC (m=0) where XR1 is methoxy, $R^2$ is ethyl, $R^3$ is ethyl, $R^d$ is methyl, $R^e$ is methyl and $R^4$ is $R^x$-substituted phenyl, where $R^x$ corresponds in each case to one line of Table B.

Table 322
Compounds of the general formula IC (m=0) where $XR^1$ is methylamino, $R^2$ is hydrogen, $R^3$ is ethyl, $R^d$ is methyl, $R^e$ is methyl and $R^4$ is $R^x$-substituted phenyl, where $R^x$ corresponds in each case to one line of Table B.

Table 323
Compounds of the general formula IC (m=0) where $XR^1$ is methylamino, $R^2$ is ethyl, $R^3$ is ethyl, $R^d$ is methyl, $R^e$ is methyl and $R^4$ is $R^x$-substituted phenyl, where $R^x$ corresponds in each case to one line of Table B.

Table 324
Compounds of the general formula IC (m=0) where $XR^1$ is methoxy, $R^2$ is hydrogen, $R^3$ is cyclopropyl, $R^d$ is methyl, $R^e$ is methyl and $R^4$ is $R^x$-substituted phenyl, where $R^x$ corresponds in each case to one line of Table B.

Table 325
Compounds of the general formula IC (m=0) where $XR^1$ is methoxy, $R^2$ is cyclopropyl, $R^3$ is cyclopropyl, $R^d$ is methyl, $R^e$ is methyl and $R^4$ is $R^x$-substituted phenyl, where $R^x$ corresponds in each case to one line of Table B.

Table 326
Compounds of the general formula IC (m=0) where $XR^1$ is methylamino, $R^2$ is hydrogen, $R^3$ is cyclopropyl, $R^d$ is methyl, $R^e$ is methyl and $R^4$ is $R^x$-substituted phenyl, where $R^x$ corresponds in each case to one line of Table B.

Table 327
Compounds of the general formula IC (m=0) where $XR^1$ is methylamino, $R^2$ is cyclopropyl, $R^3$ is cyclopropyl, $R^d$ is methyl, $R^e$ is methyl and $R^4$ is $R^x$-substituted phenyl, where $R^x$ corresponds in each case to one line of Table B.

Table 328
Compounds of the general formula IC (m=0) where $XR^1$ is methoxy, $R^2$ is hydrogen, $R^3$ is methyl, $R^4$ is methyl, $R^e$ is methyl and $R^d$ is $R^x$-substituted phenyl, where $R^x$ corresponds in each case to one line of Table B.

Table 329
Compounds of the general formula IC (m=0) where $XR^1$ is methoxy, $R^2$ is methyl, $R^3$ is methyl, $R^4$ is methyl, $R^e$ is methyl and $R^d$ is $R^x$-substituted phenyl, where $R^x$ corresponds in each case to one line of Table B.

Table 330
Compounds of the general formula IC (m=0) where $XR^1$ is methylamino, $R^2$ is hydrogen, $R^3$ is methyl, $R^4$ is methyl, $R^e$ is methyl and $R^d$ is $R^x$-substituted phenyl, where $R^x$ corresponds in each case to one line of Table B.

Table 331
Compounds of the general formula IC (m=0) where $XR^1$ is methylamino, $R^2$ is methyl, $R^3$ is methyl, $R^4$ is methyl, $R^e$ is methyl and $R^d$ is $R^x$-substituted phenyl, where $R^x$ corresponds in each case to one line of Table B.

Table 332
Compounds of the general formula IC (m=0) where $XR^1$ is methoxy, $R^2$ is hydrogen, $R^3$ is methyl, $R^4$ is ethyl, $R^e$ is methyl and $R^d$ is $R^x$-substituted phenyl, where $R^x$ corresponds in each case to one line of Table B.

Table 333
Compounds of the general formula IC (m=0) where $XR^1$ is methoxy, $R^2$ is methyl, $R^3$ is methyl, $R^4$ is ethyl, $R^e$ is methyl and $R^d$ is $R^x$-substituted phenyl, where $R^x$ corresponds in each case to one line of Table B.

Table 334
Compounds of the general formula IC (m=0) where $XR^1$ is methylamino, $R^2$ is hydrogen, $R^3$ is methyl, $R^4$ is ethyl, $R^e$ is methyl and $R^d$ is $R^x$-substituted phenyl, where $R^x$ corresponds in each case to one line of Table B.

Table 335
Compounds of the general formula IC (m=0) where $XR^1$ is methylamino, $R^2$ is methyl, $R^3$ is methyl, $R^4$ is ethyl, $R^e$ is methyl and $R^d$ is $R^x$-substituted phenyl, where $R^x$ corresponds in each case to one line of Table B.

Table 336
Compounds of the general formula IC (m=0) where $XR^1$ is methoxy, $R^2$ is hydrogen, $R^3$ is methyl, $R^4$ is iso-propyl, $R^e$ is methyl and $R^d$ is $R^x$-substituted phenyl, where $R^x$ corresponds in each case to one line of Table B.

Table 337
Compounds of the general formula IC (m=0) where $XR^1$ is methoxy, $R^2$ is methyl, $R^3$ is methyl, $R^4$ is iso-propyl, $R^e$ is methyl and $R^d$ is $R^x$-substituted phenyl, where $R^x$ corresponds in each case to one line of Table B.

Table 338
Compounds of the general formula IC (m=0) where $XR^1$ is methylamino, $R^2$ is hydrogen, $R^3$ is methyl, $R^4$ is iso-propyl, $R^e$ is methyl and $R^d$ is $R^x$-substituted phenyl, where $R^x$ corresponds in each case to one line of Table B.

Table 339
Compounds of the general formula IC (m=0) where $XR^1$ is methylamino, $R^2$ is methyl, $R^3$ is methyl, $R^4$ is iso-propyl, $R^e$ is methyl and $R^d$ is $R^x$-substituted phenyl, where $R^x$ corresponds in each case to one line of Table B.

Table 340
Compounds of the general formula IC (m=0) where $XR^1$ is methoxy, $R^2$ is hydrogen, $R^3$ is methyl, $R^4$ is methyl, $R^e$ is ethyl and $R^d$ is $R^x$-substituted phenyl, where $R^x$ corresponds in each case to one line of Table B.

Table 341
Compounds of the general formula IC (m=0) where $XR^1$ is methoxy, $R^2$ is methyl, $R^3$ is methyl, $R^4$ is methyl, $R^e$ is ethyl and $R^d$ is $R^x$-substituted phenyl, where $R^x$ corresponds in each case to one line of Table B.

Table 342
Compounds of the general formula IC (m=0) where $XR^1$ is methylamino, $R^2$ is hydrogen, $R^3$ is methyl, $R^4$ is methyl, $R^e$ is ethyl and $R^d$ is $R^x$-substituted phenyl, where $R^x$ corresponds in each case to one line of Table B.

Table 343
Compounds of the general formula IC (m=0) where $XR^1$ is methylamino, $R^2$ is methyl, $R^3$ is methyl, $R^4$ is methyl, $R^e$ is ethyl and $R^d$ is $R^x$-substituted phenyl, where $R^x$ corresponds in each case to one line of Table B.

Table 344
Compounds of the general formula IC (m=0) where $XR^1$ is methoxy, $R^2$ is hydrogen, $R^3$ is methyl, $R^4$ is methyl, $R^e$ is n-propyl and $R^d$ is $R^x$-substituted phenyl, where $R^x$ corresponds in each case to one line of Table B.

Table 345
Compounds of the general formula IC (m=0) where $XR^1$ is methoxy, $R^2$ is methyl, $R^3$ is methyl, $R^4$ is methyl, $R^e$ is n-propyl and $R^d$ is $R^x$-substituted phenyl, where $R^x$ corresponds in each case to one line of Table B.

Table 346
Compounds of the general formula IC (m=0) where $XR^1$ is methylamino, $R^2$ is hydrogen, $R^3$ is methyl, $R^4$ is methyl, $R^e$ is n-propyl and $R^d$ is $R^x$-substituted phenyl, where $R^x$ corresponds in each case to one line of Table B.

Table 347
Compounds of the general formula IC (m=0) where $XR^1$ is methylamino, $R^2$ is methyl, $R^3$ is methyl, $R^4$ is methyl, $R^e$ is n-propyl and $R^d$ is $R^x$-substituted phenyl, where $R^x$ corresponds in each case to one line of Table B.

Table 348
Compounds of the general formula IC (m=0) where $XR^1$ is methoxy, $R^2$ is hydrogen, $R^3$ is methyl, $R^4$ is methyl, $R^e$ is iso-propyl and $R^d$ is $R^x$-substituted phenyl, where $R^x$ corresponds in each case to one line of Table B.

Table 349
Compounds of the general formula IC (m=0) where $XR^1$ is methoxy, $R^2$ is methyl, $R^3$ is methyl, $R^4$ is methyl, $R^e$ is iso-propyl and $R^d$ is $R^x$-substituted phenyl, where $R^x$ corresponds in each case to one line of Table B.

Table 350
Compounds of the general formula IC (m=0) where $XR^1$ is methylamino, $R^2$ is hydrogen, $R^3$ is methyl, $R^4$ is methyl, $R^e$ is iso-propyl and $R^d$ is $R^x$-substituted phenyl, where $R^x$ corresponds in each case to one line of Table B.

Table 351
Compounds of the general formula IC (m=0) where $XR^1$ is methylamino, $R^2$ is methyl, $R^3$ is methyl, $R^4$ is methyl, $R^e$ is iso-propyl and $R^d$ is $R^x$-substituted phenyl, where $R^x$ corresponds in each case to one line of Table B.

Table 352
Compounds of the general formula IC (m=0) where $XR^1$ is methoxy, $R^2$ is hydrogen, $R^3$ is methyl, $R^4$ is methyl, $R^e$ is tert-butyl and $R^d$ is $R^x$-substituted phenyl, where $R^x$ corresponds in each case to one line of Table B.

Table 353
Compounds of the general formula IC (m=0) where $XR^1$ is methoxy, $R^2$ is methyl, $R^3$ is methyl, $R^4$ is methyl, $R^e$ is tert-butyl and $R^d$ is $R^x$-substituted phenyl, where $R^x$ corresponds in each case to one line of Table B.

Table 354
Compounds of the general formula IC (m=0) where $XR^1$ is methylamino, $R^2$ is hydrogen, $R^3$ is methyl, $R^4$ is methyl, $R^e$ is tert-butyl and $R^d$ is $R^x$-substituted phenyl, where $R^x$ corresponds in each case to one line of Table B.

Table 355
Compounds of the general formula IC (m=0) where $XR^1$ is methylamino, $R^2$ is methyl, $R^3$ is methyl, $R^4$ is methyl, $R^e$ is tert-butyl and $R^d$ is $R^x$-substituted phenyl, where $R^x$ corresponds in each case to one line of Table B.

Table 356
Compounds of the general formula IC (m=0) where $XR^1$ is methoxy, $R^2$ is hydrogen, $R^3$ is methyl, $R^4$ is methyl, $R^e$ is benzyl and $R^d$ is $R^x$-substituted phenyl, where $R^x$ corresponds in each case to one line of Table B.

Table 357
Compounds of the general formula IC (m=0) where $XR^1$ is methoxy, $R^2$ is methyl, $R^3$ is methyl, $R^4$ is methyl, $R^e$ is benzyl and $R^d$ is $R^x$-substituted phenyl, where $R^x$ corresponds in each case to one line of Table B.

Table 358
Compounds of the general formula IC (m=0) where $XR^1$ is methylamino, $R^2$ is hydrogen, $R^3$ is methyl, $R^4$ is methyl, $R^e$ is benzyl and $R^d$ is $R^x$-substituted phenyl, where $R^x$ corresponds in each case to one line of Table B.

Table 359
Compounds of the general formula IC (m=0) where $XR^1$ is methylamino, $R^2$ is methyl, $R^3$ is methyl, $R^4$ is methyl, $R^e$ is benzyl and $R^d$ is $R^x$-substituted phenyl, where $R^x$ corresponds in each case to one line of Table B.

Table 360
Compounds of the general formula IC (m=0) where $XR^1$ is methoxy, $R^2$ is hydrogen, $R^3$ is methyl, $R^4$ is methyl, $R^e$ is propargyl and $R^d$ is $R^x$-substituted phenyl, where $R^x$ corresponds in each case to one line of Table B.

Table 361
Compounds of the general formula IC (m=0) where $XR^1$ is methoxy, $R^2$ is methyl, $R^3$ is methyl, $R^4$ is methyl, $R^e$ is propargyl and $R^d$ is $R^x$-substituted phenyl, where $R^x$ corresponds in each case to one line of Table B.

Table 362
Compounds of the general formula IC (m=0) where $XR^1$ is methylamino, $R^2$ is hydrogen, $R^3$ is methyl, $R^4$ is methyl, $R^e$ is propargyl and $R^d$ is $R^x$-substituted phenyl, where $R^x$ corresponds in each case to one line of Table B.

Table 363
Compounds of the general formula IC (m=0) where $XR^1$ is methylamino, $R^2$ is methyl, $R^3$ is methyl, $R^4$ is methyl, $R^e$ is propargyl and $R^d$ is $R^x$-substituted phenyl, where $R^x$ corresponds in each case to one line of Table B.

Table 364
Compounds of the general formula IC (m=0) where $XR^1$ is methoxy, $R^2$ is hydrogen, $R^3$ is methyl, $R^4$ is methyl, $R^e$ is bromopropargyl and $R^d$ is $R^x$-substituted phenyl, where $R^x$ corresponds in each case to one line of Table B.

Table 365
Compounds of the general formula IC (m=0) where $XR^1$ is methoxy, $R^2$ is methyl, $R^3$ is methyl, $R^4$ is methyl, $R^e$ is bromopropargyl and $R^d$ is $R^x$-substituted phenyl, where $R^x$ corresponds in each case to one line of Table B.

Table 366
Compounds of the general formula IC (m=0) where $XR^1$ is methylamino, $R^2$ is hydrogen, $R^3$ is methyl, $R^4$ is methyl, $R^e$ is bromopropargyl and $R^d$ is $R^x$-substituted phenyl, where $R^x$ corresponds in each case to one line of Table B.

Table 367
Compounds of the general formula IC (m=0) where $XR^1$ is methylamino, $R^2$ is methyl, $R^3$ is methyl, $R^4$ is methyl, $R^e$ is bromopropargyl and $R^d$ is $R^x$-substituted phenyl, where $R^x$ corresponds in each case to one line of Table B.

Table 368
Compounds of the general formula IC (m=0) where $XR^1$ is methoxy, $R^2$ is hydrogen, $R^3$ is methyl, $R^4$ is methyl, $R^e$ is iodopropargyl and $R^d$ is $R^x$-substituted phenyl, where $R^x$ corresponds in each case to one line of Table B.

Table 369
Compounds of the general formula IC (m=0) where $XR^1$ is methoxy, $R^2$ is methyl, $R^3$ is methyl, $R^4$ is methyl, $R^e$ is iodopropargyl and $R^d$ is $R^x$-substituted phenyl, where $R^x$ corresponds in each case to one line of Table B.

Table 370
Compounds of the general formula IC (m=0) where $XR^1$ is methylamino, $R^2$ is hydrogen, $R^3$ is methyl, $R^4$ is methyl, $R^e$ is iodopropargyl and $R^d$ is $R^x$-substituted phenyl, where $R^x$ corresponds in each case to one line of Table B.

Table 371
Compounds of the general formula IC (m=0) where $XR^1$ is methylamino, $R^2$ is methyl, $R^3$ is methyl, $R^4$ is methyl, $R^e$ is iodopropargyl and $R^d$ is $R^x$-substituted phenyl, where $R^x$ corresponds in each case to one line of Table B.

Table 372
Compounds of the general formula IC (m=0) where $XR^1$ is methoxy, $R^2$ is hydrogen, $R^3$ is methyl, $R^4$ is methyl, $R^e$ is allyl and $R^d$ is $R^x$-substituted phenyl, where $R^x$ corresponds in each case to one line of Table B.

Table 373
Compounds of the general formula IC (m=0) where $XR^1$ is methoxy, $R^2$ is methyl, $R^3$ is methyl, $R^4$ is methyl, $R^e$ is allyl and $R^d$ is $R^x$-substituted phenyl, where $R^x$ corresponds in each case to one line of Table B.

Table 374
Compounds of the general formula IC (m=0) where $XR^1$ is methylamino, $R^2$ is hydrogen, $R^3$ is methyl, $R^4$ is methyl, $R^e$ is allyl and $R^d$ is $R^x$-substituted phenyl, where $R^x$ corresponds in each case to one line of Table B.

Table 375
Compounds of the general formula IC (m=0) where $XR^1$ is methylamino, $R^2$ is methyl, $R^3$ is methyl, $R^4$ is methyl, $R^e$ is allyl and $R^d$ is $R^x$-substituted phenyl, where $R^x$ corresponds in each case to one line of Table B.

Table 376
Compounds of the general formula IC (m=0) where $XR^1$ is methoxy, $R^2$ is hydrogen, $R^3$ is methyl, $R^4$ is methyl, $R^e$ is trans-chloroallyl and $R^d$ is $R^x$-substituted phenyl, where $R^x$ corresponds in each case to one line of Table B.

Table 377
Compounds of the general formula IC (m=0) where $XR^1$ is methoxy, $R^2$ is methyl, $R^3$ is methyl, $R^4$ is methyl, $R^e$ is trans-chloroallyl and $R^d$ is $R^x$-substituted phenyl, where $R^x$ corresponds in each case to one line of Table B.

Table 378
Compounds of the general formula IC (m=0) where $XR^1$ is methylamino, $R^2$ is hydrogen, $R^3$ is methyl, $R^4$ is methyl, $R^e$ is transchloroallyl and $R^d$ is $R^x$-substituted phenyl, where $R^x$ corresponds in each case to one line of Table B.

Table 379
Compounds of the general formula IC (m=0) where $XR^1$ is methylamino, $R^2$ is methyl, $R^3$ is methyl, $R^4$ is methyl, $R^e$ is trans-chloroallyl and $R^d$ is $R^x$-substituted phenyl, where $R^x$ corresponds in each case to one line of Table B.

Table 380
Compounds of the general formula IC (m=0) where $XR^1$ is methoxy, $R^2$ is hydrogen, $R^3$ is methyl, $R^4$ is methyl, $R^e$ is methoxyethyl and $R^d$ is $R^x$-substituted phenyl, where $R^x$ corresponds in each case to one line of Table B.

Table 381
Compounds of the general formula IC (m=0) where $XR^1$ is methoxy, $R^2$ is methyl, $R^3$ is methyl, $R^4$ is methyl, $R^e$ is methoxyethyl and $R^d$ is $R^x$-substituted phenyl, where $R^x$ corresponds in each case to one line of Table B.

Table 382
Compounds of the general formula IC (m=0) where $XR^1$ is methylamino, $R^2$ is hydrogen, $R^3$ is methyl, $R^4$ is methyl, $R^e$ is methoxyethyl and $R^d$ is $R^x$-substituted phenyl, where $R^x$ corresponds in each case to one line of Table B.

Table 383
Compounds of the general formula IC (m=0) where $XR^1$ is methylamino, $R^2$ is methyl, $R^3$ is methyl, $R^4$ is methyl, $R^e$ is methoxyethyl and $R^d$ is $R^x$-substituted phenyl, where $R^x$ corresponds in each case to one line of Table B.

Table 384
Compounds of the general formula IC (m=0) where $XR^1$ is methoxy, $R^2$ is hydrogen and the combination of the radicals $R^3$, $R^4$, $R^d$ and $R^e$ corresponds in each case to one line of Table C.

Table 385
Compounds of the general formula IC (m=0) where $XR^1$ is methoxy, $R^2$ is methyl and the combination of the radicals $R^3$, $R^4$, $R^d$ and $R^e$ corresponds in each case to one line of Table C.

Table 386
Compounds of the general formula IC (m=0) where $XR^1$ is methyl-amino, $R^2$ is hydrogen and the combination of the radicals $R^3$, $R^4$, $R^d$ and $R^e$ corresponds in each case to one line of Table C.

Table 387

Compounds of the general formula IC (m=0) where $XR^1$ is methylamino, $R^2$ is methyl and the combination of the radicals $R^3$, $R^4$, $R^d$ and $R^e$ corresponds in each case to one line of Table C.

TABLE A

| No. | $R^4$ | $R^5$ |
|---|---|---|
| 01 | $CH_3$ | $C_6H_5$ |
| 02 | $CH_3$ | $2\text{-}F\text{—}C_6H_4$ |
| 03 | $CH_3$ | $3\text{-}F\text{—}C_6H_4$ |
| 04 | $CH_3$ | $4\text{-}F\text{—}C_6H_4$ |
| 05 | $CH_3$ | $2,4\text{-}F_2\text{—}C_6H_3$ |
| 06 | $CH_3$ | $2,3\text{-}F_2\text{—}C_6H_3$ |
| 07 | $CH_3$ | $2,4,6\text{-}F_3\text{—}C_6H_2$ |
| 08 | $CH_3$ | $C_6F_5$ |
| 09 | $CH_3$ | $2\text{-}Cl\text{—}C_6H_4$ |
| 10 | $CH_3$ | $3\text{-}Cl\text{—}C_6H_4$ |
| 11 | $CH_3$ | $4\text{-}Cl\text{—}C_6H_4$ |
| 12 | $CH_3$ | $2,3\text{-}Cl_2\text{—}C_6H_3$ |
| 13 | $CH_3$ | $2,4\text{-}Cl_2\text{—}C_6H_3$ |
| 14 | $CH_3$ | $2,5\text{-}Cl_2\text{—}C_6H_3$ |
| 15 | $CH_3$ | $2,6\text{-}Cl_2\text{—}C_6H_3$ |
| 16 | $CH_3$ | $3,4\text{-}Cl_2\text{—}C_6H_3$ |
| 17 | $CH_3$ | $3,5\text{-}Cl_2\text{—}C_6H_3$ |
| 18 | $CH_3$ | $2,3,4\text{-}Cl_3\text{—}C_6H_2$ |
| 19 | $CH_3$ | $2,3,5\text{-}Cl_3\text{—}C_6H_2$ |
| 20 | $CH_3$ | $2,3,6\text{-}Cl_3\text{—}C_6H_2$ |
| 21 | $CH_3$ | $2,4,5\text{-}Cl_3\text{—}C_6H_2$ |
| 22 | $CH_3$ | $2,4,6\text{-}Cl_3\text{—}C_6H_2$ |
| 23 | $CH_3$ | $3,4,5\text{-}Cl_3\text{—}C_6H_2$ |
| 24 | $CH_3$ | $2,3,4,6\text{-}Cl_4\text{—}C_6H$ |
| 25 | $CH_3$ | $2,3,5,6\text{-}Cl_4\text{—}C_6H$ |
| 26 | $CH_3$ | $C_6Cl_5$ |
| 27 | $CH_3$ | $2\text{-}Br\text{—}C_6H_4$ |
| 28 | $CH_3$ | $3\text{-}Br\text{—}C_6H_4$ |
| 29 | $CH_3$ | $4\text{-}Br\text{—}C_6H_4$ |
| 30 | $CH_3$ | $2,4\text{-}Br_2\text{—}C_6H_3$ |
| 31 | $CH_3$ | $2,5\text{-}Br_2\text{—}C_6H_3$ |
| 32 | $CH_3$ | $2,6\text{-}Br_2\text{—}C_6H_3$ |
| 33 | $CH_3$ | $2,4,6\text{-}Br_3\text{—}C_6H_2$ |
| 34 | $CH_3$ | $C_6Br_5$ |
| 35 | $CH_3$ | $2\text{-}I\text{—}C_6H_4$ |
| 36 | $CH_3$ | $3\text{-}I\text{—}C_6H_4$ |
| 37 | $CH_3$ | $4\text{-}I\text{—}C_6H_4$ |
| 38 | $CH_3$ | $2,4\text{-}I_2\text{—}C_6H_3$ |
| 39 | $CH_3$ | $2\text{-}Cl,\ 3\text{-}F\text{—}C_6H_3$ |
| 40 | $CH_3$ | $2\text{-}Cl,\ 4\text{-}F\text{—}C_6H_3$ |
| 41 | $CH_3$ | $2\text{-}Cl,\ 5\text{-}F\text{—}C_6H_3$ |
| 42 | $CH_3$ | $2\text{-}Cl,\ 6\text{-}F\text{—}C_6H_3$ |
| 43 | $CH_3$ | $2\text{-}Cl,\ 3\text{-}Br\text{—}C_6H_3$ |
| 44 | $CH_3$ | $2\text{-}Cl,\ 4\text{-}Br\text{—}C_6H_3$ |
| 45 | $CH_3$ | $2\text{-}Cl,\ 5\text{-}Br\text{—}C_6H_3$ |
| 46 | $CH_3$ | $2\text{-}Cl,\ 6\text{-}Br\text{—}C_6H_3$ |
| 47 | $CH_3$ | $2\text{-}Br,\ 3\text{-}Cl\text{—}C_6H_3$ |
| 48 | $CH_3$ | $2\text{-}Br,\ 4\text{-}Cl\text{—}C_6H_3$ |
| 49 | $CH_3$ | $2\text{-}Br,\ 5\text{-}Cl\text{—}C_6H_3$ |
| 50 | $CH_3$ | $2\text{-}Br,\ 6\text{-}Cl\text{—}C_6H_3$ |
| 51 | $CH_3$ | $2\text{-}Br,\ 3\text{-}F\text{—}C_6H_3$ |
| 52 | $CH_3$ | $2\text{-}Br,\ 4\text{-}F\text{—}C_6H_3$ |
| 53 | $CH_3$ | $2\text{-}Br,\ 5\text{-}F\text{—}C_6H_3$ |
| 54 | $CH_3$ | $2\text{-}Br,\ 6\text{-}F\text{—}C_6H_3$ |
| 55 | $CH_3$ | $2\text{-}F,\ 3\text{-}Cl\text{—}C_6H_3$ |
| 56 | $CH_3$ | $2\text{-}F,\ 4\text{-}Cl\text{—}C_6H_3$ |
| 57 | $CH_3$ | $2\text{-}F,\ 5\text{-}Cl\text{—}C_6H_3$ |
| 58 | $CH_3$ | $4\text{-}F,\ 3\text{-}Cl\text{—}C_6H_3$ |
| 59 | $CH_3$ | $5\text{-}F,\ 3\text{-}Cl\text{—}C_6H_3$ |
| 60 | $CH_3$ | $4\text{-}Br,\ 3\text{-}Cl\text{—}C_6H_3$ |
| 61 | $CH_3$ | $5\text{-}Br,\ 3\text{-}Cl\text{—}C_6H_3$ |
| 62 | $CH_3$ | $3\text{-}F,\ 4\text{-}Cl\text{—}C_6H_3$ |
| 63 | $CH_3$ | $3\text{-}F,\ 4\text{-}Br\text{—}C_6H_3$ |
| 64 | $CH_3$ | $3\text{-}Br,\ 4\text{-}Cl\text{—}C_6H_3$ |
| 65 | $CH_3$ | $4\text{-}F,\ 3\text{-}Br\text{—}C_6H_3$ |
| 66 | $CH_3$ | $2,6\text{-}Cl_2,\ 4\text{-}Br\text{—}C_6H_2$ |
| 67 | $CH_3$ | $2\text{-}CH_3\text{—}C_6H_4$ |
| 68 | $CH_3$ | $3\text{-}CH_3\text{—}C_6H_4$ |
| 69 | $CH_3$ | $4\text{-}CH_3\text{—}C_6H_4$ |
| 70 | $CH_3$ | $2,3\text{-}(CH_3)_2\text{—}C_6H_3$ |
| 71 | $CH_3$ | $2,4\text{-}(CH_3)_2\text{—}C_6H_3$ |
| 72 | $CH_3$ | $2,5\text{-}(CH_3)_2\text{—}C_6H_3$ |
| 73 | $CH_3$ | $2,6\text{-}(CH_3)_2\text{—}C_6H_3$ |
| 74 | $CH_3$ | $3,4\text{-}(CH_3)_2\text{—}C_6H_3$ |
| 75 | $CH_3$ | $3,5\text{-}(CH_3)_2\text{—}C_6H_3$ |
| 76 | $CH_3$ | $2,3,4\text{-}(CH_3)_3\text{—}C_6H_2$ |
| 77 | $CH_3$ | $2,3,5\text{-}(CH_3)_3\text{—}C_6H_2$ |
| 78 | $CH_3$ | $2,3,6\text{-}(CH_3)_3\text{—}C_6H_2$ |
| 79 | $CH_3$ | $2,4,5\text{-}(CH_3)_3\text{—}C_6H_2$ |
| 80 | $CH_3$ | $2,4,6\text{-}(CH_3)_3\text{—}C_6H_2$ |
| 81 | $CH_3$ | $3,4,5\text{-}(CH_3)_3\text{—}C_6H_2$ |
| 82 | $CH_3$ | $2,3,4,6\text{-}(CH_3)_4\text{—}C_6H$ |
| 83 | $CH_3$ | $2,3,5,6\text{-}(CH_3)_4\text{—}C_6H$ |
| 84 | $CH_3$ | $C_6(CH_3)_5$ |
| 85 | $CH_3$ | $2\text{-}C_2H_5\text{—}C_6H_4$ |
| 86 | $CH_3$ | $3\text{-}C_2H_5\text{—}C_6H_4$ |
| 87 | $CH_3$ | $4\text{-}C_2H_5\text{—}C_6H_4$ |
| 88 | $CH_3$ | $2,4\text{-}(C_2H_5)_2\text{—}C_6H_3$ |
| 89 | $CH_3$ | $2,6\text{-}(C_2H_5)_2\text{—}C_6H_3$ |
| 90 | $CH_3$ | $3,5\text{-}(C_2H_5)_2\text{—}C_6H_3$ |
| 91 | $CH_3$ | $2,4,6\text{-}(C_2H_5)_3\text{—}C_6H_3$ |
| 92 | $CH_3$ | $2\text{-}n\text{-}C_3H_7\text{—}C_6H_4$ |
| 93 | $CH_3$ | $3\text{-}n\text{-}C_3H_7\text{—}C_6H_4$ |
| 94 | $CH_3$ | $4\text{-}n\text{-}C_3H_7\text{—}C_6H_4$ |
| 95 | $CH_3$ | $2\text{-}i\text{-}C_3H_7\text{—}C_6H_4$ |
| 96 | $CH_3$ | $3\text{-}i\text{-}C_3H_7\text{—}C_6H_4$ |
| 97 | $CH_3$ | $4\text{-}i\text{-}C_3H_7\text{—}C_6H_4$ |
| 98 | $CH_3$ | $2,4\text{-}(i\text{-}C_3H_7)_2\text{—}C_6H_3$ |
| 99 | $CH_3$ | $2,6\text{-}(i\text{-}C_3H_7)_2\text{—}C_6H_3$ |
| 100 | $CH_3$ | $3,5\text{-}(i\text{-}C_3H_7)_2\text{—}C_6H_3$ |
| 101 | $CH_3$ | $2\text{-}s\text{-}C_4H_9\text{—}C_6H_4$ |
| 102 | $CH_3$ | $3\text{-}s\text{-}C_4H_9\text{—}C_6H_4$ |
| 103 | $CH_3$ | $4\text{-}s\text{-}C_4H_9\text{—}C_6H_4$ |
| 104 | $CH_3$ | $2\text{-}t\text{-}C_4H_9\text{—}C_6H_4$ |
| 105 | $CH_3$ | $3\text{-}t\text{-}C_4H_9\text{—}C_6H_4$ |
| 106 | $CH_3$ | $4\text{-}t\text{-}C_4H_9\text{—}C_6H_4$ |
| 107 | $CH_3$ | $4\text{-}n\text{-}C_9H_{19}\text{—}C_6H_4$ |
| 108 | $CH_3$ | $2\text{-}CH_3,\ 4\text{-}t\text{-}c_4H_9\text{—}C_6H_3$ |
| 109 | $CH_3$ | $2\text{-}CH_3,\ 6\text{-}t\text{-}c_4H_9\text{—}C_6H_3$ |
| 110 | $CH_3$ | $2\text{-}CH_3,\ 4\text{-}i\text{-}c_3H_7\text{—}C_6H_3$ |
| 111 | $CH_3$ | $2\text{-}CH_3,\ 5\text{-}i\text{-}c_3H_7\text{—}C_6H_3$ |
| 112 | $CH_3$ | $3\text{-}CH_3,\ 4\text{-}i\text{-}c_3H_7\text{—}C_6H_3$ |
| 113 | $CH_3$ | $2\text{-}c\text{-}C_6H_{11}\text{—}C_6H_4$ |
| 114 | $CH_3$ | $3\text{-}c\text{-}C_6H_{11}\text{—}C_6H_4$ |
| 115 | $CH_3$ | $4\text{-}c\text{-}C_6H_{11}\text{—}C_6H_4$ |
| 116 | $CH_3$ | $2\text{-}Cl,\ 4\text{-}C_6H_5\text{—}C_6H_3$ |
| 117 | $CH_3$ | $2\text{-}Br,\ 4\text{-}C_6H_5\text{—}C_6H_3$ |
| 118 | $CH_3$ | $2\text{-}OCH_3\text{—}C_6H_4$ |
| 119 | $CH_3$ | $3\text{-}OCH_3\text{—}C_6H_4$ |
| 120 | $CH_3$ | $4\text{-}OCH_3\text{—}C_6H_4$ |
| 121 | $CH_3$ | $2\text{-}OC_2H_5\text{—}C_6H_4$ |
| 122 | $CH_3$ | $3\text{-}OC_2H_5\text{—}C_6H_4$ |
| 123 | $CH_3$ | $4\text{-}OC_2H_5\text{—}C_6H_4$ |
| 124 | $CH_3$ | $2\text{-}O\text{-}n\text{-}C_3H_7\text{—}C_6H_4$ |
| 125 | $CH_3$ | $3\text{-}O\text{-}n\text{-}C_3H_7\text{—}C_6H_4$ |
| 126 | $CH_3$ | $4\text{-}O\text{-}n\text{-}C_3H_7\text{—}C_6H_4$ |
| 127 | $CH_3$ | $2\text{-}O\text{-}i\text{-}C_3H_7\text{—}C_6H_4$ |
| 128 | $CH_3$ | $3\text{-}O\text{-}i\text{-}C_3H_7\text{—}C_6H_4$ |
| 129 | $CH_3$ | $4\text{-}O\text{-}i\text{-}C_3H_7\text{—}C_6H_4$ |
| 130 | $CH_3$ | $2\text{-}O\text{-}n\text{-}C_6H_{13}\text{—}C_6H_4$ |
| 131 | $CH_3$ | $3\text{-}O\text{-}n\text{-}C_6H_{13}\text{—}C_6H_4$ |
| 132 | $CH_3$ | $4\text{-}O\text{-}n\text{-}C_6H_{13}\text{—}C_6H_4$ |
| 133 | $CH_3$ | $2\text{-}OCH_2C_6H_5\text{-}C_6H_4$ |
| 134 | $CH_3$ | $3\text{-}OCH_2C_6H_5\text{—}C_6H_4$ |
| 135 | $CH_3$ | $4\text{-}OCH_2C_6H_5\text{—}C_6H_4$ |
| 136 | $CH_3$ | $2\text{-}O(CH_2)_2C_6H_5\text{—}C_6H_4$ |
| 137 | $CH_3$ | $4\text{-}O(CH_2)_2C_6H_5\text{—}C_6H_4$ |
| 138 | $CH_3$ | $2,3\text{-}(OCH_3)_2\text{—}C_6H_3$ |
| 139 | $CH_3$ | $2,4\text{-}(OCH_3)_2\text{—}C_6H_3$ |
| 140 | $CH_3$ | $2,5\text{-}(OCH_3)_2\text{—}C_6H_3$ |
| 141 | $CH_3$ | $2,6\text{-}(OCH_3)_2\text{—}C_6H_3$ |
| 142 | $CH_3$ | $3,4\text{-}(OCH_3)_2\text{—}C_6H_3$ |
| 143 | $CH_3$ | $3,5\text{-}(OCH_3)_2\text{—}C_6H_3$ |
| 144 | $CH_3$ | $2\text{-}O\text{-}t\text{-}C_4H_9\text{—}C_6H_4$ |
| 145 | $CH_3$ | $3\text{-}O\text{-}t\text{-}C_4H_9\text{—}C_6H_4$ |
| 146 | $CH_3$ | $4\text{-}O\text{-}t\text{-}C_4H_9\text{—}C_6H_4$ |
| 147 | $CH_3$ | $3\text{-}(3'\text{-}Cl\text{-}C_6H_4)\text{—}C_6H_4$ |

TABLE A-continued

| No. | R⁴ | R⁵ |
|---|---|---|
| 148 | CH₃ | 4-(4'-Cl-C₆H₄)—C₆H₄ |
| 149 | CH₃ | 2-OC₆H₅—C₆H₄ |
| 150 | CH₃ | 3-OC₆H₅—C₆H₄ |
| 151 | CH₃ | 4-OC₆H₅—C₆H₄ |
| 152 | CH₃ | 2-O-(2'-F—C₆H₄)—C₆H₄ |
| 153 | CH₃ | 3-O-(3'-Cl—C₆H₄)—C₆H₄ |
| 154 | CH₃ | 4-O-(4'-CH₃—C₆H₄)—C₆H₄ |
| 155 | CH₃ | 2,3,6-(CH₃)₃, 4-F—C₆H |
| 156 | CH₃ | 2,3,6-(CH₃)₃, 4-Cl—C₆H |
| 157 | CH₃ | 2,3,6-(CH₃)₃, 4-Br—C₆H |
| 158 | CH₃ | 2,4-(CH₃)₂, 6-F—C₆H₂ |
| 159 | CH₃ | 2,4-(CH₃)₂, 6-Cl—C₆H₂ |
| 160 | CH₃ | 2,4-(CH₃)₂, 6-Br—C₆H₂ |
| 161 | CH₃ | 2-i-C₃H₇, 4-Cl, 5-CH₃—C₆H₂ |
| 162 | CH₃ | 2-Cl, 4-NO₂—C₆H₃ |
| 163 | CH₃ | 4-Cl, 2-NO₂—C₆H₃ |
| 164 | CH₃ | 2-OCH₃, 4-NO₂—C₆H₃ |
| 165 | CH₃ | 2,4-Cl₂, 5-NO₂—C₆H₂ |
| 166 | CH₃ | 2,4-Cl₂, 6-NO₂—C₆H₂ |
| 167 | CH₃ | 2,6-Cl₂, 4-NO₂—C₆H₂ |
| 168 | CH₃ | 2,6-Br₂, 4-NO₂—C₆H₂ |
| 169 | CH₃ | 2,6-I₂, 4-NO₂—C₆H₂ |
| 170 | CH₃ | 2-CH₃, 4-Cl, 5-i-C₃H₇—C₆H₂ |
| 171 | CH₃ | 2-CO₂CH₃—C₆H₄ |
| 172 | CH₃ | 3-CO₂CH₃—C₆H₄ |
| 173 | CH₃ | 4-CO₂CH₃—C₆H₄ |
| 174 | CH₃ | 2-CH₂OCH₃—C₆H₄ |
| 175 | CH₃ | 3-CH₂OCH₃—C₆H₄ |
| 176 | CH₃ | 4-CH₂OCH₃—C₆H₄ |
| 177 | CH₃ | 2-CH₃, 4-CO-i-C₃H₇—C₆H₃ |
| 178 | CH₃ | 2-CH₃, 4-C(CH₃)=NOCH₃—C₆H₃ |
| 179 | CH₃ | 2-CH₃, 4-C(CH₃)=NOC₂H₅—C₆H₃ |
| 180 | CH₃ | 2-CH₃, 4-C(CH₃)=NO-n-C₃H₇—C₆H₃ |
| 181 | CH₃ | 2-CH₃, 4-C(CH₃)=NO-i-C₃H₇—C₆H₃ |
| 182 | CH₃ | 2,5-(CH₃)₂, 4-C(CH₃)=NOCH₃—C₆H₂ |
| 183 | CH₃ | 2,5-(CH₃)₂, 4-C(CH₃)=NOC₂H₅—C₆H₂ |
| 184 | CH₃ | 2,5-(CH₃)₂, 4-C(CH₃)=NO-n-C₃H₇—C₆H₂ |
| 185 | CH₃ | 2,5-(CH₃)₂, 4-C(CH₃)=NO-i-C₃H₇—C₆H₂ |
| 186 | CH₃ | 2-C₆H₅—C₆H₄ |
| 187 | CH₃ | 3-C₆H₅—C₆H₄ |
| 188 | CH₃ | 4-C₆H₅—C₆H₄ |
| 189 | CH₃ | 2-(2'-F—C₆H₄)—C₆H₄ |
| 190 | CH₃ | 2-CH₃, 5-Br—C₆H₃ |
| 191 | CH₃ | 2-CH₃, 6-Br—C₆H₃ |
| 192 | CH₃ | 3-CH₃, 2-Cl—C₆H₃ |
| 193 | CH₃ | 4-CH₃, 2-Cl—C₆H₃ |
| 194 | CH₃ | 5-CH₃, 2-Cl—C₆H₃ |
| 195 | CH₃ | 3-CH₃, 2-F—C₆H₃ |
| 196 | CH₃ | 4-CH₃, 2-F—C₆H₃ |
| 197 | CH₃ | 5-CH₃, 2-F—C₆H₃ |
| 198 | CH₃ | 3-CH₃, 2-Br—C₆H₃ |
| 199 | CH₃ | 4-CH₃, 2-Br—C₆H₃ |
| 200 | CH₃ | 5-CH₃, 2-Br—C₆H₃ |
| 201 | CH₃ | 3-CH₃, 4-Cl—C₆H₃ |
| 202 | CH₃ | 3-CH₃, 5-Cl—C₆H₃ |
| 203 | CH₃ | 3-CH₃, 4-F—C₆H₃ |
| 204 | CH₃ | 3-CH₃, 5-F—C₆H₃ |
| 205 | CH₃ | 3-CH₃, 4-Br—C₆H₃ |
| 206 | CH₃ | 3-CH₃, 5-Br—C₆H₃ |
| 207 | CH₃ | 4-CH₃, 3-F—C₆H₃ |
| 208 | CH₃ | 4-CH₃, 3-Cl—C₆H₃ |
| 209 | CH₃ | 4-CH₃, 3-Br—C₆H₃ |
| 210 | CH₃ | 4,5-(CH₃)₂, 2-Cl—C₆H₂ |
| 211 | CH₃ | 4,5-(CH₃)₂, 2-Br—C₆H₂ |
| 212 | CH₃ | 3,5-(CH₃)₂, 2-Cl—C₆H₂ |
| 213 | CH₃ | 3,5-(CH₃)₂, 2-Br—C₆H₂ |
| 214 | CH₃ | 2,6-Cl₂, 4-CH₄—C₆H₃ |
| 215 | CH₃ | 2,6-F₂, 4-CH₄—C₆H₃ |
| 216 | CH₃ | 2,6-Br₂, 4-CH₄—C₆H₃ |
| 217 | CH₃ | 2,4-Br₂, 6-CH₄—C₆H₃ |
| 218 | CH₃ | 2,4-F₂, 6-CH₄—C₆H₃ |
| 219 | CH₃ | 2,4-Cl₂, 6-CH₄—C₆H₃ |
| 220 | CH₃ | 2,6-(CH₃)₂, 4-F—C₆H₂ |
| 221 | CH₃ | 2,6-(CH₃)₂, 4-Cl—C₆H₂ |
| 222 | CH₃ | 2,6-(CH₃)₂, 4-Br—C₆H₂ |
| 223 | CH₃ | 3,5-(CH₃)₂, 4-F—C₆H₂ |
| 224 | CH₃ | 3,5-(CH₃)₂, 4-Cl—C₆H₂ |
| 225 | CH₃ | 3,5-(CH₃)₂, 4-Br—C₆H₂ |
| 226 | CH₃ | 2-CF₃—C₆H₄ |
| 227 | CH₃ | 3-CF₃—C₆H₄ |
| 228 | CH₃ | 4-CF₃—C₆H₄ |
| 229 | CH₃ | 2-OCF₃—C₆H₄ |
| 230 | CH₃ | 3-OCF₃—C₆H₄ |
| 231 | CH₃ | 4-OCF₃—C₆H₄ |
| 232 | CH₃ | 3-OCH₂CHF₂—C₆H₄ |
| 233 | CH₃ | 2-NO₂—C₆H₄ |
| 234 | CH₃ | 3-NO₂—C₆H₄ |
| 235 | CH₃ | 4-NO₂—C₆H₄ |
| 236 | CH₃ | 2-CN—C₆H₄ |
| 237 | CH₃ | 3-CN—C₆H₄ |
| 238 | CH₃ | 4-CN—C₆H₄ |
| 239 | CH₃ | 2-CH₃, 3-Cl—C₆H₃ |
| 240 | CH₃ | 2-CH₃, 4-Cl—C₆H₃ |
| 241 | CH₃ | 2-CH₃, 5-Cl—C₆H₃ |
| 242 | CH₃ | 2-CH₃, 6-Cl—C₆H₃ |
| 243 | CH₃ | 2-CH₃, 3-F—C₆H₃ |
| 244 | CH₃ | 2-CH₃, 4-F—C₆H₃ |
| 245 | CH₃ | 2-CH₃, 5-F—C₆H₃ |
| 246 | CH₃ | 2-CH₃, 6-F—C₆H₃ |
| 247 | CH₃ | 2-CH₃, 3-Br—C₆H₃ |
| 248 | CH₃ | 2-CH₃, 4-Br—C₆H₃ |
| 249 | CH₃ | 2-CH₃, 5-Br—C₆H₃ |
| 250 | CH₃ | 2-CH₃, 6-Br—C₆H₃ |
| 251 | CH₃ | 2,5-F₂—C₆H₃ |
| 252 | CH₃ | 2,6-F₂—C₆H₃ |
| 253 | CH₃ | 3,4-F₂—C₆H₃ |
| 254 | CH₃ | 3,5-F₂—C₆H₃ | n = neo; i = iso; s = secondary; t = tertiary; c = cyclo

TABLE B

| No. | Rˣ |
|---|---|
| 01 | H |
| 02 | 2-F |
| 03 | 3-F |
| 04 | 4-F |
| 05 | 2,4-F₂ |
| 06 | 2,3-F₂ |
| 07 | 2,4,6-F₃ |
| 08 | 2,3,4,5,6-F₅ |
| 09 | 2-Cl |
| 10 | 3-Cl |
| 11 | 4-Cl |
| 12 | 2,3-Cl₂ |
| 13 | 2,4-Cl₂ |
| 14 | 2,5-Cl₂ |
| 15 | 2,6-Cl₂ |
| 16 | 3,4-Cl₂ |
| 17 | 3,5-Cl₂ |
| 18 | 2,3,4-Cl₃ |
| 19 | 2,3,5-Cl₃ |
| 20 | 2,3,6-Cl₃ |
| 21 | 2,4,5-Cl₃ |
| 22 | 2,4,6-Cl₃ |
| 23 | 3,4,5-Cl₃ |
| 24 | 2,3,4,6-Cl₄ |
| 25 | 2,3,5,6-Cl₄ |
| 26 | 2,3,4,5,6-Cl₅ |
| 27 | 2-Br |
| 28 | 3-Br |
| 29 | 4-Br |
| 30 | 2,4-Br₂ |
| 31 | 2,5-Br₂ |
| 32 | 2,6-Br₂ |
| 33 | 2,4,6-Br₃ |
| 34 | 2,3,4,5,6-Br₅ |
| 35 | 2-I |
| 36 | 3-I |
| 37 | 4-I |
| 38 | 2,4-I₂ |

TABLE B-continued

| No. | $R^x$ |
|---|---|
| 39 | 2-Cl, 3-F |
| 40 | 2-Cl, 4-F |
| 41 | 2-Cl, 5-F |
| 42 | 2-Cl, 6-F |
| 43 | 2-Cl, 3-Br |
| 44 | 2-Cl, 4-Br |
| 45 | 2-Cl, 5-Br |
| 46 | 2-Cl, 6-Br |
| 47 | 2-Br, 3-Cl |
| 48 | 2-Br, 4-Cl |
| 49 | 2-Br, 5-Cl |
| 50 | 2-Br, 6-Cl |
| 51 | 2-Br, 3-F |
| 52 | 2-Br, 4-F |
| 53 | 2-Br, 5-F |
| 54 | 2-Br, 6-F |
| 55 | 2-F, 3-Cl |
| 56 | 2-F, 4-Cl |
| 57 | 2-F, 5-Cl |
| 58 | 4-F, 3-Cl |
| 59 | 5-F, 3-Cl |
| 60 | 4-Br, 3-Cl |
| 61 | 5-Br, 3-Cl |
| 62 | 3-F, 4-Cl |
| 63 | 3-F, 4-Br |
| 64 | 3-Br, 4-Cl |
| 65 | 4-F, 3-Br |
| 66 | 2,6-Cl$_2$, 4-Br |
| 67 | 2-CH$_3$ |
| 68 | 3-CH$_3$ |
| 69 | 4-CH$_3$ |
| 70 | 2,3-(CH$_3$)$_2$ |
| 71 | 2,4-(CH$_3$)$_2$ |
| 72 | 2,5-(CH$_3$)$_2$ |
| 73 | 2,6-(CH$_3$)$_2$ |
| 74 | 3,4-(CH$_3$)$_2$ |
| 75 | 3,5-(CH$_3$)$_2$ |
| 76 | 2,3,4-(CH$_3$)$_3$ |
| 77 | 2,3,5-(CH$_3$)$_3$ |
| 78 | 2,3,6-(CH$_3$)$_3$ |
| 79 | 2,4,5-(CH$_3$)$_3$ |
| 80 | 2,4,6-(CH$_3$)$_3$ |
| 81 | 3,4,5-(CH$_3$)$_3$ |
| 82 | 2,3,4,6-(CH$_3$)$_4$ |
| 83 | 2,3,5,6-(CH$_3$)$_4$ |
| 84 | 2,3,4,5,6-(CH$_3$)5 |
| 85 | 2-C$_2$H$_5$ |
| 86 | 3-C$_2$H$_5$ |
| 87 | 4-C$_2$H$_5$ |
| 88 | 2,4-(C$_2$H$_5$)2 |
| 89 | 2,6-(C$_2$H$_5$)2 |
| 90 | 3,5-(C$_2$H$_5$)2 |
| 91 | 2,4,6-(C$_2$H$_5$)3 |
| 92 | 2-n-C$_3$H$_7$ |
| 93 | 3-n-C$_3$H$_7$ |
| 94 | 4-n-C$_3$H$_7$ |
| 95 | 2-i-C$_3$H$_7$ |
| 96 | 3-i-C$_3$H$_7$ |
| 97 | 4-i-C$_3$H$_7$ |
| 98 | 2,4-(i-C$_3$H$_7$)2 |
| 99 | 2,6-(i-C$_3$H$_7$)2 |
| 100 | 3,5-(i-C$_3$H$_7$)2 |
| 101 | 2-s-C$_4$H$_9$ |
| 102 | 3-s-C$_4$H$_9$ |
| 103 | 4-s-C$_4$H$_9$ |
| 104 | 2-t-C$_4$H$_9$ |
| 105 | 3-t-C$_4$H$_9$ |
| 106 | 4-t-C$_4$H$_9$ |
| 107 | 4-n-C$_9$H$_{19}$ |
| 108 | 2-CH$_3$, 4-t-C$_4$H$_9$ |
| 109 | 2-CH$_3$, 6-t-C$_4$H$_9$ |
| 110 | 2-CH$_3$, 4-i-C$_3$H$_7$ |
| 111 | 2-CH$_3$, 5-i-C$_3$H$_7$ |
| 112 | 3-CH$_3$, 4-i-C$_3$H$_7$ |
| 113 | 2-c-C$_6$H$_{11}$ |
| 114 | 3-c-C$_6$H$_{11}$ |
| 115 | 4-c-C$_6$H$_{11}$ |
| 116 | 2-Cl, 4-C$_6$H$_5$ |
| 117 | 2-Br, 4-C$_6$H$_5$ |
| 118 | 2-OCH$_3$ |
| 119 | 3-OCH$_3$ |
| 120 | 4-OCH$_3$ |
| 121 | 2-OC$_2$H$_5$ |
| 122 | 3-OC$_2$H$_5$ |
| 123 | 4-OC$_2$H$_5$ |
| 124 | 2-O-n-C$_3$H$_7$ |
| 125 | 3-O-n-C$_3$H$_7$ |
| 126 | 4-O-n-C$_3$H$_7$ |
| 127 | 2-O-i-C$_3$H$_7$ |
| 128 | 3-O-i-C$_3$H$_7$ |
| 129 | 4-O-i-C$_3$H$_7$ |
| 130 | 2-O-n-C$_6$H$_{13}$ |
| 131 | 3-O-n-C$_6$H$_{13}$ |
| 132 | 4-O-n-C$_6$H$_{13}$ |
| 133 | 2-OCH$_2$C$_6$H$_5$ |
| 134 | 3-OCH$_2$C$_6$H$_5$ |
| 135 | 4-OCH$_2$C$_6$H$_5$ |
| 136 | 2-O(CH$_2$)$_2$C$_6$H$_5$ |
| 137 | 4-O(CH$_2$)$_2$C$_6$H$_5$ |
| 138 | 2,3-(OCH$_3$)$_2$ |
| 139 | 2,4-(OCH$_3$)$_2$ |
| 140 | 2,5-(OCH$_3$)$_2$ |
| 141 | 2,6-(OCH$_3$)$_2$ |
| 142 | 3,4-(OCH$_3$)$_2$ |
| 143 | 3,5-(OCH$_3$)$_2$ |
| 144 | 2-O-t-C$_4$H$_9$ |
| 145 | 3-O-t-C$_4$H$_9$ |
| 146 | 4-O-t-C$_4$H$_9$ |
| 147 | 3-(3'-Cl-C$_6$H$_4$) |
| 148 | 4-(4'-Cl-C$_6$H$_4$) |
| 149 | 2-OC$_6$H$_5$ |
| 150 | 3-OC$_6$H$_5$ |
| 151 | 4-OC$_6$H$_5$ |
| 152 | 2-O-(2'-F—C$_6$H$_4$) |
| 153 | 3-O-(3'-Cl—C$_6$H$_4$) |
| 154 | 4-O-(4'-CH$_3$—C$_6$H$_4$) |
| 155 | 2,3,6-(CH$_3$)$_3$, 4-F |
| 156 | 2,3,6-(CH$_3$)$_3$, 4-Cl |
| 157 | 2,3,6-(CH$_3$)$_3$, 4-Br |
| 158 | 2,4-(CH$_3$)$_2$, 6-F |
| 159 | 2,4-(CH$_3$)$_2$, 6-Cl |
| 160 | 2,4-(CH$_3$)$_2$, 6-Br |
| 161 | 2-i-C$_3$H$_7$, 4-Cl, 5-CH$_3$ |
| 162 | 2-Cl, 4-NO$_2$ |
| 163 | 4-Cl, 2-NO$_2$ |
| 164 | 2-OCH$_3$, 4-NO$_2$ |
| 165 | 2,4-Cl$_2$, 5-NO$_2$ |
| 166 | 2,4-Cl$_2$, 6-NO$_2$ |
| 167 | 2,6-Cl$_2$, 4-NO$_2$ |
| 168 | 2,6-Br$_2$, 4-NO$_2$ |
| 169 | 2,6-I$_2$, 4-NO$_2$ |
| 170 | 2-CH$_3$, 4-Cl, 5-i-C$_3$H$_7$ |
| 171 | 2-CO$_2$CH$_3$ |
| 172 | 3-CO$_2$CH$_3$ |
| 173 | 4-CO$_2$CH$_3$ |
| 174 | 2-CH$_2$OCH$_3$ |
| 175 | 3-CH$_2$OCH$_3$ |
| 176 | 4-CH$_2$OCH$_3$ |
| 177 | 2-CH$_3$, 4-CO-i-C$_3$H$_7$ |
| 178 | 2-CH$_3$, 4-C(CH$_3$)=NOCH$_3$ |
| 179 | 2-CH$_3$, 4-C(CH$_3$)=NOC$_2$H$_5$ |
| 180 | 2-CH$_3$, 4-C(CH$_3$)=NO-n-C$_3$H$_7$ |
| 181 | 2-CH$_3$, 4-C(CH$_3$)=NO-i-C$_3$H$_7$ |
| 182 | 2,5-(CH$_3$)$_2$, 4-C(CH$_3$)=NOCH$_3$ |
| 183 | 2,5-(CH$_3$)$_2$, 4-C(CH$_3$)=NOC$_2$H$_5$ |
| 184 | 2,5-(CH$_3$)$_2$, 4-C(CH$_3$)=NO-n-C$_3$H$_7$ |
| 185 | 2,5-(CH$_3$)$_2$, 4-C(CH$_3$)=NO-i-C$_3$H$_7$ |
| 186 | 2-C$_6$H$_5$ |
| 187 | 3-C$_6$H$_5$ |
| 188 | 4-C$_6$H$_5$ |
| 189 | 2-(2'-F—C$_6$H$_4$) |
| 190 | 2-CH$_3$, 5-Br |
| 191 | 2-CH$_3$, 6-Br |
| 192 | 3-CH$_3$, 2-Cl |

TABLE B-continued

| No. | $R^x$ |
|---|---|
| 193 | 4-CH₃, 2-Cl |
| 194 | 5-CH₃, 2-Cl |
| 195 | 3-CH₃, 2-F |
| 196 | 4-CH₃, 2-F |
| 197 | 5-CH₃, 2-F |
| 198 | 3-CH₃, 2-Br |
| 199 | 4-CH₃, 2-Br |
| 200 | 5-CH₃, 2-Br |
| 201 | 3-CH₃, 4-Cl |
| 202 | 3-CH₃, 5-Cl |
| 203 | 3-CH₃, 4-F |
| 204 | 3-CH₃, 5-F |
| 205 | 3-CH₃, 4-Br |
| 206 | 3-CH₃, 5-Br |
| 207 | 4-CH₃, 3-F |
| 208 | 4-CH₃, 3-Cl |
| 209 | 4-CH₃, 3-Br |
| 210 | 4,5-(CH₃)₂, 2-Cl |
| 211 | 4,5-(CH₃)₂, 2-Br |
| 212 | 3,5-(CH₃)₂, 2-Cl |
| 213 | 3,5-(CH₃)₂, 2-Br |
| 214 | 2,6-Cl₂, 4-CH₄ |
| 215 | 2,6-F₂, 4-CH₄ |
| 216 | 2,6-Br₂, 4-CH₄ |
| 217 | 2,4-Br₂, 6-CH₄ |
| 218 | 2,4-F₂, 6-CH₄ |
| 219 | 2,4-Cl₂, 6-CH₄ |
| 220 | 2,6-(CH₃)₂, 4-F |
| 221 | 2,6-(CH₃)₂, 4-Cl |
| 222 | 2,6-(CH₃)₂, 4-Br |
| 230 | 3-OCF₃ |
| 231 | 4-OCF₃ |
| 232 | 3-OCH₂CHF₂ |
| 233 | 2-NO₂ |
| 234 | 3-NO₂ |
| 235 | 4-NO₂ |
| 236 | 2-CN |
| 237 | 3-CN |
| 238 | 4-CN |
| 239 | 2-CH₃, 3-Cl |
| 240 | 2-CH₃, 4-Cl |
| 241 | 2-CH₃, 5-Cl |
| 242 | 2-CH₃, 6-Cl |
| 243 | 2-CH₃, 3-F |
| 244 | 2-CH₃, 4-F |
| 245 | 2-CH₃, 5-F |
| 246 | 2-CH₃, 6-F |
| 247 | 2-CH₃, 3-Br |
| 248 | 2-CH₃, 4-Br |
| 249 | 2-CH₃, 5-Br |
| 250 | 2-CH₃, 6-Br |
| 251 | 2,5-F₂ |
| 252 | 2,6-F₂ |
| 253 | 3,4-F₂ |
| 254 | 3,5-F₂ | n = neo; i = iso; s = secondary; t = tertiary; c = cyclo

TABLE C

| No. | $R^3$ | $R^4$ | $R^d$ | $R^e$ |
|---|---|---|---|---|
| 01 | H | CH₃ | CH₃ | CH₃ |
| 02 | CH₃ | CH₃ | CH₃ | CH₃ |
| 03 | C₂H₅ | CH₃ | CH₃ | CH₃ |
| 04 | n-C₃H₇ | CH₃ | CH₃ | CH₃ |
| 05 | i-C₃H₇ | CH₃ | CH₃ | CH₃ |
| 06 | c-C₃H₅ | CH₃ | CH₃ | CH₃ |
| 07 | pyridin-2-yl | CH₃ | CH₃ | CH₃ |
| 08 | pyridin-3-yl | CH₃ | CH₃ | CH₃ |
| 09 | pyridin-4-yl | CH₃ | CH₃ | CH₃ |
| 10 | 5-CH₃-isox-azol-3-yl | CH₃ | CH₃ | CH₃ |
| 11 | phenyl | CH₃ | CH₃ | CH₃ |
| 12 | CH₃ | H | CH₃ | CH₃ |
| 13 | CH₃ | C₂H₅ | CH₃ | CH₃ |
| 14 | CH₃ | n-C₃H₇ | CH₃ | CH₃ |
| 15 | CH₃ | i-C₃H₇ | CH₃ | CH₃ |
| 16 | CH₃ | c-C₃H₅ | CH₃ | CH₃ |
| 17 | CH₃ | pyridin-2-yl | CH₃ | CH₃ |
| 18 | CH₃ | pyridin-3-yl | CH₃ | CH₃ |
| 19 | CH₃ | pyridin-4-yl | CH₃ | CH₃ |
| 20 | CH₃ | 5-CH₃-isox-azol-3-yl | CH₃ | CH₃ |
| 21 | CH₃ | phenyl | CH₃ | CH₃ |
| 22 | CH₃ | CH₃ | H | CH₃ |
| 23 | CH₃ | CH₃ | C₂H₅ | CH₃ |
| 24 | CH₃ | CH₃ | n-C₃H₇ | CH₃ |
| 25 | CH₃ | CH₃ | i-C₃H₇ | CH₃ |
| 26 | CH₃ | CH₃ | c-C₃H₅ | CH₃ |
| 27 | CH₃ | CH₃ | pyridin-2-yl | CH₃ |
| 28 | CH₃ | CH₃ | pyridin-3-yl | CH₃ |
| 29 | CH₃ | CH₃ | pyridin-4-yl | CH₃ |
| 30 | CH₃ | CH₃ | 5-CH₃-isox-azol-3-yl | CH₃ |
| 31 | CH₃ | CH₃ | phenyl | CH₃ |
| 32 | CH₃ | CH₃ | CH₃ | C₂H₅ |
| 33 | CH₃ | CH₃ | CH₃ | n-C₃H₇ |
| 34 | CH₃ | CH₃ | CH₃ | i-C₃H₇ |
| 35 | CH₃ | CH₃ | CH₃ | t-C₄H₉ |
| 36 | CH₃ | CH₃ | CH₃ | benzyl |
| 37 | CH₃ | CH₃ | CH₃ | propargyl |
| 38 | CH₃ | CH₃ | CH₃ | bromopropargyl |
| 39 | CH₃ | CH₃ | CH₃ | iodopropargyl |
| 30 | CH₃ | CH₃ | CH₃ | allyl |
| 41 | CH₃ | CH₃ | CH₃ | trans-chloro-allyl |
| 42 | CH₃ | CH₃ | CH₃ | CH₂CH₂OCH₃ | n = neo; i = iso; s = secondary; t = tertiary; c = cyclo

The present invention also relates to intermediates of the formulae IV and V

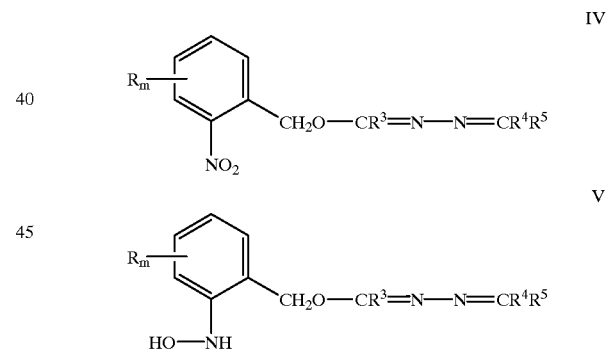

where R, $R^3$, $R^4$, $R^5$ and m have the above-mentioned meanings.

The preparation of compounds IV and V is described on pages 5 to 7.

The compounds I are useful as fungicides.

The compounds I are distinguished by an outstanding activity against a wide spectrum of phytopathogenic fungi, in particular from the classes of the Ascomycetes, Phycomycetes and asidiomycetes. Some of them act systemically and can be employed in crop protection as foliar- and soil-acting fungicides.

They are especially important for controlling a large number of fungi on a variety of crop plants such as wheat, rye, barley, oats, rice, maize, grass, cotton, soya, coffee, sugar cane, grapevine, fruit species, ornamentals and vegetable species such as cucumbers, beans and cucurbits, and on the seeds of these plants.

Specifically, they are suitable for controlling the following plant diseases: *Erysiphe graminis* (powdery mildew) in cereals, *Erysiphe cichoracearum* and *Sphaerotheca fuliginea* in cucurbits, *Podosphaera leucotricha* in apples, *Uncinula necator* in grapevines, Puccinia species in cereals, Rhizoctonia species in cotton, rice and lawns, Ustilago species in cereals and sugar cane, *Venturia inaequalis* (scab) in apples, Helminthosporium species in cereals, *Septoria nodorum* in wheat, *Botrytis cinerea* (gray mold) in strawberries, vegetables, ornamentals, grapevines, *Cercospora arachidicola* in groundnuts, *Pseudocercosporella herpotrichoides* in wheat and barley, *Pyricularia oryzae* in rice, *Phytophthora infestans* in potatoes and tomatoes, Fusarium and Verticillium species in a variety of plants, *Plasmopara viticola* in grapevines, and Alternaria species in vegetables and fruit.

Moreover, the compounds I are suitable for controlling harmful fungi in the protection of materials (eg. wood, paper, fibers or wovens) and in the protection of stored products.

The compounds I are used by treating the fungi, or the plants, seeds, materials or the soil to be protected against fungal infection, with a fungicidally active amount of the active ingredients. Application is effected before or after infection of the materials, plants or seeds by the fungi.

They can be converted into the customary formulations, such as solutions, emulsions, suspensions, dusts, powders, pastes and granules. The use form depends on the intended purpose; in any case, it should guarantee fine and uniform distribution of the compound according to the invention. The formulations are prepared in a known manner, eg. by extending the active ingredient with solvents and/or carriers, if desired using emulsifiers and dispersants, it also being possible to use other organic solvents as auxiliary solvents if water is used as the diluent. Suitable auxiliaries are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly-disperse silica, silicates); emulsifiers such as non-ionic and anionic emulsifiers (eg. polyoxyethylene fatty alcohol ethers, alkylsulfonates and arylsulfonates) and dispersants such as lignin-sulfite waste liquors and methylcellulose.

In general, the fungicidal compositions comprise from 0.1 to 95, preferably 0.5 to 90, % by weight of active ingredient.

The rates of application for use in crop protection are from 0.01 to 2.0 kg of active ingredient per ha, depending on the nature of the desired effect.

In the case of seed treatment, amounts of active ingredient of from 0.001 to 0.1 g, preferably 0.01 to 0.05 g, are generally required per kilogram of seed.

When used in the protection of materials or of stored products, the rate of active ingredient to be applied depends on the type of harmful fungus or the field of application. Usual rates of application in the protection of materials are, for example, from 0.001 g to 2 kg, preferably 0.005 g to 1 kg, of active ingredient per cubic meter of material treated.

In their use form as fungicides, the compositions according to the invention can also be present together with other active ingredients, eg. with herbicides, insecticides, growth regulators, fungicides, or else with fertilizers.

A mixture with fungicides frequently results in a widened fungicidal spectrum of action.

The following list of fungicides together with which the compounds according to the invention can be used is intended to illustrate possible combinations, but not to impose any limitation:

sulfur, dithiocarbamates and their derivatives, such as iron dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl) disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenyl isopropylcarbonate, diisopropyl 5-nitro-isophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, 1-(butylcarbamoyl)-2-benzimidazolecarbamate, 2-methoxycarbonylaminobenzimidazole, 2-(2-furyl)benzimidazole, 2-((4-thiazolyl)benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfuramide, 5-ethoxy-3-trichloromethyl-1,2,4-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl 2,5-dimethylfuran-3-carboxamide, N-cyclohexyl-N-methoxy-2,5-dimethylfuran-3-carboxamide, 2-methylbenzanilide, 2-iodobenzanilide, N-2,2,2-trichloro-1-(4-morpholinyl)ethylformamide, piperazine-1,4-diylbis(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-triazol-1-yl)-2-butanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and a variety of fungicides, such as dodecylguanidine acetate, 3-[3-(3,5-dimethyl-2-oxycyclohexyl)-2-hydroxyethyl]glutarimide, hexachlorobenzene, DL-methyl-N-(2,6-dimethylphenyl)-N-(2-furoyl)alaninate, DL-N-(2,6-dimethylphenyl)-N-(2'-methoxyacetyl)alanine methyl ester, N-(2,6-dimethylphenyl)-N-chloroacetyl-D,L-2- aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethyl-aminocarbonyl)-2-methoximino]acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis-(4-fluorophenyl)methylsilyl)methyl)-1H-1,2,4-triazole.

The compounds of the formula I are furthermore suitable for effectively controlling pests from the classes of the insects, arachnids and nematodes. They can be employed as pesticides in crop protection and in the hygiene, stored-product and veterinary sector.

The harmful insects include, from the order of the lepidopterans (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege stictiKalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.*

From the order of the beetles (Coleoptera), for example, *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius Kalifornicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus, Sitophilus granaria.*

From the order of the dipterans (Diptera), for example, *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.*

From the order of the thrips (Thysanoptera), for example, *Frankliniella fusca, Frankliniella occidentalis, Frankliniella tritici, Scirtothrips citri, Thrips oryzae, Thrips palmi, Thrips tabaci.*

From the order of the hymenopterans (Hymenoptera), for example, *Athalia rosae, Atta cephalotes, Atta sexdens, Atta texana, Hoplocampa minuta, Hoplocampa testudinea, Monomorium pharaonis, Solenopsis geminata, Solenopsis invicta.*

From the order of the heteropterans (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor.*

From the order of the homopterans (Homoptera), for example, *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphum rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii.*

From the order of the termites (Isoptera), for example, *Kalotermes flavicollis, Leucotermes flavipes, Reticulitermes lucifugus, Termes natalensis.*

From the order of the orthopterans (Orthoptera), for example, *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.*

From the class of the Arachnoidea, for example, arachnids (Acarina) such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Der-*

*manyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.*

From the class of the nematodes, for example, root knot nematodes, eg. *Meloidogyne hapla, Meloidogyne incognita, Meloidogyne javanica,* cyst-forming nematodes, eg. *Globodera rostochiensis, Heterodera avenae, Heterodera glycines, Heterodera schachtii, Heterodera trifolii,* stem eelworms and foliar nematodes, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.*

The active ingredients can be used as such, in the form of their formulations or the use forms prepared therefrom, for example in the form of directly sprayable solutions, powders, suspensions or dispersions, emulsions, oil dispersions, pastes, dusts, materials for spreading or granules by means of spraying, atomizing, dusting, spreading or pouring. The use forms depend entirely on the intended purposes; in any case, they should guarantee the finest possible distribution of the active ingredients according to the invention.

The concentrations of active ingredient in the ready-to-use preparations can be varied within substantial ranges.

In general, they are from 0.0001 to 10%, preferably from 0.01 to 1%.

The active ingredients can also be used successfully in the ultra-low-volume method (ULV), it being possible to apply formulations comprising over 95% by weight of active ingredient, or even the active ingredient without additives.

The rate of active ingredient to be applied for controlling pests is 0.1 to 2.0, preferably 0.2 to 1.0, kg/ha under field conditions.

Substances which are suitable for the preparation of directly sprayable solutions, emulsions, pastes or oil dispersions are mineral oil fractions of medium to high boiling point such as kerosine or diesel oil, furthermore coal tar oils and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, and strongly polar solvents, eg. dimethylformamide, dimethyl sulfoxide, N-methylpyrrolidone or water.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetting agent, adhesive, dispersant or emulsifier. It is also possible to prepare concentrates composed of active ingredient, wetting agent, adhesive, dispersant or emulsifier and, if desired, solvent or oil, which are suitable for dilution with water.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene, or of naphthalenesulfonic acid, with phenol and formaldehyde, polyoxyethylene octylphenyl ether, ethoxylated isooctylphenol, octylphenol, nonylphenol, alkylphenol polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Powders, materials for spreading and dusts can be prepared by mixing or grinding the active ingredients together with a solid carrier.

In general, the formulations comprise from 0.01 to 95% by weight, preferably 0.1 to 90% by weight, of the active ingredient. The active ingredients are employed in a purity of from 90% to 100%, preferably 95% to 100% (according to NMR spectrum).

Examples of formulations are:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of this silica gel. This gives a preparation of the active ingredient which has good adherence properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mole of oleic acid N-monoethanolamide, 2 parts by weight of calcium dodecylbenzenesulfonate and 2 parts by weight of the adduct of 40 mol of ethylene oxide to 1 mole of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mole of isooctylphenol and 5 parts by weight of the adduct of 40 mol of ethylene oxide to 1 mole of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel and the mixture is ground in a hammer mill (comprises 80% by weight of active ingredient).

VI. 90 parts by weight of a compound according to the invention are mixed with 10 parts by weight of N-methyl-α-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mole of isooctylphenol and 10 parts by weight of the adduct of 40 mol of ethylene oxide and 1 mole of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-a-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

Granules, eg. coated granules, impregnated granules and homogeneous granules, can be prepared by binding the active ingredients to solid carriers. Examples of solid carriers are mineral earths such as silica gel, silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, eg. ammonium sulfate, ammonium phosphate, ammonium nitrate or ureas, and products of vegetable origin, such as cereal meal, tree bark meal, wood meal and nutshell meal, cellulose powders and other solid carriers.

Various types of oils, or herbicides, fungicides, other pesticides, or bactericides, may be added to the active ingredients, if desired also immediately prior to use (tank mix). These can be admixed with the compositions according to the invention in a weight ratio of 1:10 to 10:1.

SYNTHESIS EXAMPLES

The protocols given in the synthesis examples which follow were used, with appropriate modification of the starting compounds, for obtaining other compounds I. The resulting compounds together with physical data are listed in the table which follows.

1. Preparation of

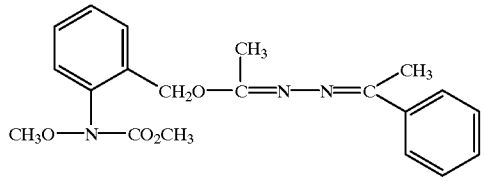

A mixture of 3.8 g (20 mmol) of N-acetylacetophenone hydrazone in 15 ml of dimethylformamide was treated with 0.6 g (26 mmol) of sodium hydride, a little at a time, and the mixture was stirred until the evolution of gas had ceased. The resulting mixture was subsequently treated with 8.4 g (20 mmol) of methyl N-methoxy-N-(o-bromomethylphenyl)carbamate (as described in WO-A 93/15,046, purity approximately 70%), and stirring was continued for 12 hours at approximately 25° C.

For working-up, the reaction mixture was treated with water and extracted repeatedly using tert-butyl methyl ether. After washing with water, drying and removing the solvent, the crude product obtained from the combined organic phases was purified by column chromatography (eluent: a) cyclohexane/methylene chloride, b) cyclohexane/ethyl acetate). This gave 0.2 g (3%) of the title compound as a pale oil.

$^1$H-NMR (CDCl$_3$; δ in ppm): 2.2 (s, 3H, CH$_3$); 2.3 (s, 3H, CH$_3$); 3.75 (s, 3H, OCH$_3$); 3.8 (s, 3H, OCH$_3$); 5.35 (s, 2H, OCH$_2$); 7.4 (m, 6H, phenyl); 7.55 (m, 1H, phenyl); 7.85 (m, 2H, phenyl)

2. Preparation of

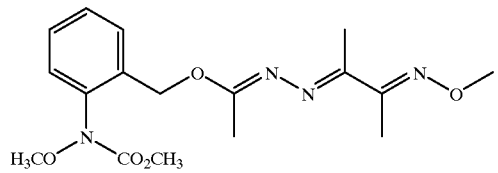

a) Diacetyl 0-methyloxime N-acetylhydrazone

A mixture of 6.0 g (52 mmol) of diacetyl O-methyloxime, 3.9 g (52 mmol) of acetylhydrazine and 3 drops of concentrated hydrochloric acid in 50 ml of methanol was stirred overnight (approximately 12 hours) at room temperature (approximately 20° C). The product which had crystallized out was isolated. The mother liquor was concentrated, product residues crystallizing out. In total, 4.0 g (45%) of the title compound were obtained.

$^1$H-NMR (d$_6$-DMSO; δ in ppm): 1.95 (s, 3H, CH$_3$), 2.00 (s, 3H, CH$_3$), 2.20 (s, 3H, CH$_3$), 3.90 (s, 3H, OCH$_3$), 10.60 (s, broad, 1H, NH)

b) Title compound

A mixture of 1.85 g (11 mol) of diacetyl O-methyloxime N-acetylhydrazone (Example 2a) and 0.29 g (12 mmol) of sodium hydride in 20 ml of dimethylformamide was stirred for 15 minutes at room temperature.

3.3 g (11 mol) of methyl N-methoxy-N-(o-bromomethylphenyl)carbamate (as described in WO-A 93/15046; purity approximately 90%) were subsequently added, and the mixture was stirred for approximately 1.5 hours at room temperature. The reaction mixture was subsequently diluted with water and the aqueous phase was extracted three times with methyl t-butyl ether. The combined organic phases were washed with water, dried over magnesium sulfate and concentrated. The residue was purified by column chromatography (eluent: cyclohexane/methyl t-butyl ether). 1.3 g (32%) of the title compound were obtained as a yellow oil.

$^1$H-NMR (CDCl$_3$; δ in ppm): 2.05 (s, 3H, CH$_3$), 2.10 (s, 3H, CH$_3$), 3.70 (s, 3H, OCH$_3$), 3.75 (s, 3H, OCH$_3$), 3.95 (s, 3H, OCH$_3$), 5.30 (s, 2H, OCH$_2$), 7.40 (m, 3H, phenyl), 7.55 (m, 1H, phenyl)

TABLE D

I $R_m$—[phenyl]—CH$_2$O—CR$^3$=N—N=CR$^4$R$^5$
$R^2$O—N—COXR$^1$

| No. | $R_m$ | $XR^1$ | $R^2$ | $R^3$ | $R^4$ | $R^5$ | Physical data: $^1$H NMR [ppm] |
|---|---|---|---|---|---|---|---|
| I1.01 | — | OCH$_3$ | CH$_3$ | CH$_3$ | CH$_3$ | C$_6$H$_5$ | 2.2; 2.3; 3.75; 3.8; 5.35; 7.4; 7.55; 7.85 |

TABLE E

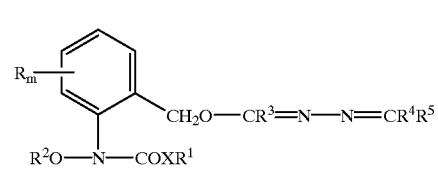

| No. | R³ | R⁴ | Rᵈ | Re | Physical data: ¹H NMR [ppm] |
|---|---|---|---|---|---|
| I2.01 | CH₃ | CH₃ | CH₃ | CH₃ | 2.05; 2.10; 3.70; 3.75; 3.95; 5.30; 7.40; 7.55; |

Examples of the action against harmful fungi

The fungicidal action of the compounds of the general formula I was demonstrated by the experiments which follow:

The active ingredients were formulated as a 10% strength emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Emulphor® EL (Emulan® EL, emulsifier based on ethoxylated fatty alcohols) and diluted with water to give the desired concentration.

Action against *Plasmopara viticola* (downy mildew of grapevine) Grapevines in pots (cultivar: "*Muller Thurgau*") were sprayed to drip point with the preparation of the active ingredient (rate of application: 63 ppm). After 8 days, the plants were sprayed with a zoospore suspension of the fungus *Plasmopara viticola* and kept at 20–30° C. at high atmospheric humidity, initially for 2 days. The test plants were subsequently grown in the greenhouse for 5 days. Prior to assessment, the plants were then kept at high atmospheric humidity for 16 hours. The evaluation was carried out visually.

In this test, the plants which had been treated with compound I1.01 from Table D showed a disease level of 5% in comparison with 70% in the untreated plants.

Action against Puccinia recondita (leaf rust of wheat)

Leaves of wheat seedlings (variety "Kanzler") were dusted with leaf rust spores (*Puccinia recondita*). The treated plants were incubated for 24 hours at 20–22° C. and a relative atmospheric humidity of 90–95% and subsequently treated with the aqueous preparation of the active ingredient (rate of application: 63 ppm). After a further 8 days at 20–22° C. and a relative atmospheric humidity of 65–70%, the degree of fungal development was determined. The evaluation was carried out visually.

In this test, the plants which had been treated with compound I1.01 from Table D and those with compound I2.01 from Table E showed a disease level of 0% in comparison with 75% in the untreated plants.

Examples of the action against animal pests

The action of the compounds of the general formula I against animal pests was demonstrated by the experiments which follow:

The active ingredients were formulated a. as an 0.1% strength solution in acetone or b. as a 10% strength emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Emulphor® EL (Emulan® EL, emulsifier based on ethoxylated fatty alcohols) and diluted to give the desired concentration, using acetone in the case of a. or water in the case of b.

After the experiments had ended, in each case the lowest con was determined at which 80 to 100% inhibition or mortality was still caused by the compounds in comparison with untreated controls (limit or minimal concentration).

We claim:

1. A phenylcarbamate of the formula I where the substituents and the index have the following meanings:

R is cyano, nitro, trifluoromethyl, halogen, $C_1$–$C_4$-alkyl or $C_1$–$C_4$-alkoxy;

m is 0, 1 or 2, it being possible for the radicals R to be different if n is 2;

$R^1$ is alkyl, alkenyl, alkynyl, cycloalkyl or cycloalkenyl, and, in the event that X is $NR^a$, additionally hydrogen;

X is a direct bond, O or $NR^a$;

$R^a$ is hydrogen, alkyl, alkenyl, alkynyl, cycloalkyl or cycloalkenyl;

$R^2$ is hydrogen, unsubstituted or substituted alkyl, alkenyl, alkynyl, cycloalkyl, cycloalkenyl, cycloalkynyl, alkylcarbonyl or alkoxycarbonyl;

$R^3$ and $R^4$ independently of one another are hydrogen, cyano, nitro, hydroxyl, amino, halogen, $C_1$–$C_6$-alkyl, $C_1$–$C_6$-alkoxy, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_2$–$C_6$-alkenylthio, $C_2$–$C_6$-alkenylamino, N—$C_2$–$C_6$-alkenyl-N—$C_1$–$C_6$-alkylamino, $C_2$–$C_6$-alkynyl, $C_2$–$C_6$-alkynyloxy, $C_2$–$C_6$-alkynylthio, $C_2$–$C_6$-alkynylamino, N—$C_2$–$C_6$-alkynyl-N—$C_1$–$C_6$-alkylamino, it being possible for the hydrocarbon radicals of these groups to be partially or fully halogenated and/or to have attached to them one to three of the following radicals:

cyano, nitro, hydroxyl, mercapto, amino, carboxyl, aminocarbonyl, aminothiocarbonyl, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyloxy, $C_3$–$C_6$-cycloalkyl, $C_3$–$C_6$-cycloalkoxy, heterocyclyl, heterocyclyloxy, aryl, aryloxy, aryl-$C_1$–$C_4$-alkoxy, arylthio, aryl-$C_1$–$C_4$-alkylthio, hetaryl, hetaryloxy, hetaryl-$C_1$–$C_4$-alkoxy, hetarylthio and hetaryl-$C_1$–$C_4$-alkylthio, it being possible for the cyclic radicals, in turn, to be partially or fully halogenated and/or to have attached to them one to three of the following groups: cyano, nitro, hydroxyl, mercapto, amino, carboxyl, aminopcarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio and $C(=NOR^b)$—$A_n$—$R^c$;

$C_3$–$C_6$-cycloalkyl, $C_3$–$C_6$-cycloalkoxy, $C_3$–$C_6$-cycloalkylthio, $C_3$–$C_6$-cycloalkylamino, N—$C_3$–$C_6$-cycloalkyl-N—$C_1$–$C_6$-alkylamino, $C_5$–$C_8$-cycloalkenyl, $C_5$–$C_8$-cycloalkenyloxy, $C_5$–$C_8$-cycloalkenylthio, $C_5$–$C_8$-cycloalkenylamino, N—$C_5$–$C_8$-cycloalkenyl-N—$C_1$–$C_6$-alkylamino, heterocyclyl, heterocyclyloxy, heterocyclylthio, heterocyclylamino, N-heterocyclyl-N—$C_1$–$C_6$-alkylamino, aryl, aryloxy, arylthio, arylamino, N-aryl-N—$C_1$–$C_6$-alkylamino, hetaryl, hetaryloxy, hetarylthio, hetarylamino, N-hetaryl-N—$C_1$–$C_6$-alkylamino, it being possible for the cyclic radicals to be partially or fully halogenated and/or to have attached to them one to three of the following groups:

cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-alkoxy-$C_1$–$C_6$-alkyl, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, aryl-$C_1$–$C_6$-alkoxy, aryl, aryloxy, hetaryl, hetaryloxy, it being possible for the cyclic radicals of the six last-mentioned groups to be partially or fully halogenated and/or to have attached to them a $C_1$–$C_6$-alkyl group; $C(=NOR^b)$—$A_n$—$R^c$ or $NR^f$—CO—D—$R^g$;

A is oxygen, sulfur or nitrogen, the nitrogen having attached to it hydrogen or $C_1$–$C_6$-alkyl;

D is a direct bond, oxygen or $NR^h$;

n is 0 or 1;

$R^b$ and $R^c$ independently of one another are hydrogen or $C_1$–$C_6$-alkyl;

$R^f$ is hydrogen, hydroxyl, $C_1$–$C_6$-alkyl, $C_2$–$C_6$-alkenyl, $C_2$–$C_6$-alkynyl, $C_1$–$C_6$-alkoxy, $C_2$–$C_6$-alkenyloxy, $C_2$–$C_6$-alkynyloxy, $C_1$–$C_6$-alkoxy-$C_1$–$C_6$-alkyl, $C_1$–$C_6$-alkoxy-$C_1$–$C_6$-alkoxy and $C_1$–$C_6$-alkoxycarbonyl;

$R^g$, $R^h$ independently of one another are hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl and hetaryl-$C_1$–$C_6$-alkyl;

$R^5$ is $CR^d=NOR^e$;

$R^d$ is one of the groups mentioned under $R^3$;

$R^e$ is hydrogen, $C_1$–$C_{10}$-alkyl, $C_3$–$C_6$-cycloalkyl, $C_2$–$C_{10}$-alkenyl, $C_2$–$C_{10}$-alkynyl, $C_1$–$C_{10}$-alkylcarbonyl, $C_2$–$C_{10}$-alkenylcarbonyl, $C_2$–$C_{10}$-alkynylcarbonyl or $C_1$–$C_{10}$-alkylsulfonyl, it being possible for these radicals to be partially or fully halogenated and/or to have attached to them one to three of the following groups:

cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, $C_3$–$C_6$-cycloalkyl, $C_3$–$C_6$-cycloalkyloxy, heterocyclyl, heterocyclyloxy, benzyl, benzyloxy, aryl, aryloxy, arylthio, hetaryl, hetaryloxy and hetarylthio, it being possible for the last twelve groups mentioned, in turn, to be partially or fully halogenated and/or to have attached to them one to three of the following groups:

cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio or $C(=NOR^b)$—$A_n$—$R^c$;

aryl, arylcarbonyl, arylsulfonyl, hetaryl, hetarylcarbonyl or hetarylsulfonyl, it being possible for these radicals to be partially or fully halogenated and/or to have attached to them one to three of the following groups:

cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy or $C(=NOR^b)$—$A_n$—$R^c$;

or a salt thereof.

2. A compound of the formula I as claimed in claim 1 where m is 0.

3. A compound of the formula I as claimed in claim 1 where $R^1$ is methyl.

4. A process for the preparation of a compound I as claimed in claim 1 where $R^3$ is not halogen, which comprises reacting a benzyl derivative of the formula II

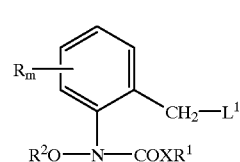

II where $L^1$ is a nucleophilically exchangeable leaving group with a carbohydrazide of the formula III

III.

5. A composition suitable for controlling pests or harmful fungi, comprising a solid or liquid carrier and a compound of the general formula I as claimed in claim 1.

6. A method of controlling harmful fungi, which comprises treating the fungi, or the materials, plants, the soil or seeds to be protected against fungal infection, with an effective amount of a compound of the general formula I as claimed in claim 1.

7. A method of controlling pests, which comprises treating the pests, or the materials, plants, the soil or seeds to be protected from them, with an effective amount of a compound of the general formula I as claimed in claim 1.

\* \* \* \* \*